United States Patent
Njoroge et al.

(10) Patent No.: US 6,228,856 B1
(45) Date of Patent: *May 8, 2001

(54) COMPOUNDS USEFUL FOR INHIBITION OF FARNESYL PROTEIN TRANSFERASE

(75) Inventors: F George Njoroge, Union; Arthur G. Taveras, Rockaway; Ronald J. Doll, Maplewood; Tarik Lalwani, Edison; Carmen Alvarez, Roselle Park; Stacy W. Remiszewski, Washington Township, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/417,885

(22) Filed: Oct. 14, 1999

Related U.S. Application Data

(62) Division of application No. 08/927,731, filed on Sep. 11, 1997, now Pat. No. 6,030,982.
(60) Provisional application No. 60/050,009, filed on Jun. 17, 1997, and provisional application No. 60/025,249, filed on Sep. 13, 1996.

(51) Int. Cl.[7] ............... A61K 31/4545; A61K 31/541; A61K 31/5355; C07D 401/14; C07D 413/14; C07D 417/14
(52) U.S. Cl. ........................ 514/228.2; 514/232.8; 514/290; 544/58.2; 544/126; 546/93
(58) Field of Search ............... 546/93; 514/290, 514/232.8, 228.2; 544/126, 58.2

(56) References Cited

U.S. PATENT DOCUMENTS

| | | |
|---|---|---|
| 4,826,853 | 5/1989 | Piwinski et al. ............ 514/290 |
| 5,089,496 | 2/1992 | Piwinski et al. ............ 514/253 |
| 5,151,423 | 9/1992 | Piwinski et al. ............ 514/254 |

(List continued on next page.)

FOREIGN PATENT DOCUMENTS

| | | |
|---|---|---|
| 0270818 | 6/1988 | (EP). |
| 0396083 | 11/1990 | (EP). |
| 0495484 | 7/1992 | (WO). |

(List continued on next page.)

OTHER PUBLICATIONS

Bishop et al., The Journal of Biological Chemistry, vol. 270, No. 15, pp. 30611–30618 (1995).
Njoroge et al., Bioorganic & Medicinal Chemistry Letters, vol. 6, No. 24, pp. 2977–2982 (1996).
Buss, J.E. et al. "Farnesyl transferase inhibitors the successes and surprises of a new class of potential cancer chemotherapeutics" Chem. Biol., vol. 2, Dec. 1995, pp. 787–791.
Njoroge, F.G. et al., "Discovery of a novel Nonpeptide Tricyclic Inhibitors of RAS Farnesyl Transferase" Bioorg. & Med. Chem. Lett., vol. 5, No. 1, 1997, pp. 101–113.

Primary Examiner—Evelyn Mei Huang
(74) Attorney, Agent, or Firm—Henry C. Jeanette; Margaret M. Albanese

(57) ABSTRACT

Novel compounds of the formula:

(1.0)

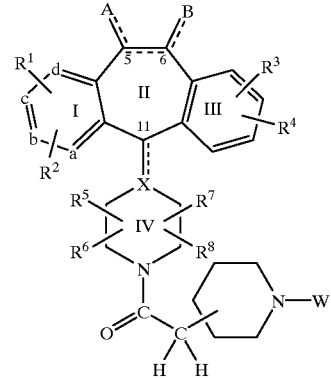

are disclosed. Compounds of Formula 1.0 are represented by the compounds of formulas:

(1.4)

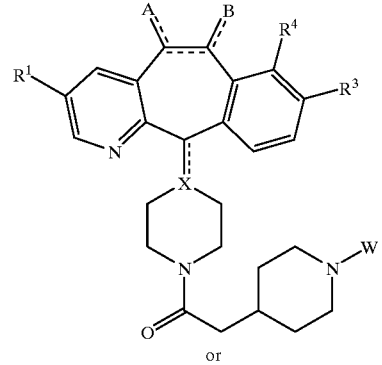

or (1.5)

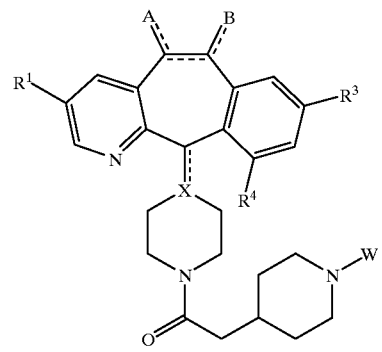

wherein $R^1$, $R^3$ and $R^4$ are each independently selected from halo. Also disclosed are methods of inhibiting farnesyl protein transferase and the growth of abnormal cells, such as tumor cells.

24 Claims, No Drawings

U.S. PATENT DOCUMENTS

| | | | |
|---|---|---|---|
| 5,393,890 | 2/1995 | Syoji et al. | 546/80 |
| 5,661,152 | 8/1997 | Bishop et al. | 514/254 |
| 5,672,611 | 9/1997 | Doll et al. | 514/325 |
| 5,684,013 | 11/1997 | Afonso et al. | 514/290 |
| 5,696,121 | 12/1997 | Bishop et al. | 514/254 |
| 5,700,806 | 12/1997 | Doll et al. | 514/290 |
| 5,703,090 | 12/1997 | Afonso et al. | 514/290 |
| 5,712,280 | 1/1998 | Doll et al. | 514/253 |
| 5,714,609 | 2/1998 | Bishop et al. | 546/93 |
| 5,719,148 | 2/1998 | Bishop et al. | 514/228.2 |
| 5,721,236 | 2/1998 | Bishop et al. | 514/255 |
| 5,728,703 | 3/1998 | Bishop et al. | 514/254 |

FOREIGN PATENT DOCUMENTS

| | | |
|---|---|---|
| WO/9510514 | 4/1995 | (WO) . |
| WO95/10515 | 4/1995 | (WO) . |
| WO95/10516 | 4/1995 | (WO) . |
| WO95/15949 | 6/1995 | (WO) . |
| WO96/30018 | 10/1996 | (WO) . |
| WO96/30362 | 10/1996 | (WO) . |
| WO96/30363 | 10/1996 | (WO) . |
| WO96/31477 | 10/1996 | (WO) . |
| WO96/31478 | 10/1996 | (WO) . |
| WO97/23478 | 7/1997 | (WO) . |

COMPOUNDS USEFUL FOR INHIBITION OF FARNESYL PROTEIN TRANSFERASE

REFERENCE TO RELATED APPLICATIONS

This application is a divisional of application Ser. No. 08/927,731 filed Sep. 11, 1997 U.S. Pat. No. 6,030,982, which application in turn claims the benefit of U.S. Provisional Application No. 60/025,249 filed Sep. 13, 1996 and U.S. Provisional Application No. 60/050,009 filed Jun. 17, 1997.

BACKGROUND

WO 95/10516, published Apr. 20, 1995 discloses tricyclic compounds useful for inhibiting farnesyl protein transferase.

In view of the current interest in inhibitors of farnesyl protein transferase, a welcome contribution to the art would be compounds useful for the inhibition of farnesyl protein transferase. Such a contribution is provided by this invention.

SUMMARY OF THE INVENTION

This invention provides compounds useful for the inhibition of farnesyl protein transferase (FPT). The compounds of this invention are represented by the formula:

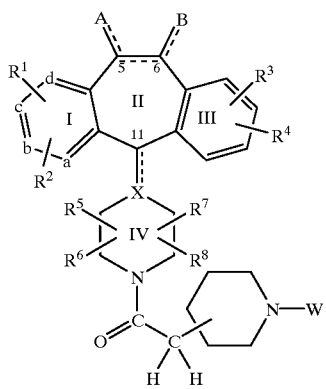

(1.0)

or a pharmaceutically acceptable salt or solvate thereof, wherein: one of a, b, c and d represents N or $NR^9$ wherein $R^9$ is $O^-$, —$CH_3$ or —$(CH_2)_nCO_2H$ wherein n is 1 to 3, and the remaining a, b, c and d groups represent $CR^1$ or $CR^2$; or each of a, b, c, and d are independently selected from $CR^1$ or $CR^2$;

each $R^1$ and each $R^2$ is independently selected from H, halo, —$CF_3$, —$OR^{10}$ (e.g., —$OCH_3$), —$COR^{10}$, —$SR^{10}$ (e.g., —$SCH_3$ and —$SCH_2C_6H_5$), —$S(O)_tR^{11}$ (wherein t is 0, 1 or 2, e.g., —$SOCH_3$ and —$SO_2CH_3$), —$SCN$, —$N(R^{10})_2$, —$NR^{10}R^{11}$, —$NO_2$, —$OC(O)R^{10}$, —$CO_2R^{10}$, —$OCO_2R^{11}$, —$CN$, —$NHC(O)R^{10}$, —$NHSO_2R_{10}$, —$CONHR^{10}$, —$CONHCH_2CH_2OH$, —$NR^{10}COOR^{11}$,

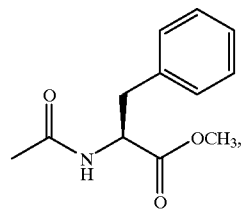

—$SR^{11}C(O)OR^{11}$ (e.g., —$SCH_2CO_2CH_3$), —$SR^{11}N(R^{75})_2$ wherein each $R^{75}$ is independently selected from H and —$C(O)OR^{11}$ (e.g., —$S(CH_2)_2NHC(O)O$-t-butyl and —$S(CH_2)_2NH_2$), benzotriazol-1-yloxy, tetrazol-5-ylthio, or substituted tetrazol-5-ylthio (e.g., alkyl substituted tetrazol-5-ylthio such as 1-methyl-tetrazol-5-ylthio), alkynyl, alkenyl or alkyl, said alkyl or alkenyl group optionally being substituted with halo, —$OR^{10}$ or —$CO_2R^{10}$;

$R^3$ and $R^4$ are the same or different and each independently represents H, any of the substituents of $R^1$ and $R^2$, or $R^3$ and $R^4$ taken together represent a saturated or unsaturated $C_5$–$C_7$ fused ring to the benzene ring (Ring III);

$R^5$, $R^6$, $R^7$ and $R^8$ each independently represents H, —$CF_3$, —$COR^{10}$, alkyl or aryl, said alkyl or aryl optionally being substituted with —$OR^{10}$, —$SR^{10}$, —$S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$, $OPO_3R^{10}$, or $R^5$ is combined with $R^6$ to represent =O or =S and/or $R^7$ is combined with $R^8$ to represent =O or =S;

$R^{10}$ represents H, alkyl, aryl, or aralkyl (e.g., benzyl);

$R^{11}$ represents alkyl or aryl;

X represents N, CH or C, which C may contain an optional double bond (represented by the dotted line) to carbon atom 11;

the dotted line between carbon atoms 5 and 6 represents an optional double bond, such that when a double bond is present, A and B independently represent —$R^{10}$, halo, —$OR^{11}$, —$OCO_2R^{11}$ or —$OC(O)R^{10}$, and when no double bond is present between carbon atoms 5 and 6, A and B each independently represent $H_2$, —$(OR^{11})_2$; H and halo, dihalo, alkyl and H, (alkyl)$_2$, —H and —$OC(O)R^{10}$, H and —$OR^{10}$, =O, aryl and H, =$NOR^{10}$ or —O— $(CH_2)_p$—O— wherein p is 2, 3 or 4; and W represents a group selected from the group consisting of:

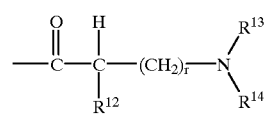

(1)

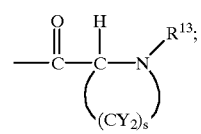

(2)

-continued (3)

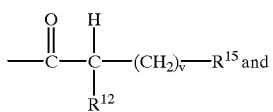

and (4)

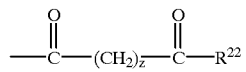

wherein:

$R^{12}$ is selected from the group consisting of: (a) H; (b) alkyl; (c) aralkyl (e.g., benzyl); and (d) heteroarylalkyl (heteroaralkyl) (e.g., —$CH_2$-imidazolyl);

$R^{13}$ and $R^{14}$ are each independently selected from the group consisting of: (a) H; (b) —$C(O)OR^{16}$ wherein $R^{16}$ represents alkyl, aralkyl, and heteroaralkyl; (c) —$SO_2R^{17}$ wherein $R^{17}$ is selected from the group consisting of: —$NH_2$, —$N(alkyl)_2$ wherein each alkyl is the same or different (e.g., —$N(CH_3)_2$), alkyl (e.g., $C_{1-6}$ alkyl, such as methyl), aryl, aralkyl, heteroaryl and heteroaralkyl; (d) —$C(O)R^{18}$ wherein $R^{18}$ is selected from the group consisting of: aryl (e.g., phenyl), alkyl, aralkyl, heteroaryl, and heteroaralkyl; (e) $C_{1-6}$ alkyl; (f) alkaryl; and (g) $C_{3-6}$ cycloalkyl;

r is 0, 1 or 2;

s represents 1, 2, 3, 4, or 5 (preferably 3 or 4), and each Y for each —$CY_2$— group is independently selected from H or —OH, provided that both Y substituents of each —$CY_2$— group are not —OH, and provided that for the —$CY_2$— group alpha to the nitrogen both Y substituents are H, preferably each Y is H such that each —$CY_2$— group is a —$CH_2$— group, such that the group

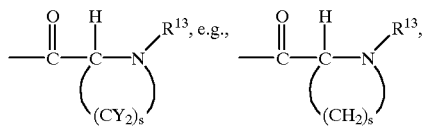

forms a 3, 4, 5, 6, or 7 (preferably 5 or 6) membered ring (e.g., piperidyl or pyrrolidinyl), v is 0, 1 or 2;

$R^{15}$ is selected from the group consisting of:
(a) heteroaryl (e.g., imidazolyl);
(b) a group selected from:

(1)

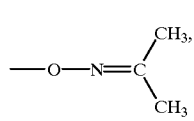

(2)

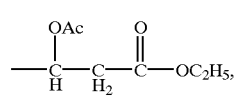

(3)

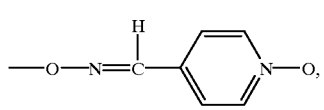

(4)

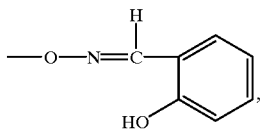

(5) —$CH(OCH_2CH_3)_2$,
(6) —OH, and
(7) —CN; and (c) heterocycloalkyl selected from the group consisting of:

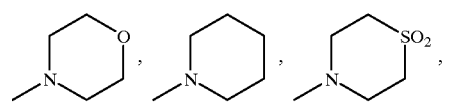

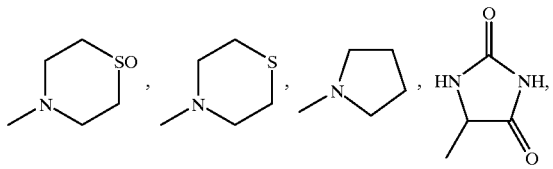

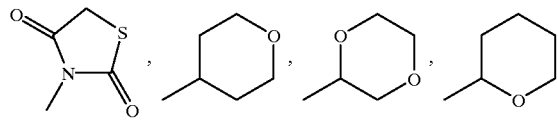

and

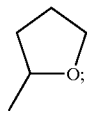

z is 0, 1, 2, 3, 4, or 5 wherein each —$CH_2$— group is optionally substituted with a —OH group, i.e., each H of each —$CH_2$— group can optionally be replaced with a —OH group and the optional substitution on each —$CH_2$— group is independent of the substitution on any other —$CH_2$— group, generally each —$CH_2$— is unsubstituted;

$R^{22}$ represents a group selected from:

(1)

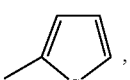

(2)

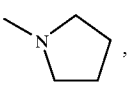

(3)

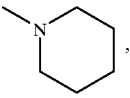

-continued (4)

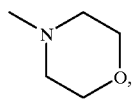

(5) alkyl (e.g., —CH₃),
(6) —OR²³ wherein R²³ is selected from the group consisting of: alky, aryl and H, and (7)

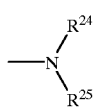

wherein $R^{24}$ and $R^{25}$ are independently selected from the group consisting of: —NH₂, alkoxy (e.g., —OCH₃), —OH, —CH₂CO₂H, —OCH₂Ph (i.e., —OCH₂C₆H₅), —CH(OCH₃)CH(CH₃)₂

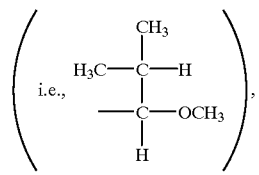

alkyl, aryl, H, aralkyl, and heteroaralkyl; or $R^{24}$ and $R^{25}$ taken together form a carbon chain having 4 or 5 (—CH₂—) groups such that $R^{24}$ and $R^{25}$ taken together with the nitrogen to which they are bound form a 5 or 6 membered heterocycloalkyl ring.

The compounds of this invention: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

The compounds of this invention inhibit farnesyl protein transferase and the farnesylation of the oncogene protein Ras. Thus, this invention further provides a method of inhibiting farnesyl protein transferase, (e.g., ras farnesyl protein transferase) in mammals, especially humans, by the administration of an effective amount of the tricyclic compounds described above. The administration of the compounds of this invention to patients, to inhibit farnesyl protein transferase, is useful in the treatment of the cancers described below.

This invention provides a method for inhibiting or treating the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention also provides a method for inhibiting or treating tumor growth by administering an effective amount of the tricyclic compounds, described herein, to a mammal (e.g., a human) in need of such treatment. In particular, this invention provides a method for inhibiting or treating the growth of tumors expressing an activated Ras oncogene by the administration of an effective amount of the above described compounds. Examples of tumors which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma, epidermal carcinoma, breast cancer and prostate cancer.

It is believed that this invention also provides a method for inhibiting or treating proliferative diseases, both benign and malignant, wherein Ras proteins are aberrantly activated as a result of oncogenic mutation in other genes—i.e., the Ras gene itself is not activated by mutation to an oncogenic form—with said inhibition or treatment being accomplished by the administration of an effective amount of the tricyclic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited or treated by the tricyclic compounds described herein.

The tricyclic compounds useful in the methods of this invention inhibit or treat the abnormal growth of cells. Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

DETAILED DESCRIPTION OF THE INVENTION

As used herein, the following terms are used as defined below unless otherwise indicated:

Ac-represents acetyl;

MH⁺-represents the molecular ion plus hydrogen of the molecule in the mass spectrum;

M⁺-represents the molecular ion of the molecule in the mass spectrum;

benzotriazol-1-yloxy represents

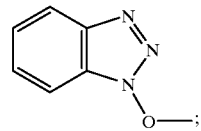

1-methyl-tetrazol-5-ylthio represents

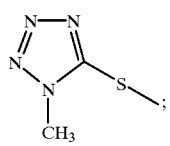

alkenyl-represents straight and branched carbon chains having at least one carbon to carbon double bond and containing from 2 to 12 carbon atoms, preferably from 2 to 6 carbon atoms and most preferably from 3 to 6 carbon atoms;

alkynyl-represents straight and branched carbon chains having at least one carbon to carbon triple bond and containing from 2 to 12 carbon atoms, preferably from 2 to 6 carbon atoms;

alkyl-(including the alkyl portions of aralkyl and heteroarylalkyl)-represents straight and branched carbon chains and contains from one to twenty carbon atoms, preferably one to six carbon atoms;

aralkyl-represents an aryl group, as defined below, bound to an alkyl group, as defined above, preferably the alkyl group is —CH$_2$—, (e.g., benzyl);

aryl (including the aryl portion of aralkyl and aralkyl)-represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted (e.g., 1 to 3) with one or more of halo, alkyl, hydroxy, alkoxy, phenoxy, CF$_3$, amino, alkylamino, dialkylamino, —COOR$^{10}$ or —NO$_2$;

BOC-represents —C(O)OC(CH$_3$)$_3$;

—CH$_2$-imidazolyl represents an imidazolyl group bound by any substitutable carbon of the imidazole ring to a —CH$_2$—, that is:

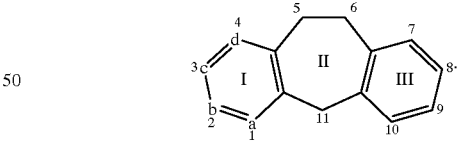

such as —CH$_2$—(2-, 4- or 5-)imidazolyl, for example

Et-represents ethyl;

halo-represents fluoro, chloro, bromo and iodo;

heteroaryl-represents cyclic groups, optionally substituted with R$^3$, R$^4$, phenyl, and or —CH$_2$C(O)OCH$_3$, said cyclic groups having at least one heteroatom selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms, e.g., (2-, 4- or 5-)imidazolyl, triazolyl,

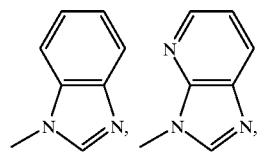

2-, 3- or 4-pyridyl or pyridyl N-oxide (optionally substituted with R$^3$ and R$^4$), wherein pyridyl N-oxide can be represented as:

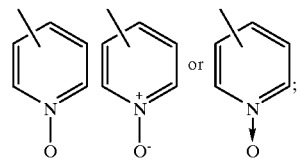

heteroarylalkyl (heteroaralkyl)-represents a heteroaryl group, as defined above, bound to an alkyl group, as defined above, preferably the alkyl group is —CH$_2$— (e.g., —CH$_2$—(4- or 5-)imidazolyl);

heterocycloalkyl-represents a saturated, branched or unbranched carbocylic ring containing from 3 to 15 carbon atoms, preferably from 4 to 6 carbon atoms, which carbocyclic ring is interrupted by 1 to 3 hetero groups selected from —O—, —S— or —NR$^{10}$—, suitable heterocycloalkyl groups include: (1) 2- or 3-tetrahydrofuranyl, (2) 2- or 3-tetrahydrothienyl, (3) 2-, 3- or 4-piperidinyl, (4) 2- or 3-pyrrolidinyl, (5) 2- or 3-piperizinyl, and (6) 2- or 4-dioxanyl; and Ph-represents phenyl The following solvents and reagents are referred to herein by the abbreviations indicated: tetrahydrofuran (THF); isopropanol (iPrOH); ethanol (EtOH); methanol (MeOH); acetic acid (HOAc or AcOH); ethyl acetate (EtOAc); N,N-dimethylformamide (DMF); trifluoroacetic acid (TFA); trifluoro-acetic anhydride (TFAA); 1-hydroxybenzotriazole (HOBT); 1-(3-dimethylaminopropyl)-3-ethyl carbodiimide hydrochloride (DEC); diisobutylaluminum hydride (DIBAL); and 4-methylmorpholine (NMM).

Reference to the position of the substituents R$^1$, R$^2$, R$^3$, and R$^4$ is based on the numbered ring structure:

Those skilled in the art will also appreciate that the S and R stereochemistry at the C-11 bond are:

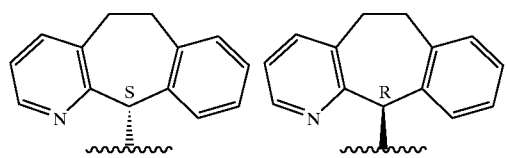

Compounds of Formula 1.0 include compounds wherein the bottom piperidinyl group is a 4- or 3-piperidinyl group, i.e.,

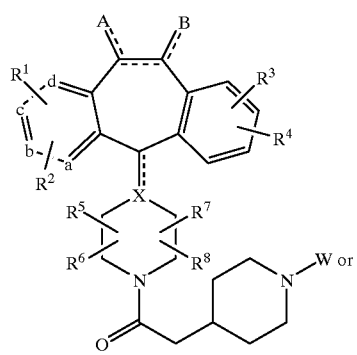

(1.1)

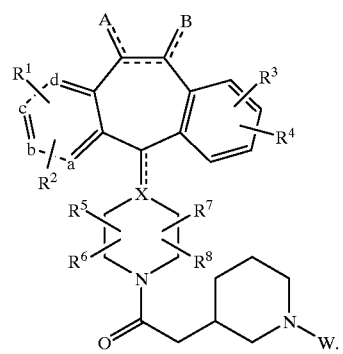

(1.1A)

Compounds of Formula 1.0 include compounds wherein $R^2$ and $R^4$ are H, and $R^1$ and $R^3$ are halo (preferably independently selected from Br or Cl). For example, $R^1$ is Br and $R^3$ is Cl. These compounds include compounds wherein $R^1$ is in the 3-position and $R^3$ is in the 8-position, e.g., 3-Br and 8-Cl. Compounds of Formula 1.0 also include compounds wherein $R^2$ is H, and $R^1$, $R^3$ and $R^4$ are halo (preferably independently selected from Br or Cl).

Preferably, compounds of Formula 1.0 are represented by compounds of Formula 1.1:

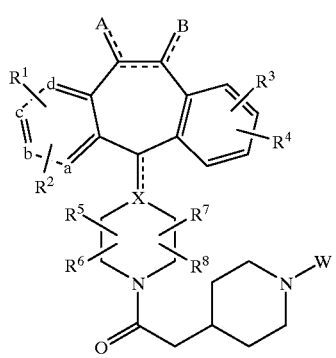

(1.1)

wherein all substituents are as defined for Formula 1.0.

Preferably, $R^2$ is H and $R^1$, $R^3$ and $R^4$ are halo; a is N and b, c and d are carbon; A and B are each $H_2$; the optional bond between C5 and C6 is absent; X is CH; and $R^5$, $R^6$, $R^7$ and $R^8$ are H. More preferably, $R^1$, $R^3$ and $R^4$ are independently selected from Br or Cl. Most preferably, $R^1$ is Br, and $R^3$ and $R^4$ are independently selected from Cl and Br.

More preferably, compounds of Formula 1.0 are represented by compounds of Formula 1.2 and Formula 1.3:

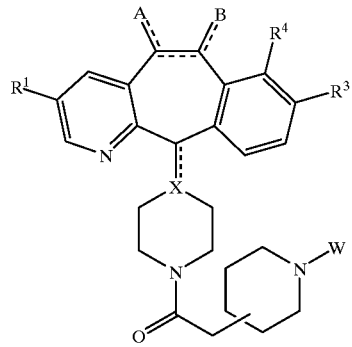

(1.2)

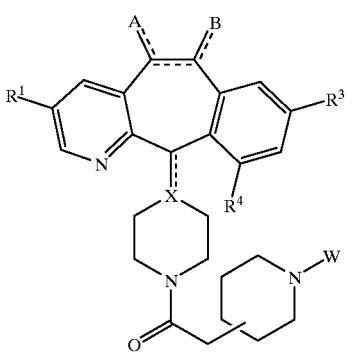

(1.3)

and most preferably, compounds of Formulas 1.4 and 1.5

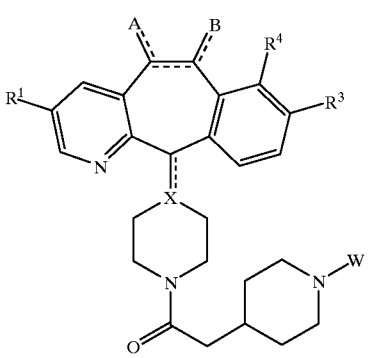

(1.4)

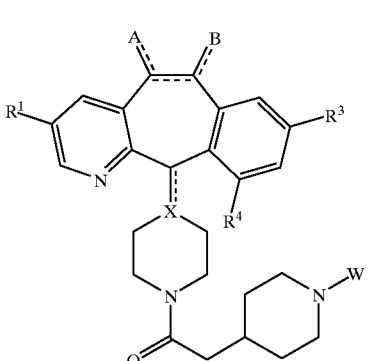

(1.5)

wherein $R^1$, $R^3$ and $R^4$ are each independently selected from halo, preferably, Br or Cl; and A, B, X and W are as defined for Formula 1.0. More preferably, A and B are each $H_2$; the optional bond between C5 and C6 is absent; and X is CH.

Most preferably, $R^1$ is Br; $R^3$ and $R^4$ are independently Br or Cl, and still more preferably $R^3$ is Cl and $R^4$ is Br; A and B are each $H_2$; the optional bond between C5 and C6 is absent; X is CH; and $R^5$, $R^6$, $R^7$ and $R^8$ are H.

Examples of $R^{15}$ include:

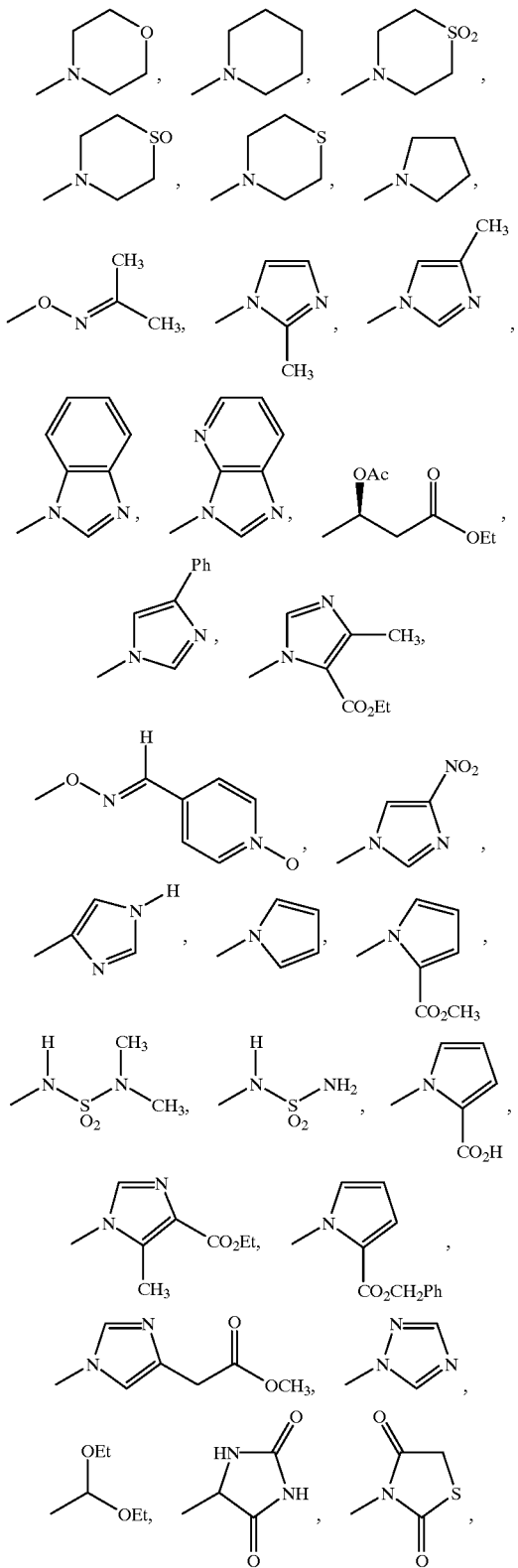

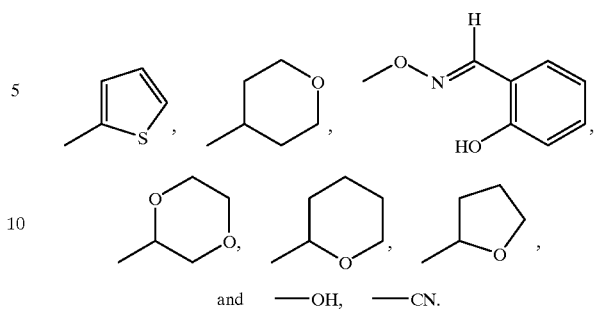

and —OH, —CN.

When W represents:

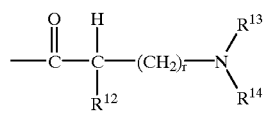

and r is 0: (1) preferably, $R^{12}$ is selected from the group consisting of: (a) H; (b) alkyl; (c) aralkyl; and (d) heteroaralkyl; and most preferably, $R^{12}$ is selected from the group consisting of: (a) H, (b) methyl, (c) —$CH_2$-imidazolyl and (d) benzyl; (2) preferably, $R^{13}$ and $R^{14}$ are independently selected from the group consisting of: (a) H; (b) —C(O)O$R^{16}$ wherein $R^{16}$ is alkyl; (c) —$SO_2R^{17}$ wherein $R^{17}$ is alkyl or aryl; (d) —C(O)$R^{18}$ wherein $R^{18}$ is aryl; and (e) alkyl; and most preferably, $R^{13}$ and $R^{14}$ are independently selected from the group consisting of: (a) H, (b) —C(O)OC($CH_3)_3$, (c) —$SO_2CH_3$ and (d) —C(O)-phenyl. Preferably, when one of $R^{13}$ or $R^{14}$ is —C(O)O$R^{16}$, —$SO_2R^{17}$, —C(O)$R^{18}$, alkaryl or cycloalkyl, the remaining $R^{13}$ or $R^{14}$ is H. Preferred combinations of substituent groups include: (1) $R^{12}$ being alkyl (more preferred, methyl), $R^{13}$ being —C(O)O$R^{16}$ (more preferred —C(O)OC($CH_3)_3$) and $R^{14}$ being H; (2) $R^{12}$ being heteroarylalkyl (more preferred —$CH_2$—(4 or 5)-imidazolyl), $R^{13}$ being H or —C(O)O$R^{16}$ (more preferred H or —C(O)OC($CH_3)_3$) and $R^{14}$ being H; (3) $R^{12}$ being aralkyl (more preferred benzyl), $R^{13}$ being —C(O)O$R^{16}$ (more preferred —C(O)OC($CH_3)_3$) and $R^{14}$ being H; (4) $R^{12}$ being H, $R^{13}$ being —C(O)O$R^{16}$ (more preferred —C(O)OC($CH_3)_3$) and $R^{14}$ being H; (5) $R^{12}$ being H, $R^{13}$ being —$SO_2R^{17}$ (more preferred —$SO_2CH_3$) and $R^{14}$ being H; and (6) $R^{12}$ being H, $R^{13}$ being —C(O)$R^{18}$ (more preferred —C(O)-phenyl) and $R^{14}$ being H.

Those skilled in the art will appreciate that the W substituent described in the previous paragraph can be derived from known amino acids having one carboxyl and amino group. Examples of such amino acids include but are not limited to glycine, alanine, phenylalanine, asparagine and histidine. For example, see Morrison and Boyd, Organic Chemistry, Fifth Edition, Allyn and Bacon, Inc., Boston, pages 1346–1347, the disclosure of which is incorporated herein by reference thereto.

When W represents

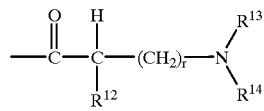

and r is 1 or 2, preferably $R^{12}$ is H, and $R^{13}$ and $R^{14}$ are independently selected from alkyl, most preferably, $R^{13}$ and $R^{14}$ are the same alkyl group (e.g., methyl).

When W represents

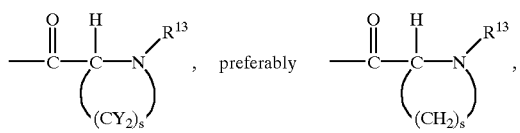

s is preferably 3, such that a pyrrolidone ring is formed, and $R^{13}$ is preferably H or —C(O)$OR^{16}$ wherein $R^{16}$ is alkyl; most preferably, $R^{13}$ is H or —C(O)OC(CH$_3$)$_3$.

When W represents:

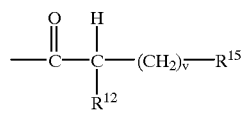

and v is 0, preferably $R^{12}$ represents H and $R^{15}$ represents heteroaryl or heterocycloalkyl. Most preferably, when $R^{15}$ is heteroaryl said heteroaryl is imidazolyl

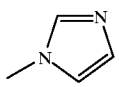

and when $R^{15}$ is heterocycloalkyl said heterocycloalkyl is

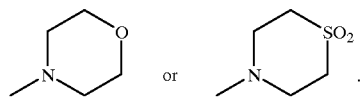

When W represents:

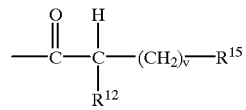

and v is 1 or 2, preferably $R^{12}$ represents H and $R^{15}$ is heterocycloalkyl. Most preferably $R^{12}$ represents H and $R^{15}$ is heterocycloalkyl, e.g.,

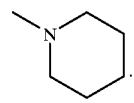

When W represents

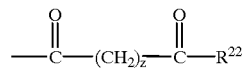

and z is 0, preferably $R^{22}$ represents

and $R^{24}$ and $R^{25}$ preferably represent H.
When W represents

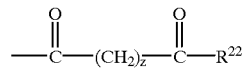

and z is 1, 2, 3, 4 or 5, $R^{22}$ preferably represents —$OR^{23}$ and $R^{23}$ preferably represents alkyl and most preferably methyl.

Compounds of Formulas 1.2A and 1.3A:

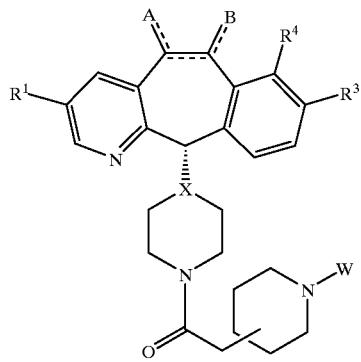

(1.2A)

-continued (1.3A)

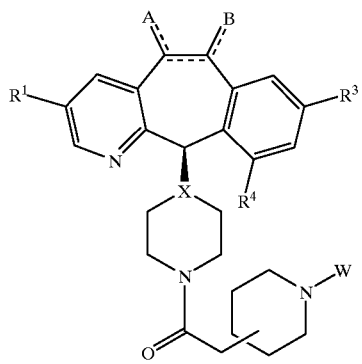

are preferred when X is CH or N, and $R^1$, $R^3$ and $R^4$ are halo.

The preferred compounds of this invention are represented by the compounds of Formulas:

(1.4A)

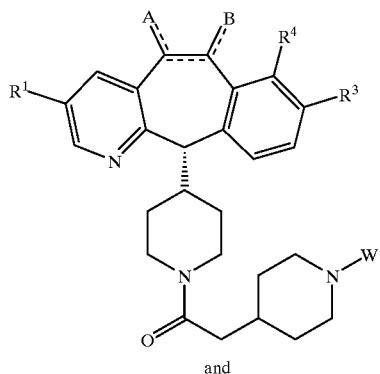

and (1.5A)

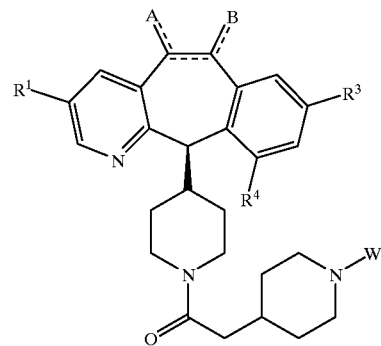

wherein $R^1$, $R^3$ and $R^4$ are halo and the remaining substituents are as defined above, with the compounds of Formula 1.5A being more preferred.

Those skilled in the art will appreciate that W substituent:

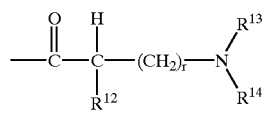

wherein r is 0 includes

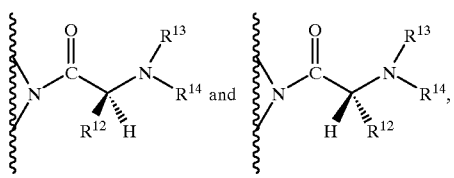

and W substituent:

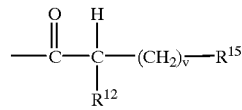

wherein V is 0 includes

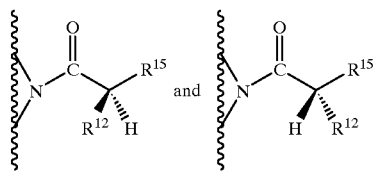

Representative compounds of Formula 1.0 wherein W is

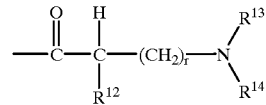

and r is 0 include:

(2.0)

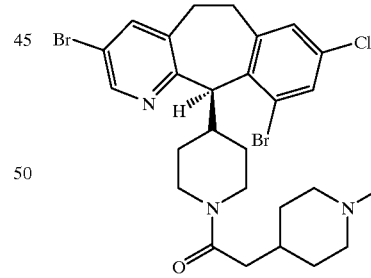

(3.0)

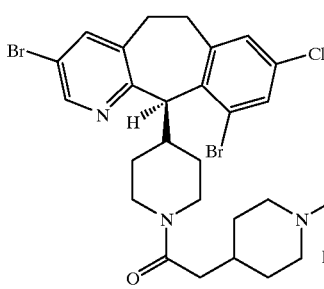

-continued
(4.0)
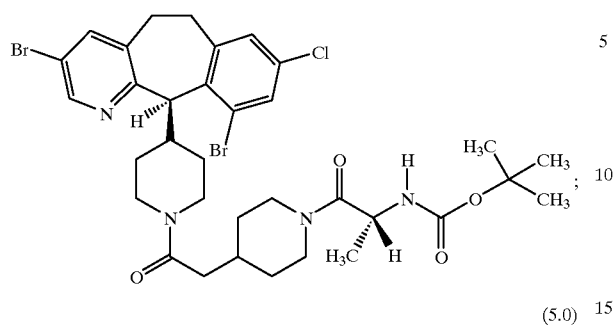
(5.0)
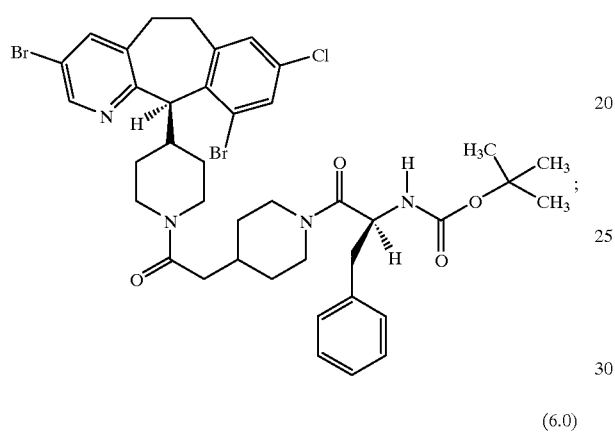
(6.0)
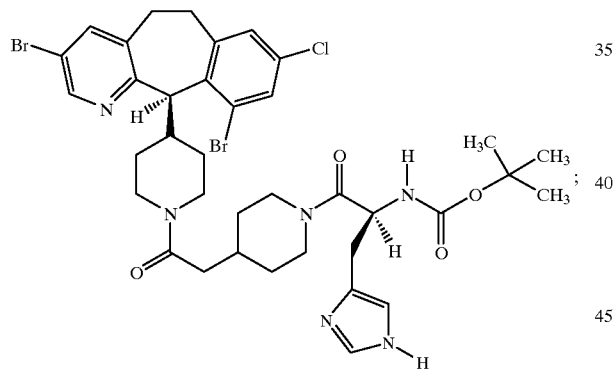
(8.0)
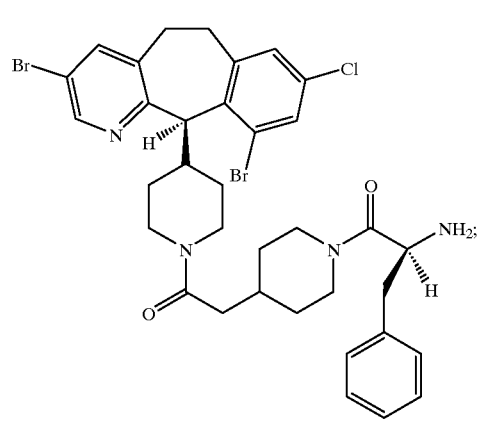
-continued
(9.0)
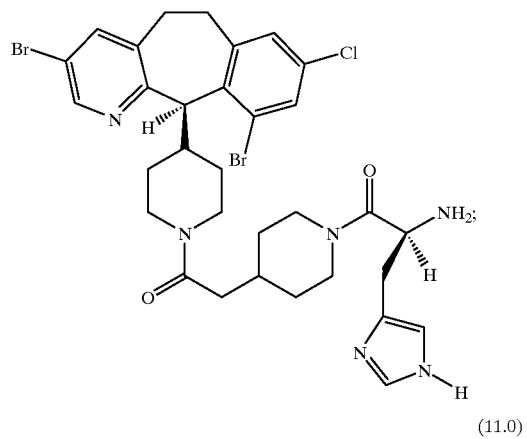
(11.0)
(12.0)
and
(12.1)
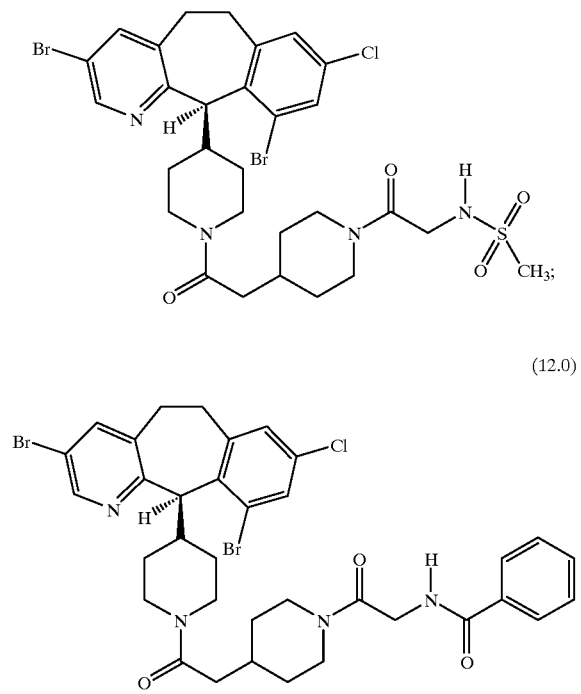

Representative compounds of Formula 1.0 wherein W is
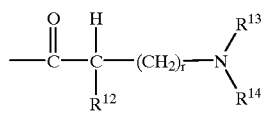
and r is 1 or 2 include:
(12.2)
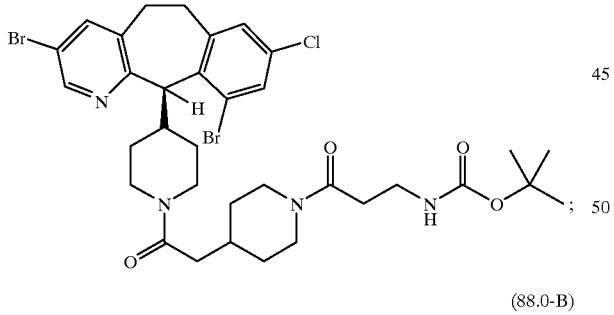
(12.3)
(86.0-B)
(88.0-B)
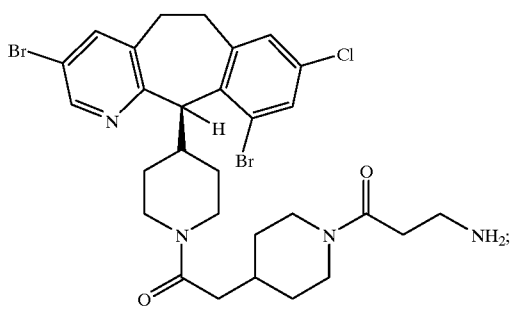
(89.0-B)
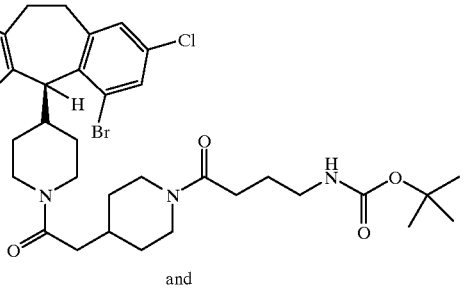
and
(90.0-B)
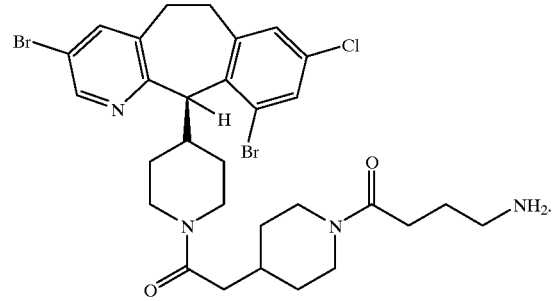
Representative compounds of Formula 1.0 wherein W is
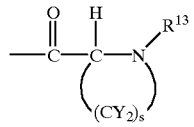
and s is 3 include:
(7.0)
(10.0)
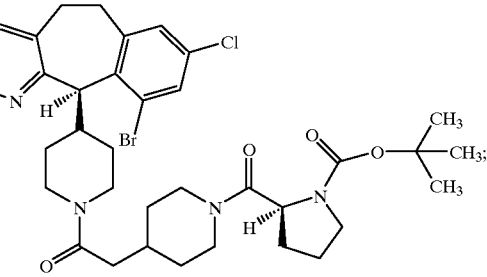

-continued
(24.0-B)
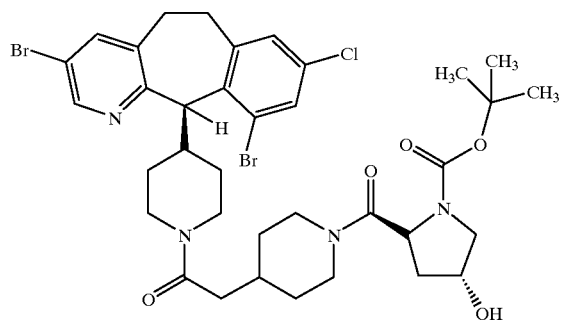
and
(63.0-B)
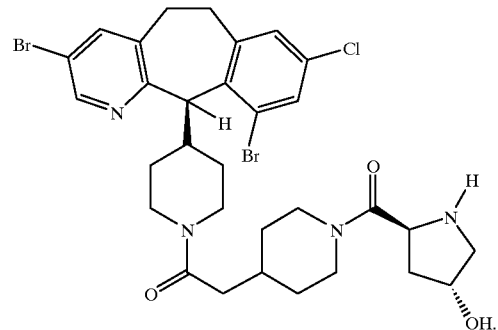
Representative compounds of Formula 1.0 wherein W is
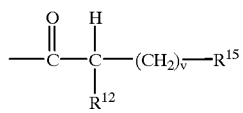
and v is 0 include:
(13.0)
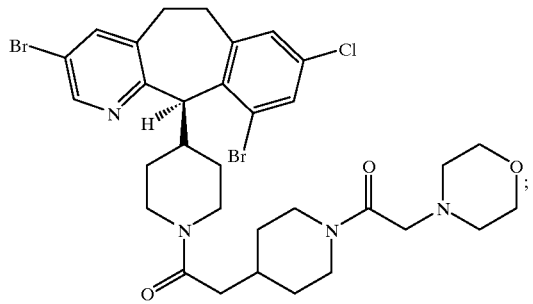
-continued
(14.0)
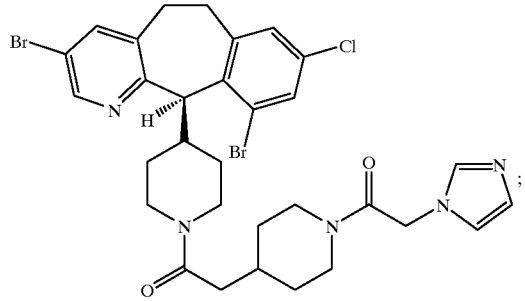
(14.1)
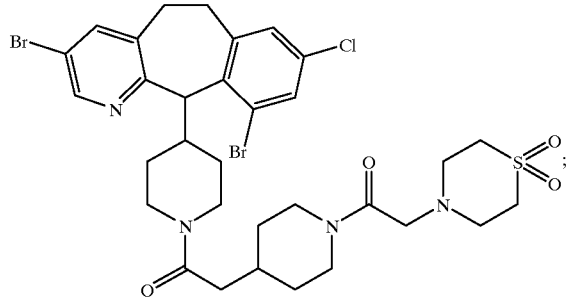
(6.0-B)
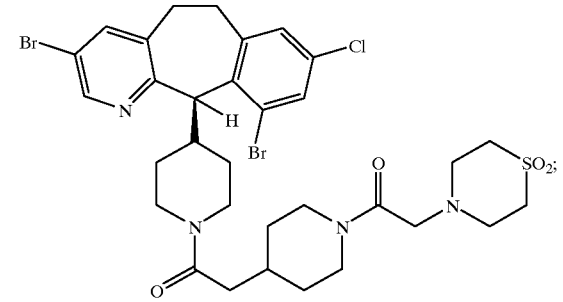
(9.0-B)
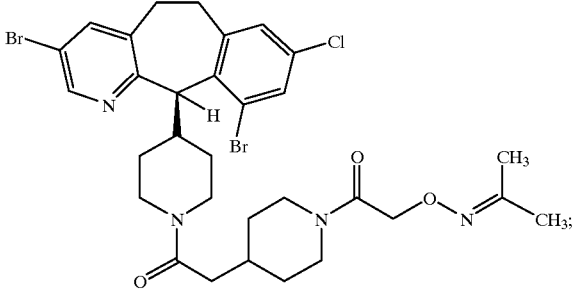
(10.0-B)
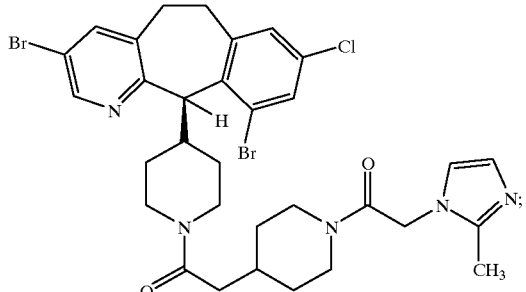

-continued
(11.0-B)
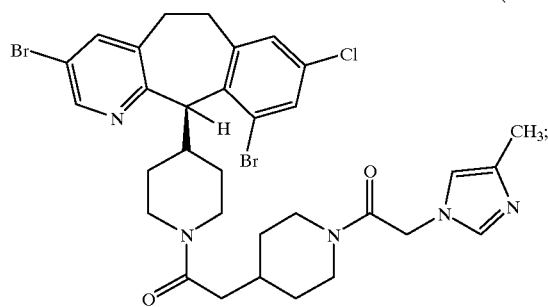
(12.0-B)
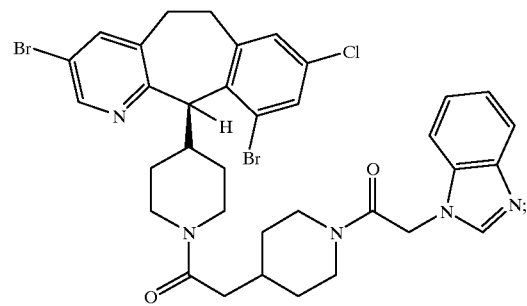
(13.0-B)
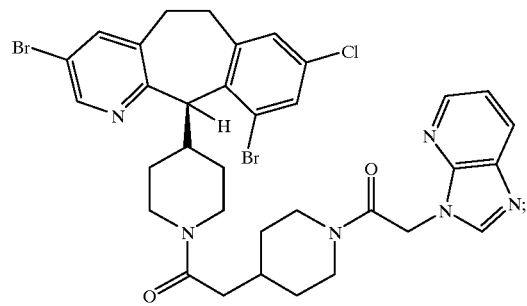
(16.0-B)
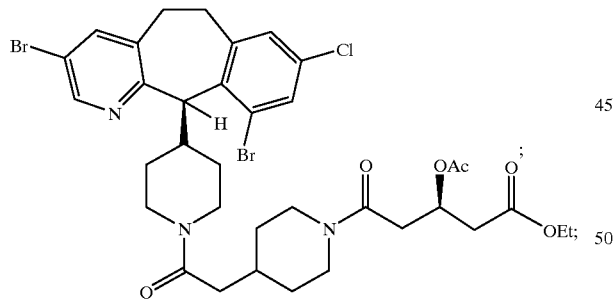
Ac = acetyl
(20.0-B)
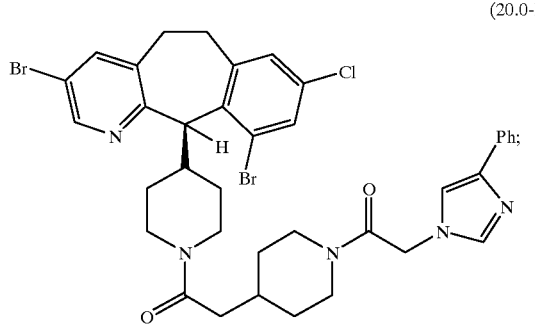
-continued
(21.0-B)
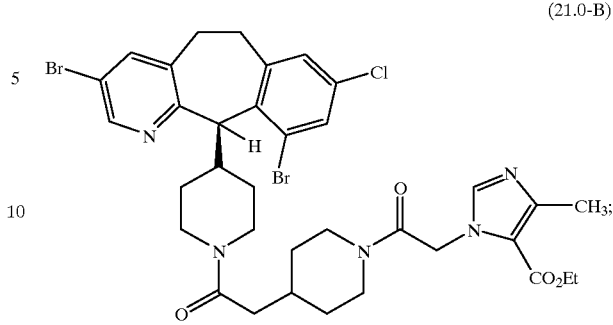
(22.0-B)
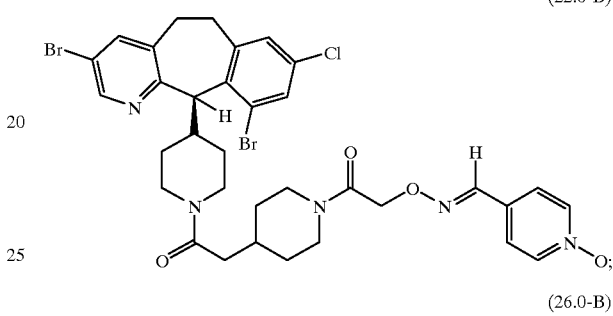
(26.0-B)
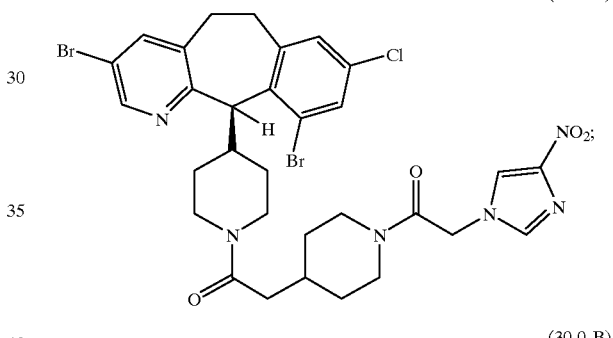
(30.0-B)
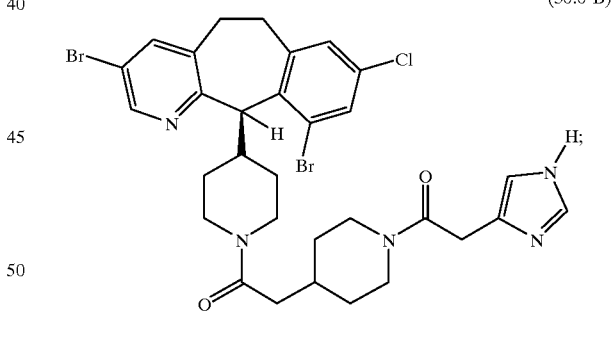
(34.0-B)
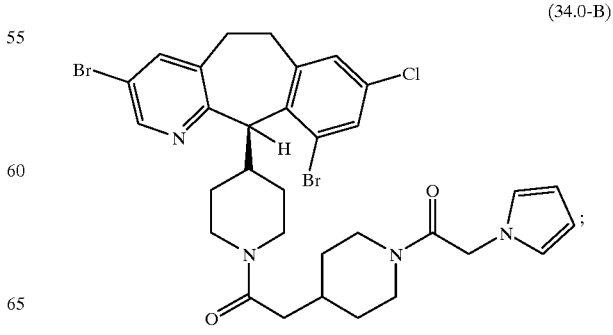

25
-continued
(35.0-B)
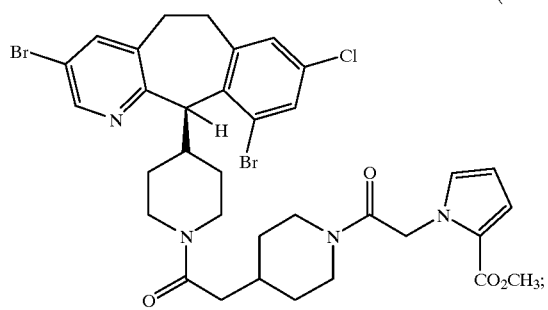
(37.0-B)
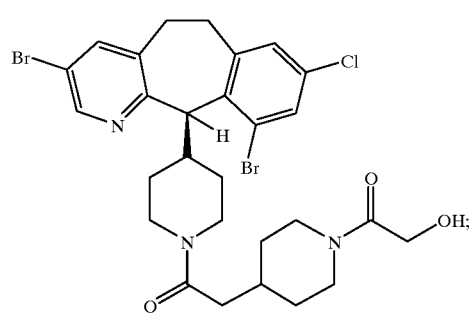
(38.0-B)
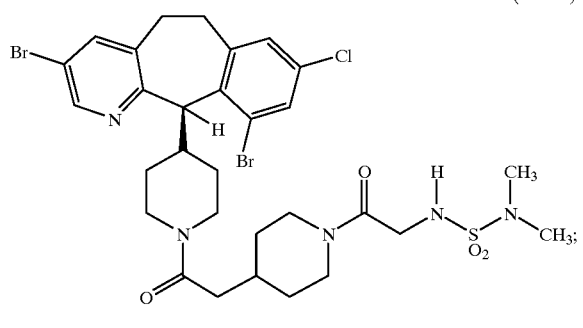
(39.0-B)
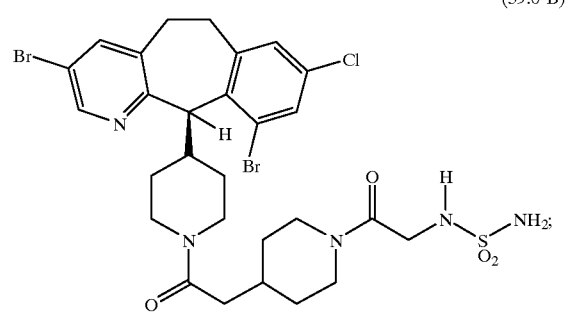
(44.0-B)
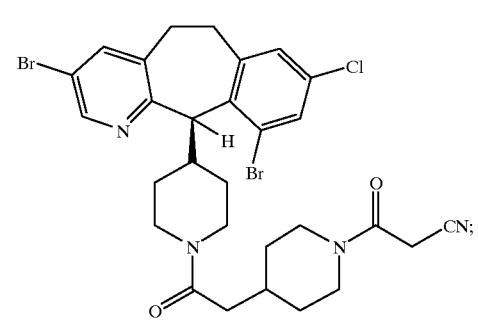
26
-continued
(52.0-B)
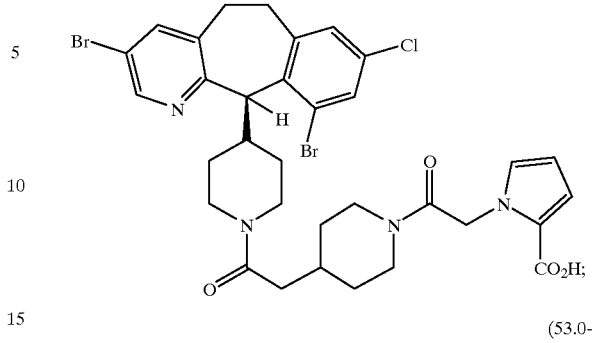
(53.0-B)
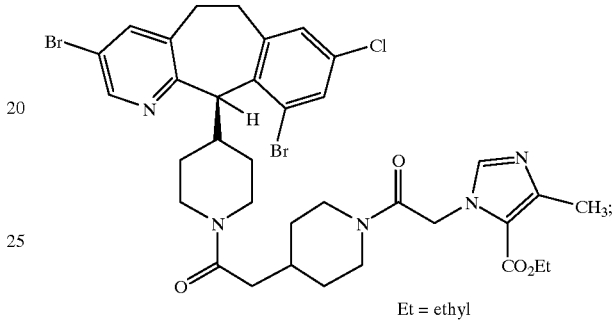
Et = ethyl
(54.0-B)
Br
Cl
Br
N
H
N
N
O
N
CO₂Et
CH₃
(55.0-B)
Br
Cl
Br
N
H
N
N
O
N
CO₂CH₂Ph;
Ph = phenyl
(56.0-B)
Br
Cl
Br
N
H
N
N
O
N
N
O
OCH₃

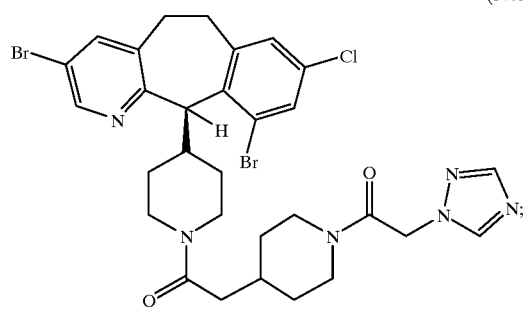
(57.0-B)
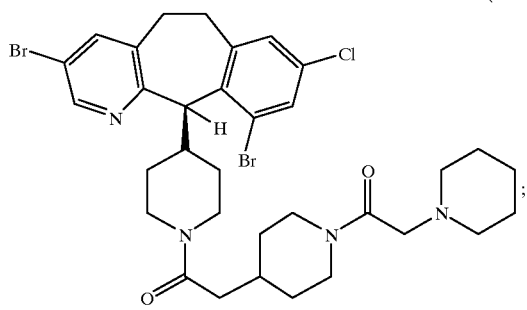
(75.0-B)
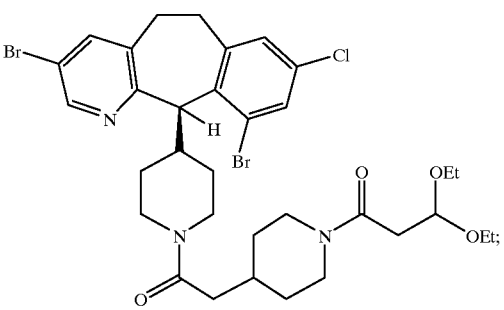
(76.0-B)
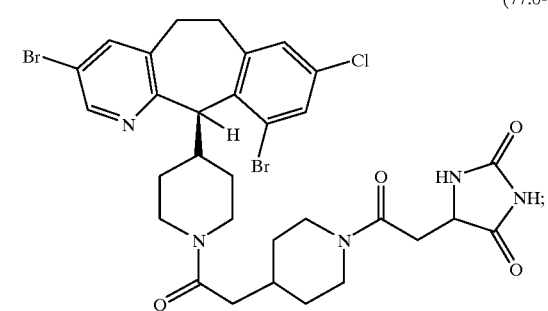
(77.0-B)
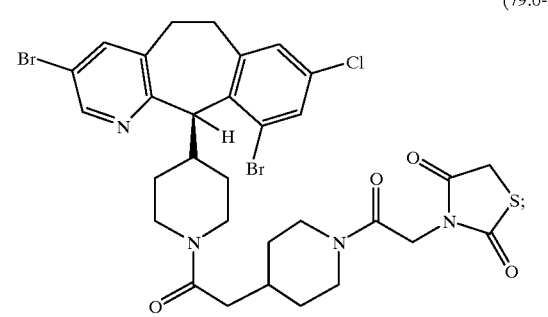
(79.0-B)
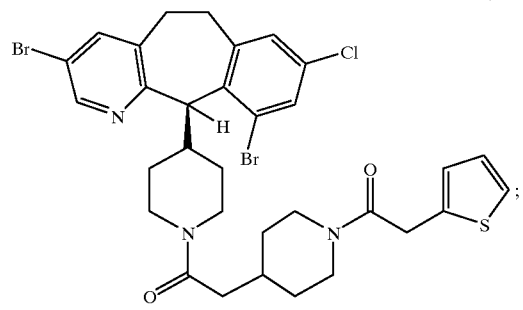
(82.0-B)
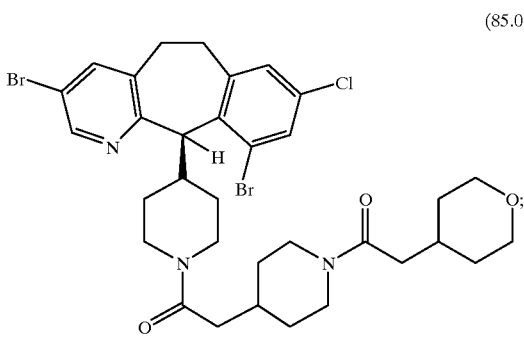
(85.0-B)
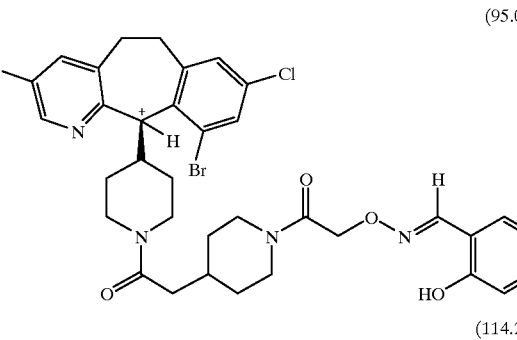
(95.0-B)
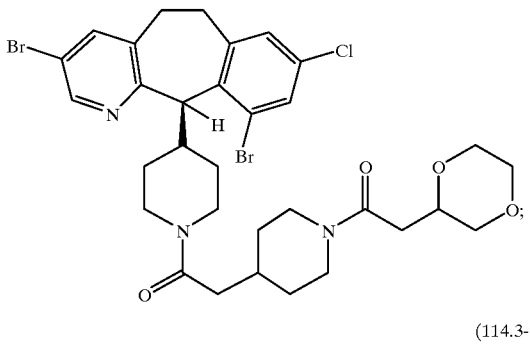
(114.2-B)
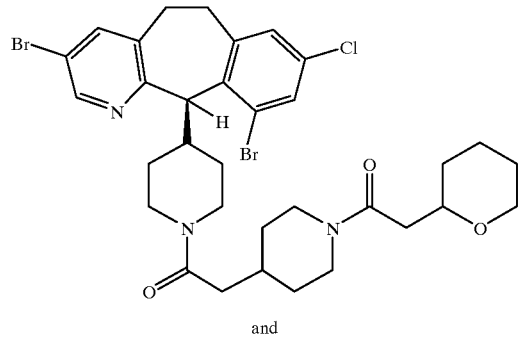
(114.3-B)
and -continued
(114.4-B)
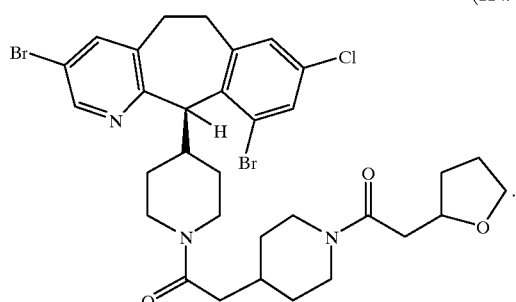
Representative compounds of Formula 1.0 wherein W is
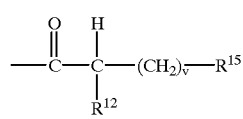
and v is 1 include:
(14.2)
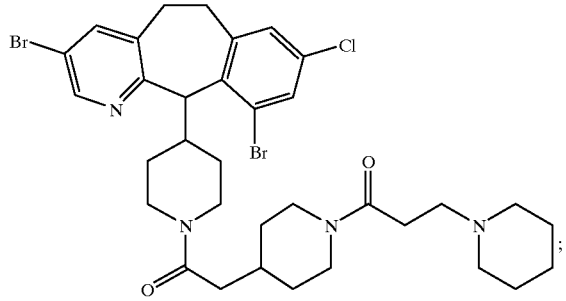
(7.0-B)
(23.0-B)
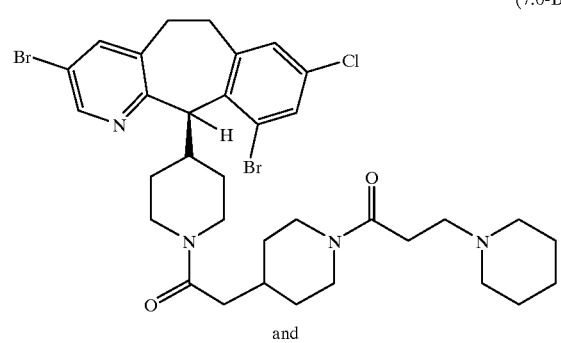
and
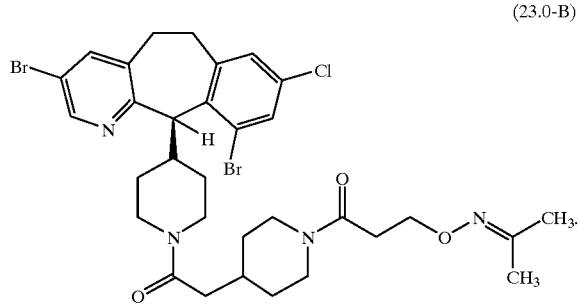
Compounds of Formula 1.0 wherein W is
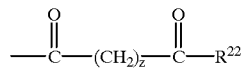
and z is 0 include:
(15.0)
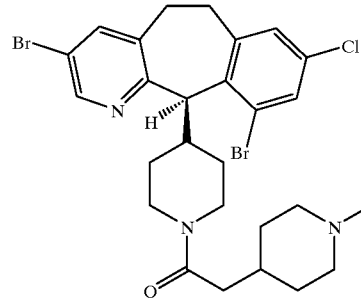
(17.0-B)
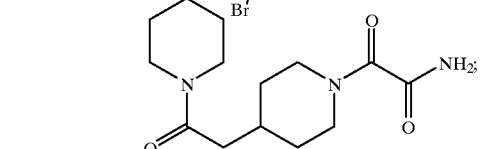
(32.0-B)
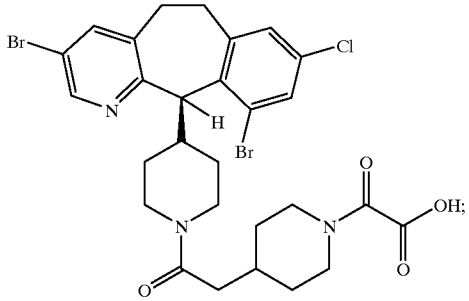
(33.0-B)
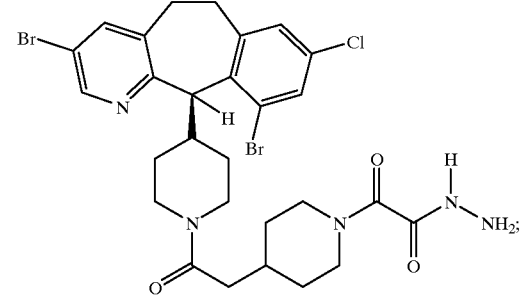
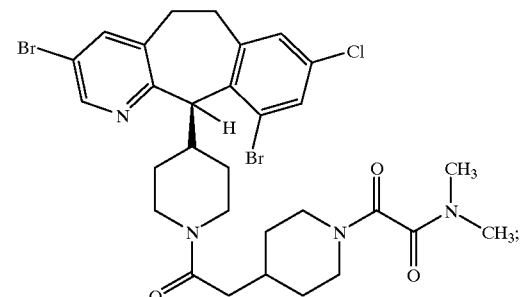

(49.0-B)
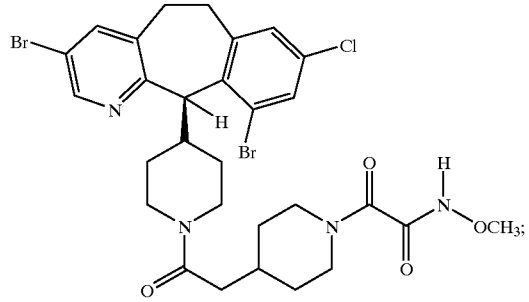
(58.0-B)
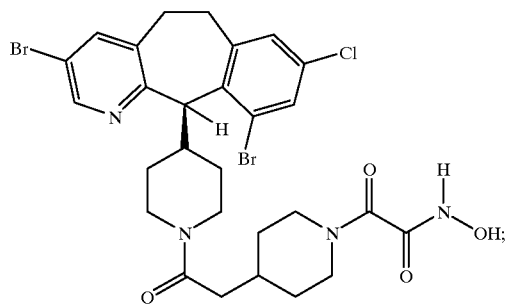
(59.0-B)
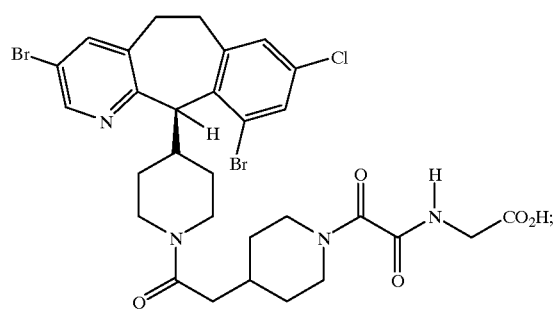
(60.0-B)
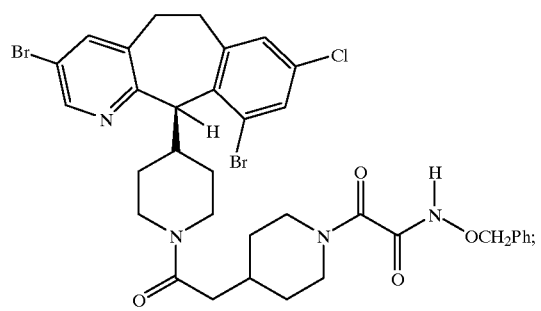
(64.0-B)
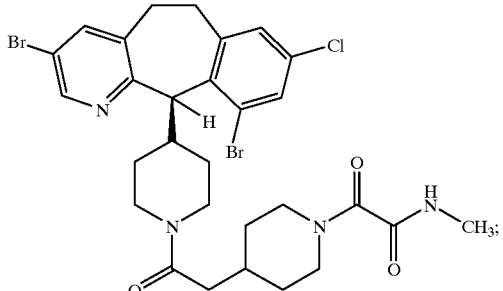
(72.0-B)
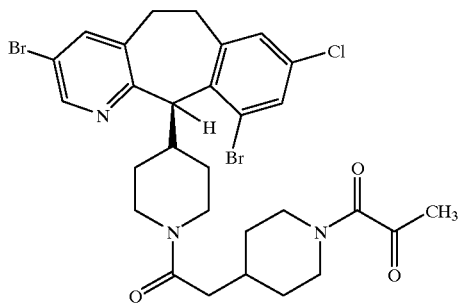
(81.0-B)
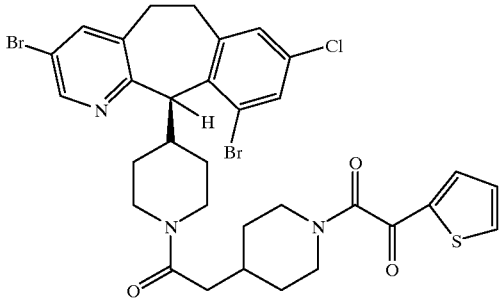
and
(104.0-B)
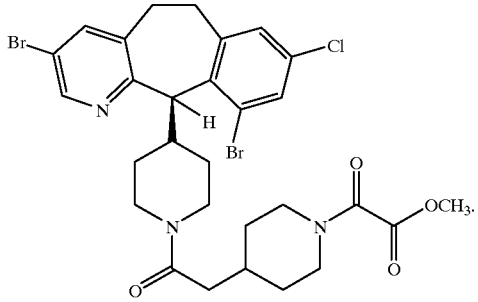
Compounds of Formula 1.0 wherein W is
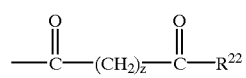

and z is 1, 2, 3, 4 or 5 include:
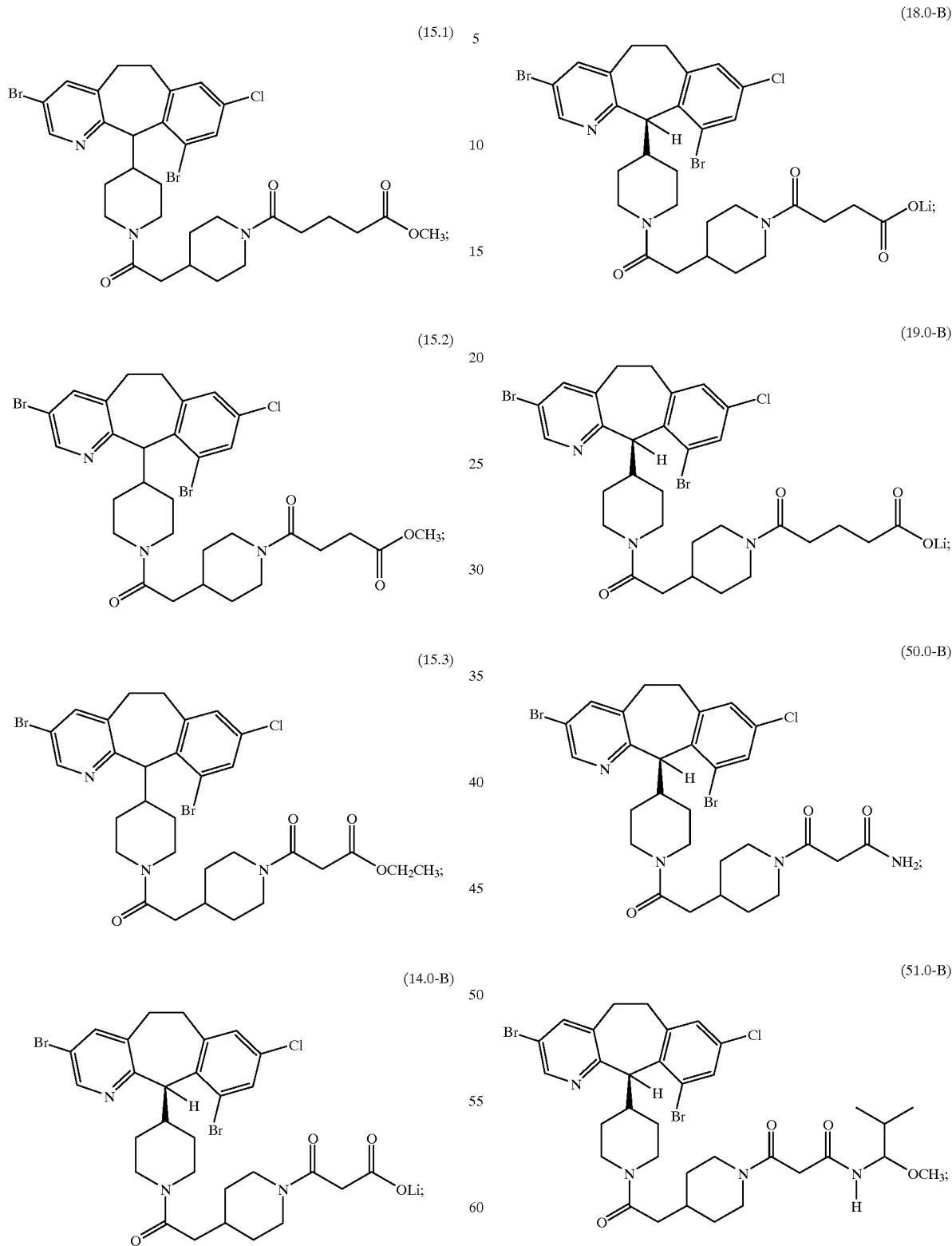

(67.0-B)
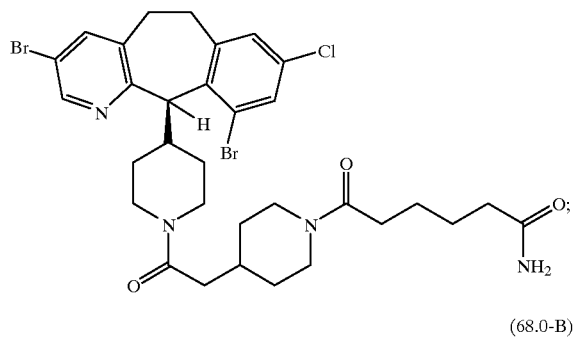
(74.0-B)
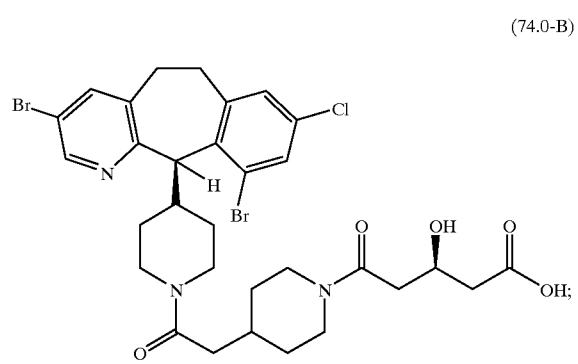
(68.0-B)
(92.0-B)
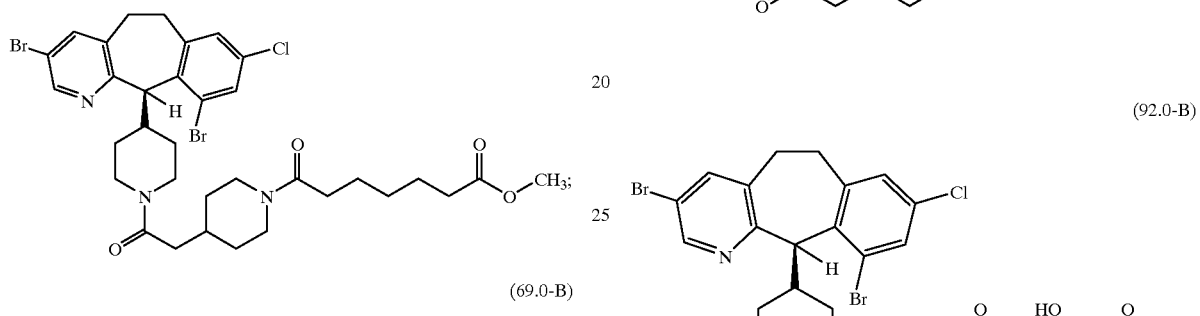
(69.0-B)
(101.0-B)
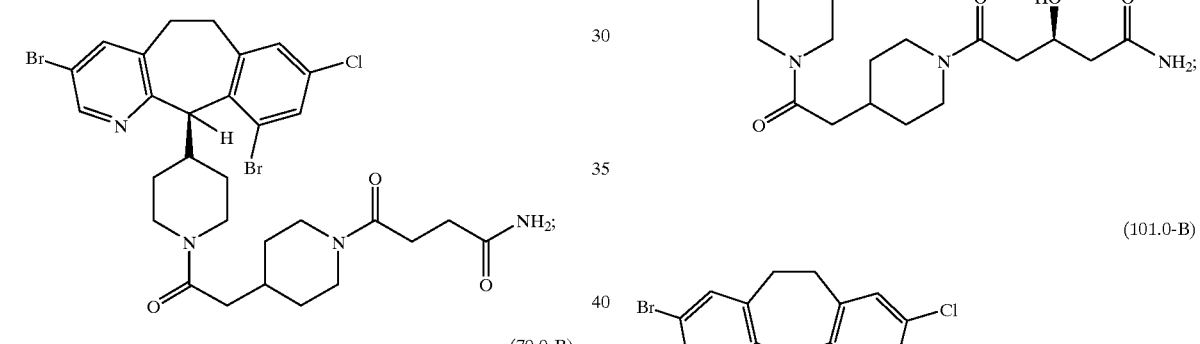
(70.0-B)
(107.0-B)
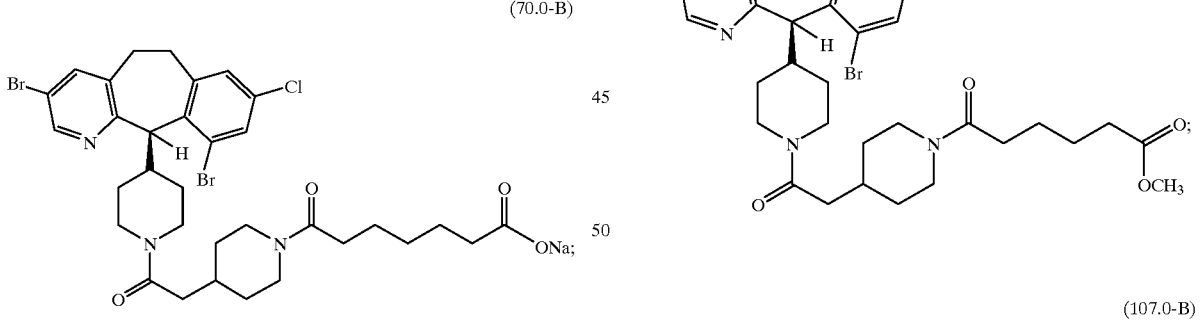
(71.0-B)
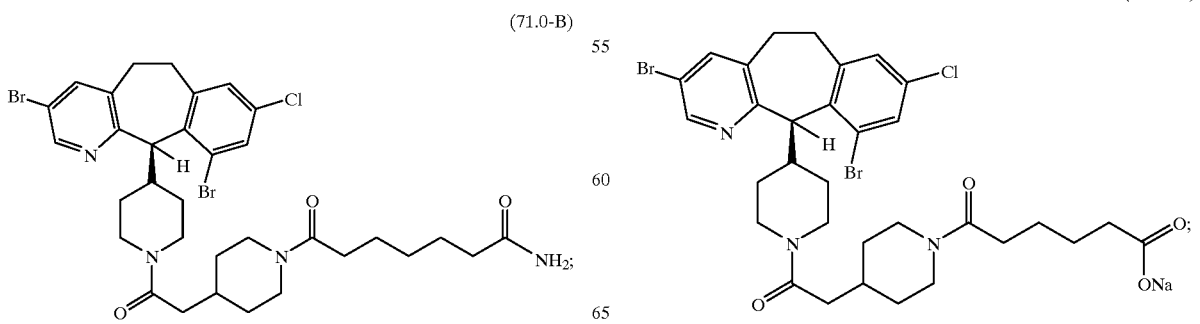

(108.0-B)
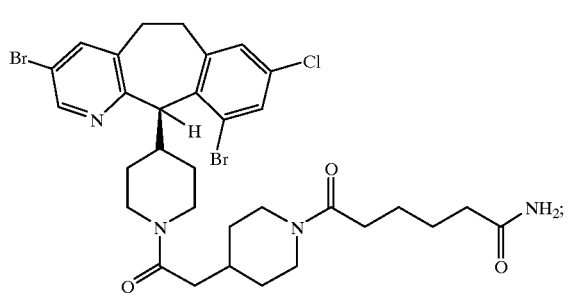
(109.0-B)
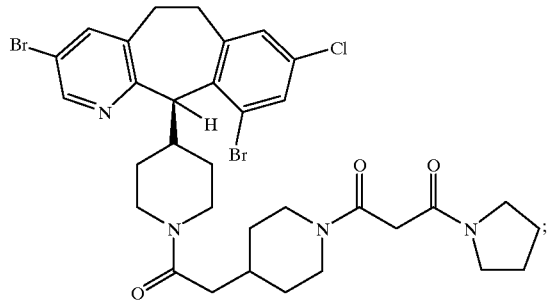
(110.0-B)
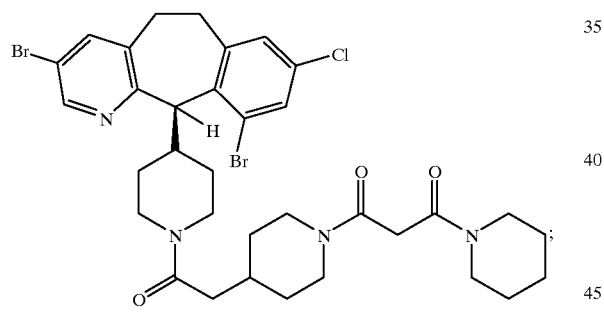
(111.0-B)
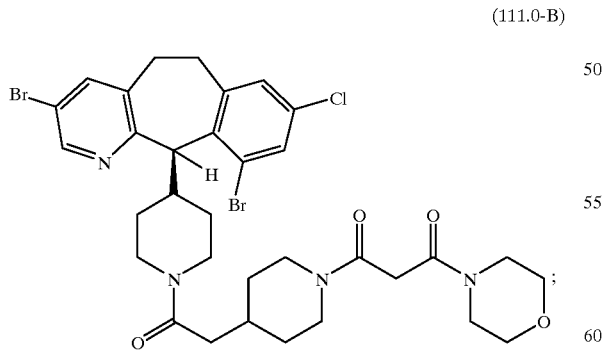
(112.0-B)
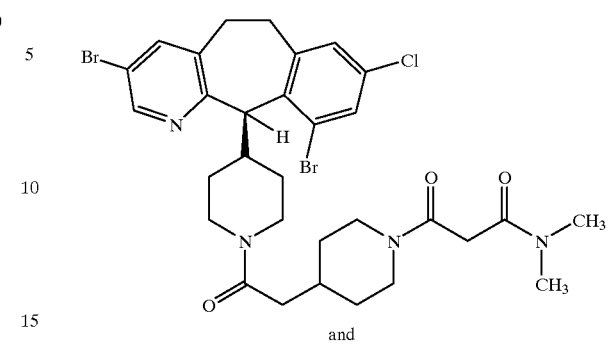
and
(114.0-B)
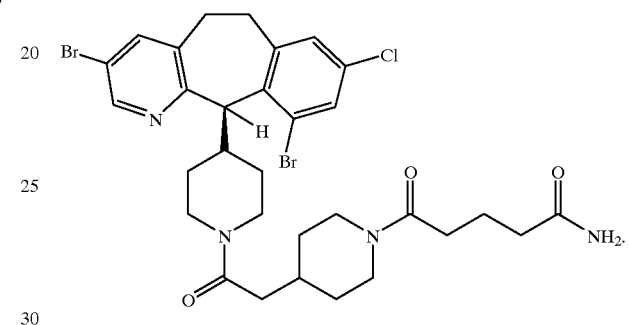
Compounds of this invention also include:
(16.0)
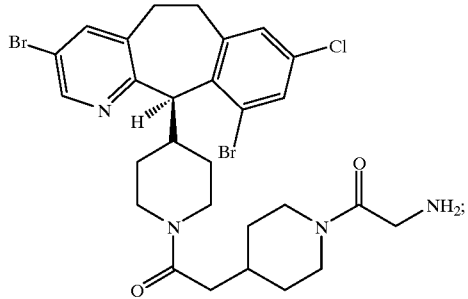
(17.0)
and -continued (18.0)

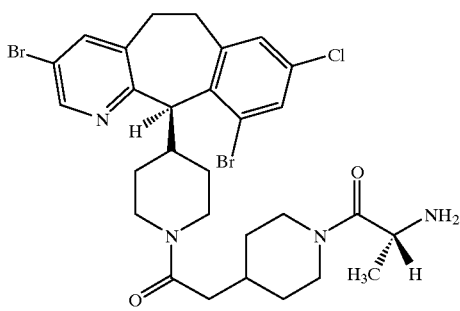

or pharmaceutically acceptable salts or solvates thereof.

The compounds of this invention also include the 1-N-oxides—i.e, for example, compounds of the the formula:

(1.6)

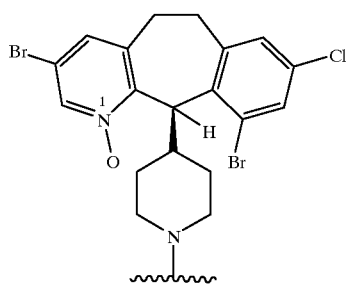

wherein ∿∿∿∿ represents the remainder of the compound, or pharmaceutically acceptable salts or solvates thereof.

Optical rotation of the compounds ((+)- or (−)-) are measured in methanol or ethanol at 25° C.

This invention includes the above compounds in the amorphous state or in the cyrstalline state.

Lines drawn into the ring systems indicate that the indicated bond may be attached to any of the substitutable ring carbon atoms.

Certain compounds of the present invention may exist in different isomeric forms (e.g., enantiomers or diastereoisomers) including atropisomers (i.e., compounds wherein the 7-membered ring is in a fixed conformation such that the 11-carbon atom is positioned above or below the plane of the fused benzene rings due to the presence of a 10-bromo substituent). The invention contemplates all such isomers both in pure form and in admixture, including racemic mixtures. Enol forms are also included.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold, silver and lithium salts. For example, compounds having the —OR$^{23}$ group wherein R$^{23}$ is H can form a sodium or lithium salt—i.e., a compound with a —ONa or —OLi group. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds of the invention may be prepared according to the procedures described in WO 95/10516 published Apr. 20, 1995, application Ser. No. 08/410,187 filed Mar. 24, 1995, application Ser. No. 08/577,951 filed Dec. 22, 1995 (now abandoned), application Ser. No. 08/615,760 filed Mar. 13, 1996 (now abandoned), WO 97/23478 published Jul. 3, 1997 which discloses the subject matter of Ser. No. 08/577,951 and 08/615,760, application Ser. No. 08/710,225 filed Sep. 13, 1996, and application Ser. No. 08/877,453 filed Jun. 17, 1997; the disclosures of each being incorporated herein by reference thereto; and according to the procedures described below.

Compounds of the invention can be prepared by reacting a compound of the formula:

(19.0)

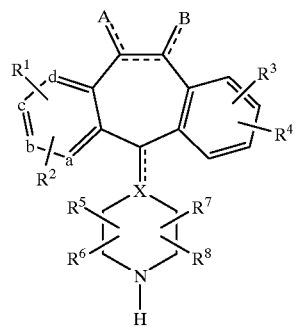

wherein all substituents are as defined for Formula 1.0, with the appropriate protected piperidinyl acetic acid (e.g., 1-N-t-butoxycarbonylpiperidinyl acetic acid together with DEC/HOBT/NMM in DMF at about 25° C. for about 18 hours to produce a compound of the formula:

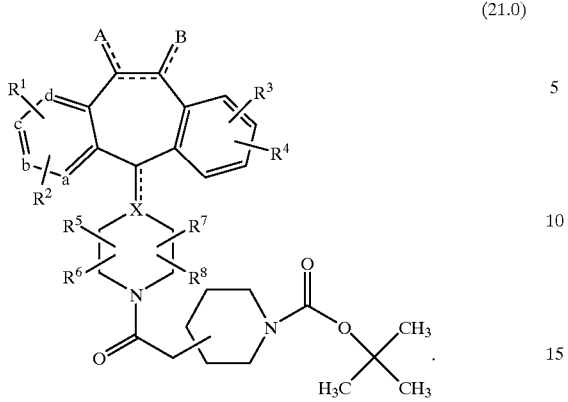

(21.0)

The compound of Formula 21.0 is then reacted either with TFA or 10% sulfuric acid in dioxane and methanol followed by NaOH to produce the compound of Formula 20.0

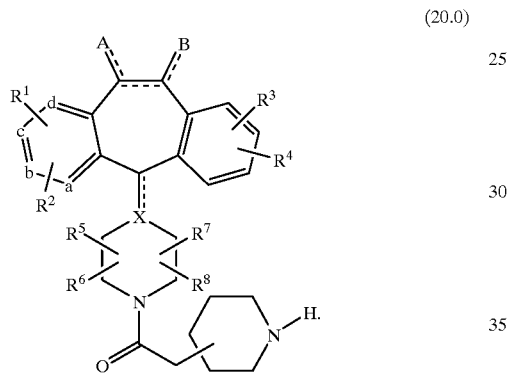

(20.0)

For example, the compound of formula

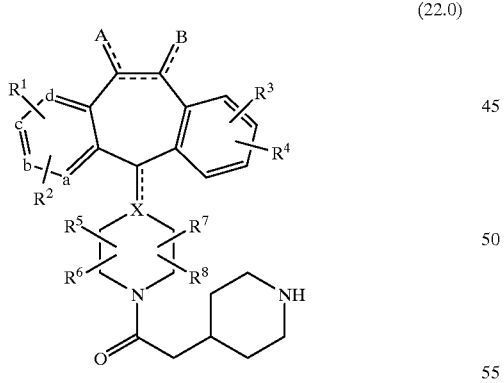

(22.0)

can be prepared by reaction of a compound of Formula 19.0 with 1-N-t-butoxy-carbonylpiperidinyl-4-acetic acid as described above.

For example, compounds of Formula 22.0 include the compounds:

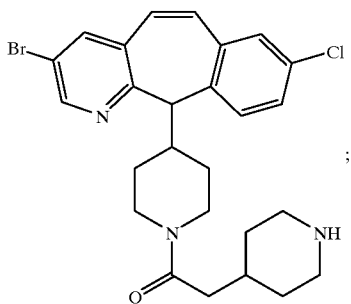

;

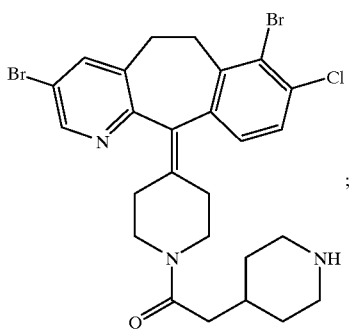

;

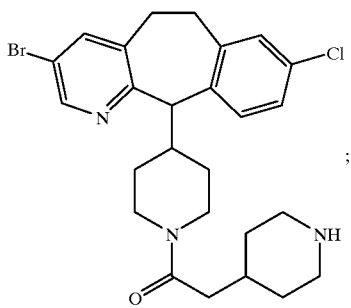

;

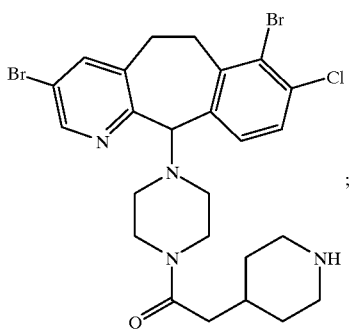

;

-continued

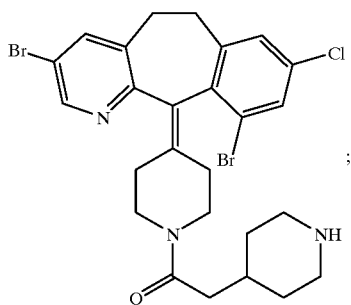

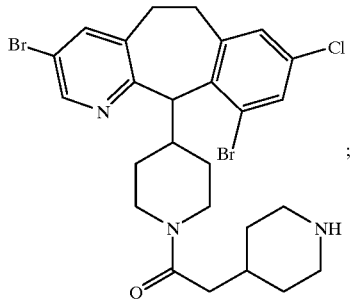

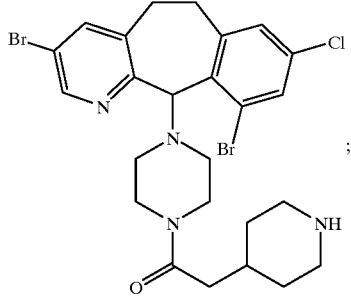

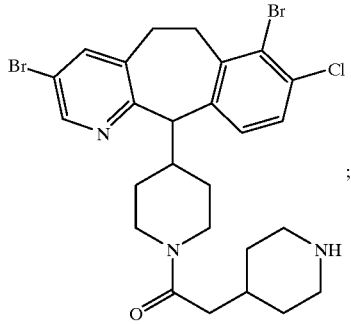

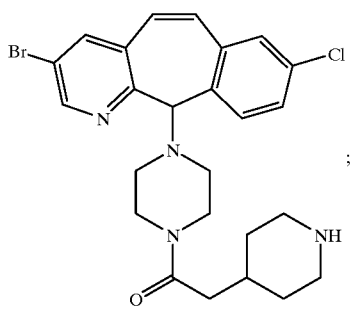

-continued

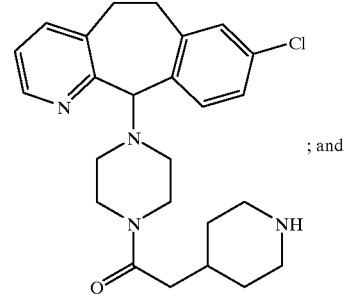

; and

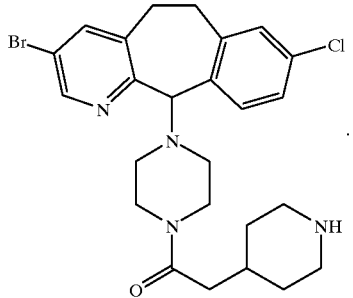

The preparation of these compounds are described in Preparative Examples 3, 4, 5, 6, 7, 8, 9, 10, 11, 12 and 13, respectively, below.

The compounds of the invention can be prepared by reacting a compound of the formula:

(19.1)

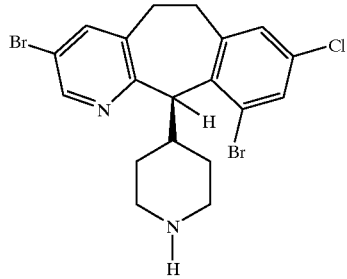

with the appropriate protected piperidinyl acetic acid (e.g., 1-N-t-butoxycarbonylpiperidinyl acetic acid together with DEC/HOBT/NMM in DMF at about 25° C. for about 18 hours to produce a compound of the formula:

(21.1)

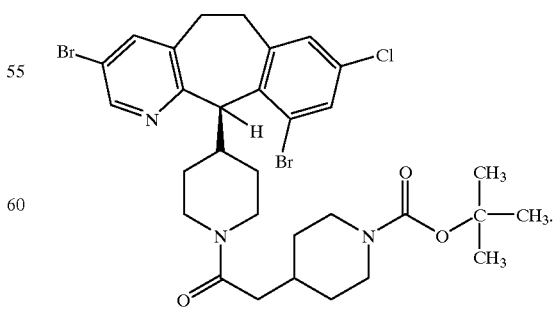

The compound of Formula 21.1 is then reacted either with TFA or 10% sulfuric acid in dioxane and methanol followed by NaOH to produce the compound of Formula 22.1

(22.1)

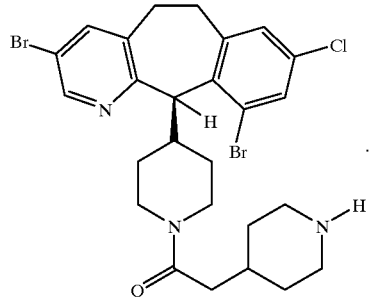

The amide compounds of this invention, represented by Formula b 1.7

(1.7)

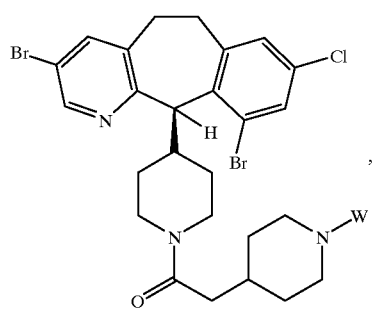

can be prepared by reacting the compound of Formula 22.1 with the appropriate carboxylic acid in the presence of a coupling agent such as DEC and HOBT in dimethylformamide. Alternatively, the compound of Formula 22.1 can be reacted with an acid chloride or anhydride in a solvent such as pyridine.

The W group on Formula 1.7 can contain functionality that can be converted to other functionality by methods, such as hydrolysis, that are well known in the art. For example, the compound of Formula 16.0-B, can be converted to the compound of Formula 74-B, and the compound of Formula 35.0-B to the compound of Formula 52.0-B by treatment with methanolic potassium hydroxide followed by acid. Also, compounds of Formulas 86.0-B and 89.0-B can be converted to compounds of Formulas 88.0-B and 90.0-B, respectively, by treatment with acids such as trifluoroacetic acid or dioxane saturated with HCl gas.

Compounds having an 1-N—O group:

(1.6)

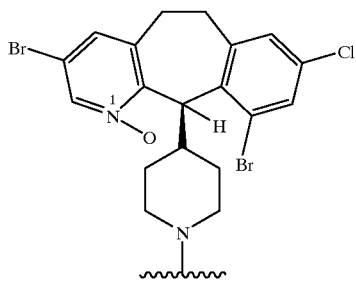

can be prepared from the corresponding pyridyl compounds:

(1.8)

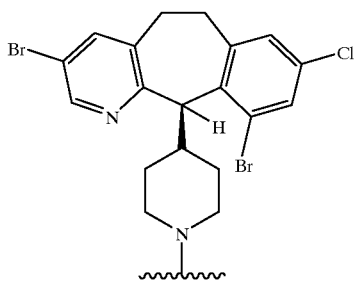

by oxidation with meta-chloroperoxybenzoic acid. This reaction is conducted in a suitable organic solvent, e.g., dichloromethane (usually anhydrous) or methylene chloride, at a suitable temperature, to produce the compounds of the invention having the N—O substituent at position 1 of Ring I of the tricyclic ring system.

Generally, the organic solvent solution of the starting tricyclic reactant is cooled to about 0° C. before the m-chloroperoxybenzoic acid is added. The reaction is then allowed to warm to room temperature during the reaction period. The desired product can be recovered by standard separation means. For example, the reaction mixture can be washed with an aqueous solution of a suitable base, e.g., saturated sodium bicarbonate or NaOH (e.g., 1N NaOH), and then dried over anhydrous magnesium sulfate. The solution containing the product can be concentrated in vacuo. The product can be purified by standard means, e.g., by chromatography using silica gel (e.g., flash column chromatography).

Alternatively, N—O compounds can be made from intermediate:

(19.1A)

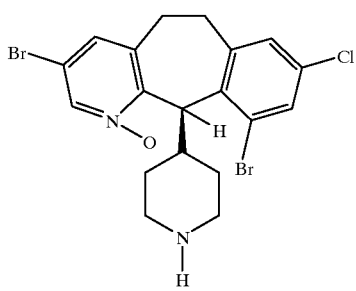

by the above oxidation procedure with m-chloroperoxybenzoic acid and

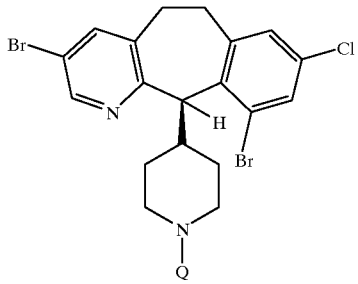
(19.1B)

wherein Q is a protecting group, e.g., BOC. After oxidation the protecting group is removed by techniques well known in the art. The N—O intermediate is then reacted further to produce the compounds of the invention.

Compounds of Formula 19.0 include the compound of Formula 19.1:

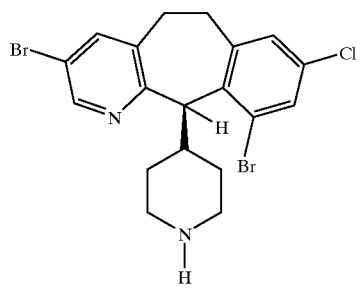
(19.1)

The compound of Formula 19.1 is prepared by methods known in the art, for example by methods disclosed in WO 95/10516, in U.S. Pat. No. 5,151,423 and those described below. The above intermediate compound can also be prepared by a procedure comprising the following steps:

(a) reacting an amide of the formula

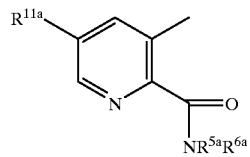

wherein $R^{11a}$ is Br, $R^{5a}$ is hydrogen and $R^{6a}$ is $C_1$–$C_6$ alkyl, aryl or heteroaryl; $R^{5a}$ is $C_1$–$C_6$ alkyl, aryl or heteroaryl and $R^{6a}$ is hydrogen; $R^{5a}$ and $R^{6a}$ are independently selected from the group consisting of $C_1$–$C_6$ alkyl and aryl; or $R^{5a}$ and $R^{6a}$, together with the nitrogen to which they are attached, form a ring comprising 4 to 6 carbon atoms or comprising 3 to 5 carbon atoms and one hetero moiety selected from the group consisting of —O— and —$NR^{9a}$—, wherein $R^{9a}$ is H, $C_1$–$C_6$ alkyl or phenyl;

with a compound of the formula

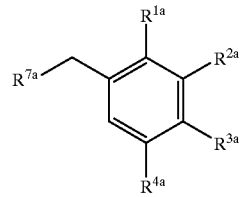

wherein $R^{1a}$, $R^{2a}$, $R^{3a}$ and $R^{4a}$ are independently selected from the group consisting of hydrogen and halo and $R^{7a}$ is Cl or Br, in the presence of a strong base to obtain a compound of the formula

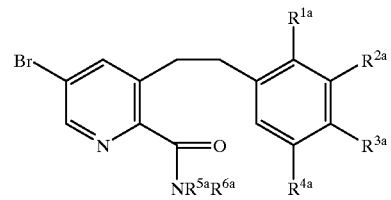

(b) reacting a compound of step (a) with
 (i) $POCl_3$ to obtain a cyano compound of the formula

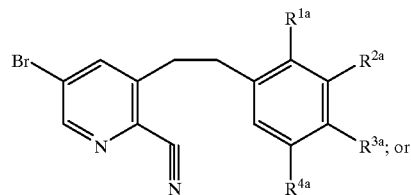

(ii) DIBALH to obtain an aldehyde of the formula

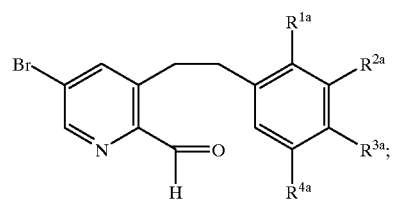

(c) reacting the cyano compound or the aldehyde with a piperidine derivative of the formula

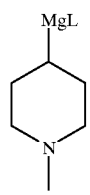

wherein L is a leaving group selected from the group consisting of Cl and Br, to obtain a ketone or an alcohol of the formula below, respectively:

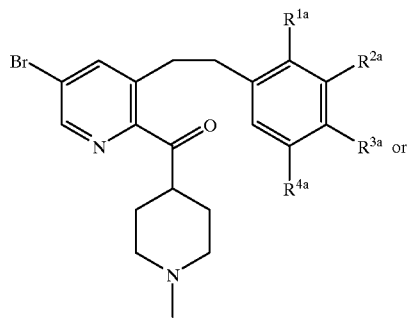

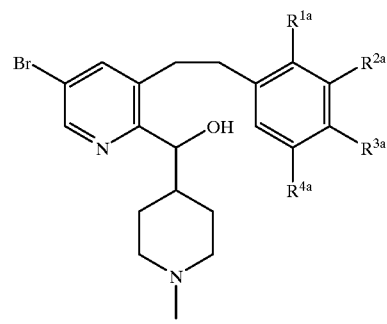

(d)(i) cyclizing the ketone with $CF_3SO_3H$ to obtain a compound of Formula 13.0a wherein the dotted line represents a double bond; or (d)(ii) cyclizing the alcohol with polyphosphoric acid to obtain an Intermediate compound wherein the dotted line represents a single bond.

Methods for preparing the Intermediate compounds disclosed in WO 95/10516, U.S. Pat. No. 5,151,423 and described below employ a tricyclic ketone intermediate. Such intermediates of the formula

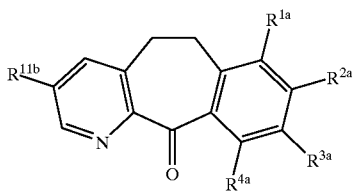

wherein $R^{11b}$, $R^{1a}$, $R^{2a}$, $R^{3a}$ and $R^{4a}$ are independently selected from the group consisting of hydrogen and halo, can be prepared by the following process comprising:

(a) reacting a compound of the formula

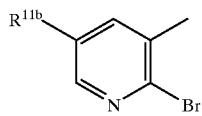

(i) with an amine of the formula $NHR^{5a}R^{6a}$, wherein $R^{5a}$ and $R^{6a}$ are as defined in the process above; in the presence of a palladium catalyst and carbon monoxide to obtain an amide of the formula:

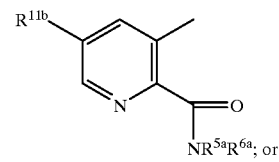

(ii) with an alcohol of the formula $R^{10a}OH$, wherein $R^{10a}$ is $C_1$–$C_6$ lower alkyl or $C_3$–$C_6$ cycloalkyl, in the presence of a palladium catalyst and carbon monoxide to obtain the ester of the formula

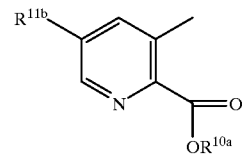

followed by reacting the ester with an amine of formula $NHR^{5a}R^{6a}$ to obtain the amide;

(b) reacting the amide with an iodo-substituted benzyl compound of the formula

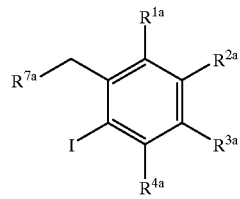

wherein $R^{1a}$, $R^{2a}$, $R^{3a}$, $R^{4a}$ and $R^{7a}$ are as defined above, in the presence of a strong base to obtain a compound of the formula

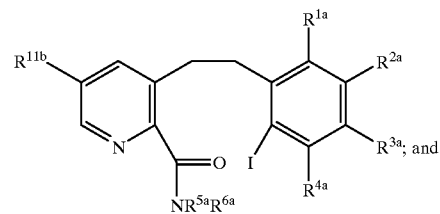

(c) cyclizing a compound of step (b) with a reagent of the formula $R^{8a}MgL$, wherein $R^{8a}$ is $C_1$–$C_8$ alkyl, aryl or heteroaryl and L is Br or Cl, provided that prior to cyclization, compounds wherein $R^{5a}$ or $R^{6a}$ is hydrogen are reacted with a suitable N-protecting group.

(+)-Isomers of compounds of Formula 19.2

(19.2)

can be prepared with high enantioselectivity by using a process comprising enzyme catalyzed transesterification. Preferably, a racemic compound of Formula 19.3

(19.3)

is reacted with an enzyme such as Toyobo LIP-300 and an acylating agent such as trifluoroethly isobutyrate; the resultant (+)-amide is then isolated from the (−)-enantiomeric amine by techniques well known in the art, and then the (+)-amide is hydrolyzed, for example by refluxing with an acid such as $H_2SO_4$, and the resulting compound is then reduced with DIBAL by techniques well known in the art to obtain the corresponding optically enriched (+)-isomer of Formula 19.2. Alternatively, a racemic compound of Formula 19.3, is first reduced to the corresponding racemic compound of Formula 19.2 and then treated with the enzyme (Toyobo LIP-300) and acylating agent as described above to obtain the (+)-amide, which is hydrolyzed to obtain the optically enriched (+)-isomer.

Those skilled in the art will appreciate that compounds of Formula 1.0 having other $R^1$, $R^2$, $R^3$ and $R^4$ substituents may be made by the above enzyme process.

To produce the compounds of Formula 1.0, wherein W is r is 0, and $R^{13}$ and $R^{14}$ are selected from H or —C(O)$OR^{16}$, the compounds of Formulas 20.0 or 22.0 are reacted with the appropriate protected amino acid:

in the presence of DEC and HOBt in dimethylformamide to produce a compound of the formula:

(23.0)

(24.0)

respectively.

Reaction of compounds of Formulas 23.0 or 24.0 with TFA in methylene chloride results in the deprotected compounds:

(25.0)

(26.0)

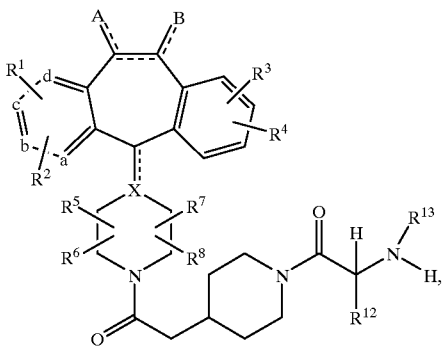

respectively.

Compounds of Formula 1.0 wherein W is

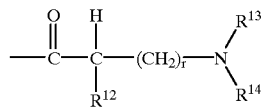

r is 0, $R^{12}$ is H, $R^{13}$ or $R^{14}$ is H, and the remaining $R^{13}$ or $R^{14}$ is —C(O)O$R^{16}$ can be prepared by reacting a compound of Formula 1.0 wherein W is

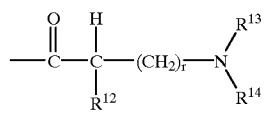

r is 0, $R^{12}$ is H, and $R^{13}$ and $R^{14}$ are both H, with the appropriate chloroformate

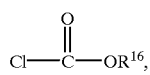

TEA and CH$_2$Cl$_2$.

Compounds of Formulas 25.0 or 26.0 wherein $R^{13}$ is selected from —SO$_2$R$^{17}$ or —C(O)R$^{18}$ can be prepared by reacting a compound of Formula 25.0 or 26.0 with a suitable sulfonyl chloride (R$^{17}$SO$_2$Cl) or a suitable acyl chloride (R$^{18}$C(O)Cl) with TEA in a suitable organic solvent (e.g., CH$_2$Cl$_2$).

Compounds of Formula 1.0 wherein W is

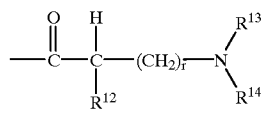

r is 1 or 2 and $R^{12}$ is H can be prepared by reacting a compound of Formula 20.0 or 22.0 with the appropriately substitued 5 carboxylic acid and, for example DEC, HOBT and N-methylmorpholine, or by reacting a compound of Formula 20.0 or 22.0 with the appropriately substituted acid chloride.

For example, a compound of Formula 20.0 or 22.0 can be reacted with

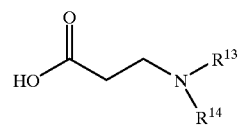

from propionic acid, wherein $R^{13}$ and $R^{14}$ are, for example, alkyl (e.g., methyl). Where the amino carboxylic acid is not commercially available, it can be prepared by reaction of ethyl acrylate with the appropriate amino compound (as described by Ahn, K. H. et al., Tetrahedron Letters, 35, 1875–1878 (1994)) with subsequent hydrolysis of the ester to the desired aminocarboxylic acid.

Also, for example, a compound of Formula 20.0 or 22.0 can be reacted with

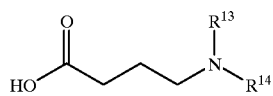

from butyric acid, wherein $R^{13}$ and $R^{14}$ are, for example, alkyl (e.g., methyl). Where the amino carboxylic acid is not commercially available, the appropriate acid chloride can be prepared in a manner similar to that described by Goel, O. P. et al., Synthesis, p. 538 (1973). The acid chloride is then reacted with a compound of Formula 20.0 or 22.0 to give the compound (20.0A)

![Formula 20.0A structure]

(22.0A)

![Formula 22.0A structure]

respectively. The chloro atom can then be displaced with the appropriate amine to give the desired compound.

Where either $R^{13}$ or $R^{14}$ is H, then the starting material would be a protected amino carboxylic acid

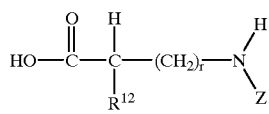

wherein Z is an appropriater protecting group (e.g., BOC, CBZ (carbonylbenzyloxy) or TFA). Coupling this protected amino carboxylic acid with a compound of Formula 20.0 or 22.0 would then give the amino protected intermediate (20.0B)

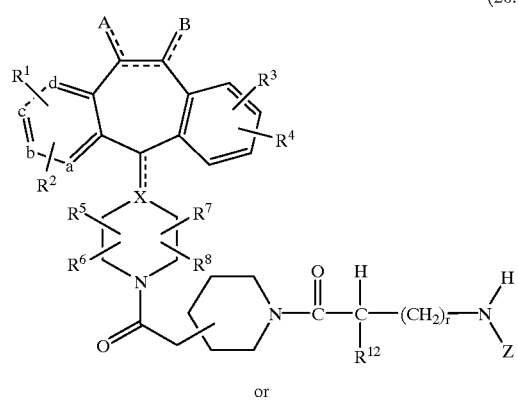

or (22.0B)

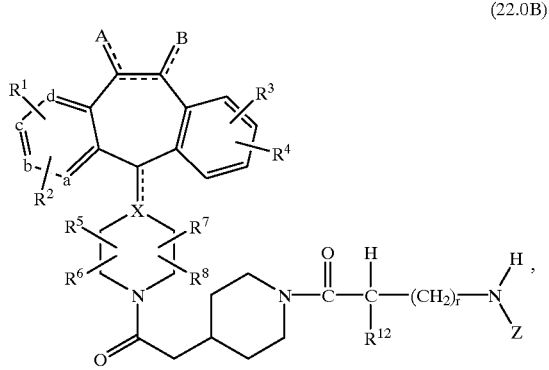

respectively. The amino protected intermediate (20.0B or 22.0B) would then be alkylated, and then the protecting group removed, using standard procedures known in the art.

Compounds of Formula 1.0 wherein W is

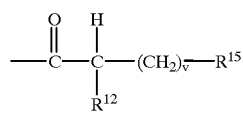

v is 0, and $R^{12}$ is H can be prepared by reacting a compound of Formula 20.0 or 22.0 with chloroacetylchloride, TEA and $CH_2Cl_2$ to produce a compound of the formula:

(26.0)

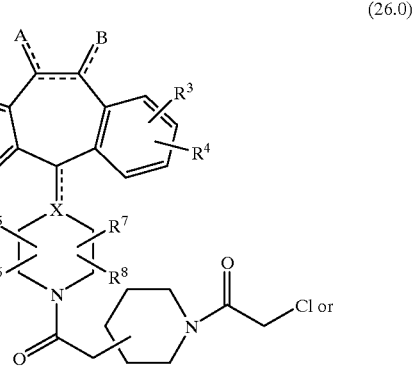

(27.0)

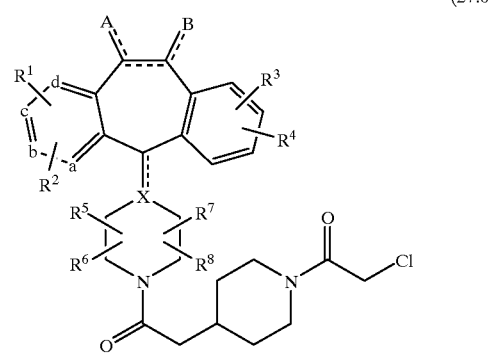

The chloro atom in the —C(O)CH$_2$Cl group in the compound of Formula 26.0 or 27.0 is then displaced with an appropriate nucleophile, $R^{15}$, using a suitable base, e.g., sodium carbonate, and optionally, a suitable suitable solvent (e.g., DMF).

Compounds of Formula 1.0 wherein W is

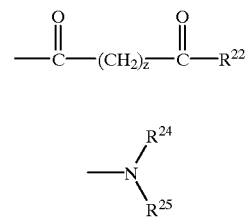

z is 0, and $R^{22}$ is can be prepared from compounds of Formula 20.0 or 22.0 by reaction with oxallyl chloride and an excess of the amine

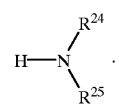

Compounds of Formula 1.0 wherein W is

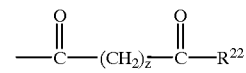

z is 1, 2, 3, 4 or 5 and $R^{22}$ is —OR$^{23}$, and $R^{23}$ is, for example, alkyl, can be prepared by reaction of a compound of- Formula 20.0 or 22.0 with the appropriate substituted dicarboxylic acid which is protected as a mono ester with an appropriate alkyl or aryl group. The corresponding acids (i.e., $R^{23}$ is H) can be obtained by base hydrolysis (e.g., NaOH) of the ester. The compounds, wherein $R^{22}$ is —$NR^{24}R^{25}$, can be prepared by reacting the appropriately substituted amine with the carboxylic acid generated above using DEC, HOBT and NMM. For example, for compounds wherein z is 3 a glutarate

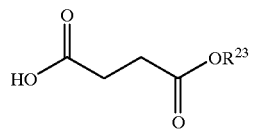

(wherein $R^{23}$ is alkyl, e.g., methyl) can be used, and for compounds wherein z is 1 a malonate

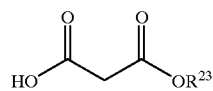

wherein $R^{23}$ is alky, e.g., ethyl) can be used.

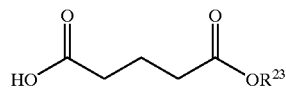

(wherein $R^{23}$ is alky, e.g., methyl) can be used, and for compounds wherein z is 2 a succinate Reaction Scheme 1 illustrates the preparation of compounds of this invention.

SCHEME 1

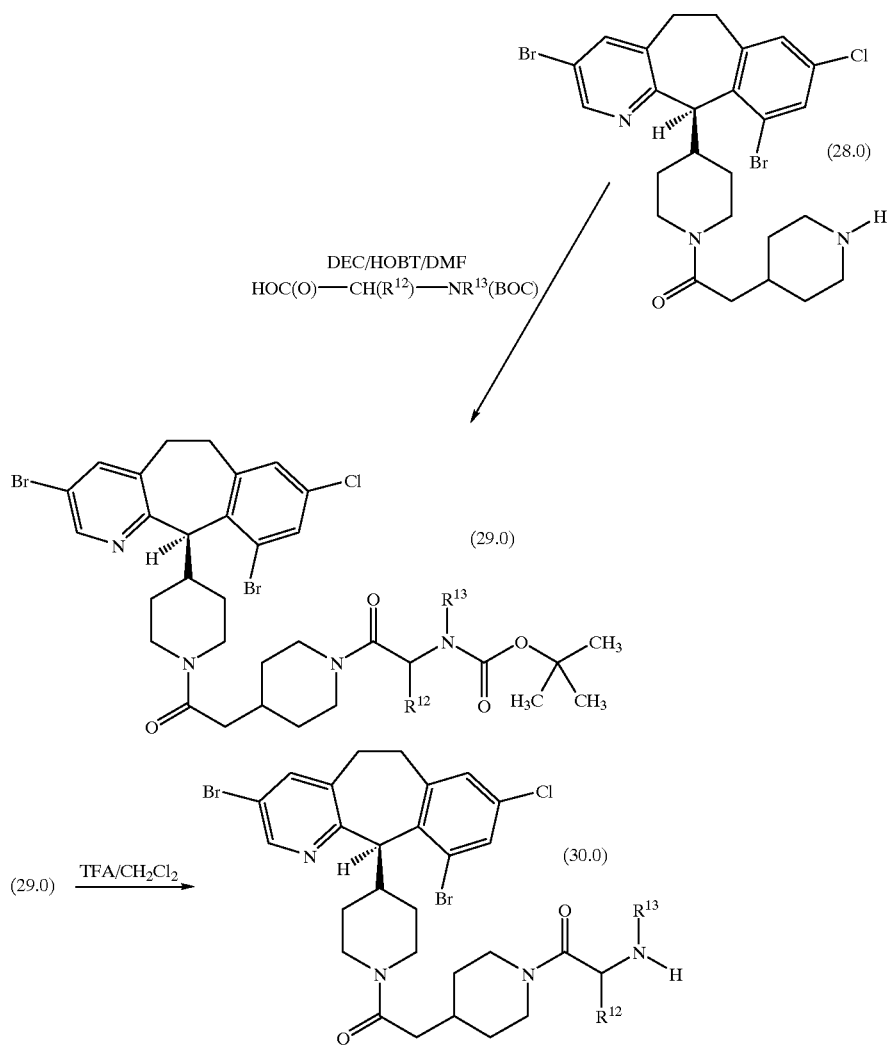

Compounds useful in this invention are exemplified by the following examples, which should not be construed to limit the scope of the disclosure.

PREPARATIVE EXAMPLE 1

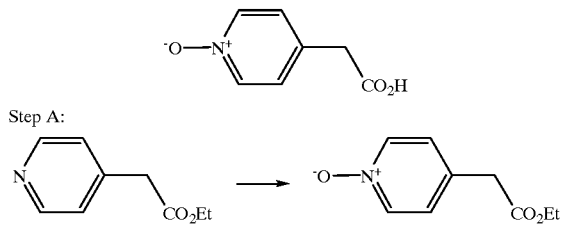

Step A:

Combine 10 g (60.5 mmol) of ethyl 4-pyridylacetate and 120 mL of dry CH$_2$Cl$_2$ at −20° C., add 10.45 g (60.5 mmol) of MCPBA and stir at −20° C. for 1 hour and then at 25° C. for 67 hours. Add an additional 3.48 g (20.2 mmoles) of MCPBA and stir at 25° C. for 24 hours. Dilute with CH$_2$Cl$_2$ and wash with saturated NaHCO$_3$ (aqueous) and then water. Dry over MgSO$_4$, concentrate in vacuo to a residue, and chromatograph (silica gel, 2%–5.5% (10% NH$_4$OH in MeOH)/CH$_2$Cl$_2$) to give 8.12 g of the product compound. Mass Spec.: MH$^+$=182.15

Step B:

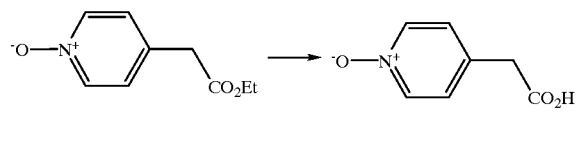

Combine 3.5 g (19.3 mmol) of the product of Step A, 17.5 mL of EtOH and 96.6 mL of 10% NaOH (aqueous) and heat the mixture at 67° C. for 2 hours. Add 2 N HCl (aqueous) to adjust to pH=2.37 and concentrate in vacuo to a residue. Add 200 mL of dry EtOH, filter through celite® and wash the filter cake with dry EtOH (2×50 ml). Concentrate the combined filtrates in vacuo to give 2.43 g of the title compound.

PREPARATIVE EXAMPLE 2

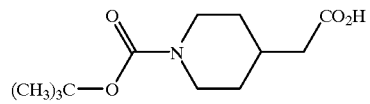

The title compound is prepared via the process disclosed in PCT International Publication No. WO95/10516.

PREPARATIVE EXAMPLE 3

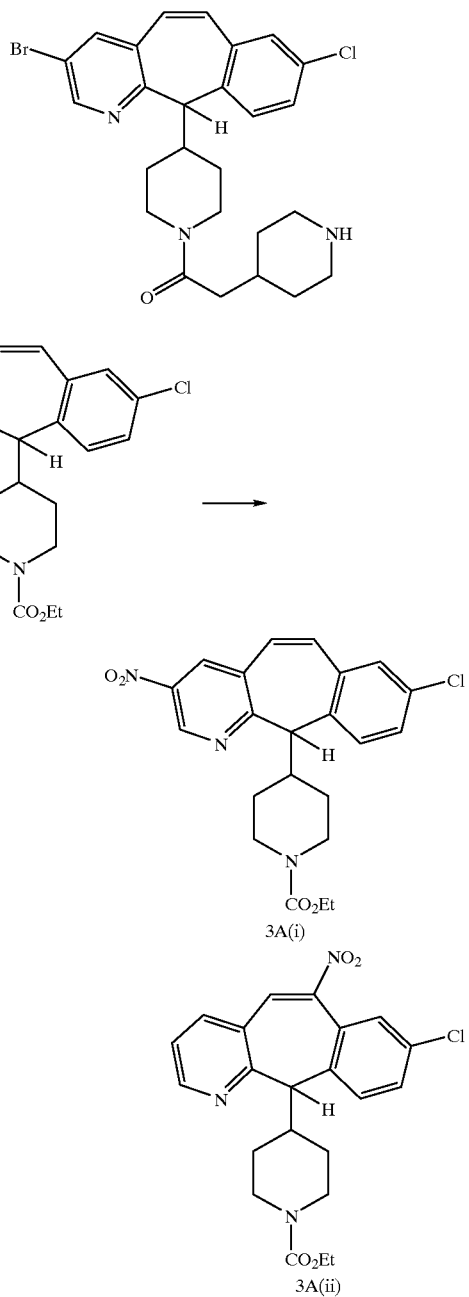

Step A:

Combine 14.95 g (39 mmol) of 8-chloro-11-(1-ethoxycarbonyl-4-piperidinyl)-11H-benzo[5,6]cyclohepta[1,2-b]pyridine and 150 mL of CH$_2$Cl$_2$, then add 13.07 g (42.9 mmol) of (nBu)$_4$NNO$_3$ and cool the mixture to 0° C. Slowly add (dropwise) a solution of 6.09 mL (42.9 mmol) of TFAA in 20 mL of CH$_2$Cl$_2$ over 1.5 hours. Keep the mixture at 0° C. overnight, then wash successively with saturated NaHCO$_3$ (aqueous), water and brine. Dry the organic solution over Na$_2$SO$_4$, concentrate in vacuo to a residue and chromatograph the residue (silica gel, EtOAc/hexane gradient) to give 4.32 g and 1.90 g of the two product compounds 3A(i) and 3A(ii), respectively.

Mass Spec. for compound 3A(i): MH+=428.2;

Mass Spec. for compound 3A(ii): MH+=428.3.

Step B:

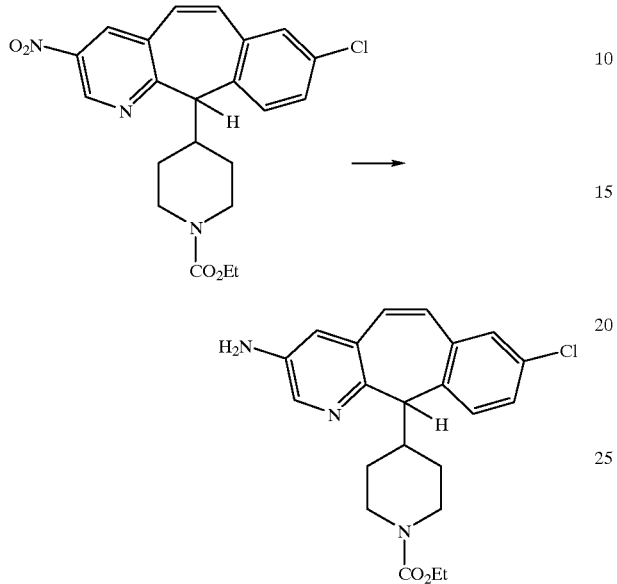

Combine 22.0 g (51.4 mmol) of the product 3A(i) from Step A, 150 mL of 85% EtOH (aqueous), 25.85 g (0.463 mole) of Fe powder and 2.42 g (21.8 mmol) of CaCl$_2$, and heat at reflux overnight. Add 12.4 g (0.222 mole) of Fe powder and 1.2 g (10.8 mmol) of CaCl$_2$ and heat at reflux for 2 hours. Add another 12.4 g (0.222 mole) of Fe powder and 1.2 g (10.8 mmol) of CaCl$_2$ and heat at reflux for 2 hours more. Filter the hot mixture through celite®, wash the celite® with 50 mL of hot EtOH and concentrate the filtrate in vacuo to a residue. Add 100 mnL of anhydrous EtOH, concentrate to a residue and chromatograph the residue (silica gel, MeOH/CH$_2$Cl$_2$ gradient) to give 16.47 g of the product compound.

Step C:

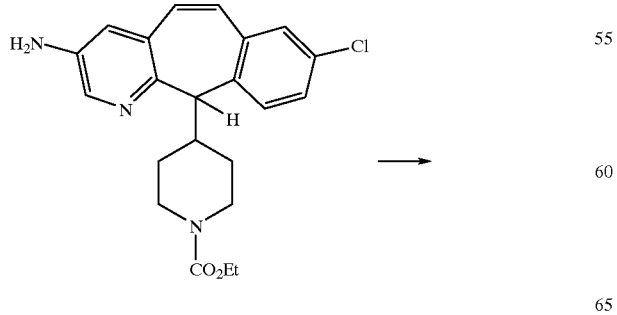

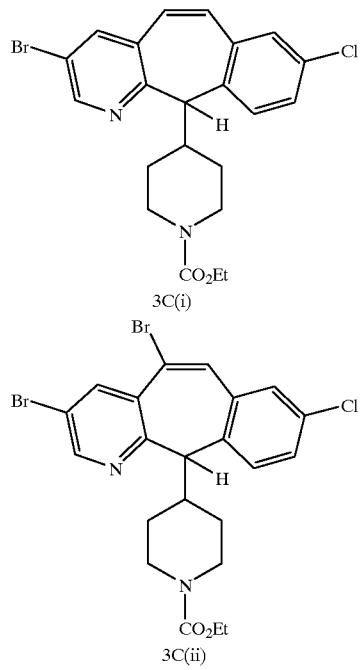

Combine 16.47 g (41.4 mmol) of the product from Step B, and 150 mL of 48% HBr (aqueous) and cool to −3° C. Slowly add (dropwise) 18 mL of bromine, then slowly add (dropwise) a solution of 8.55 g (0.124 mole) of NaNO$_2$ in 85 mL of water. Stir for 45 minutes at −3° to 0° C., then adjust to pH=10 by adding 50% NaOH (aqueous). Extract with EtOAc, wash the extracts with brine and dry the extracts over Na$_2$SO$_4$. Concentrate to a residue and chromatograph (silica gel, EtOAc/hexane gradient) to give 10.6 g and 3.28 g of the two product compounds 3C(i) and 3C(ii), respectively.

Mass Spec. for compound 3C(i): MH+=461.2;
Mass Spec. for compound 3C(ii): MH+=539.

Step D:

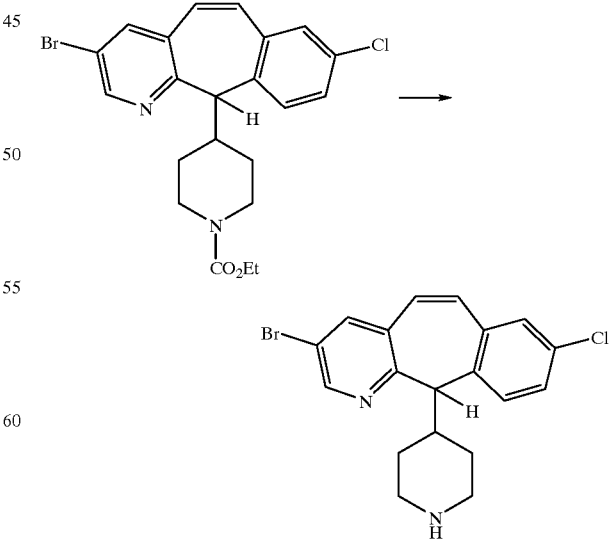

Hydrolyze the product 3C(i) of Step C by dissolving in concentrated HCl and heating to about 100° C. for @ 16 hours. Cool the mixture, the neutralize with 1 M NaOH (aqueous). Extract with CH₂Cl₂, dry the extracts over MgSO₄, filter and concentrate in vacuo to the title compound.

Mass Spec.: MH⁺=466.9.

Step E:

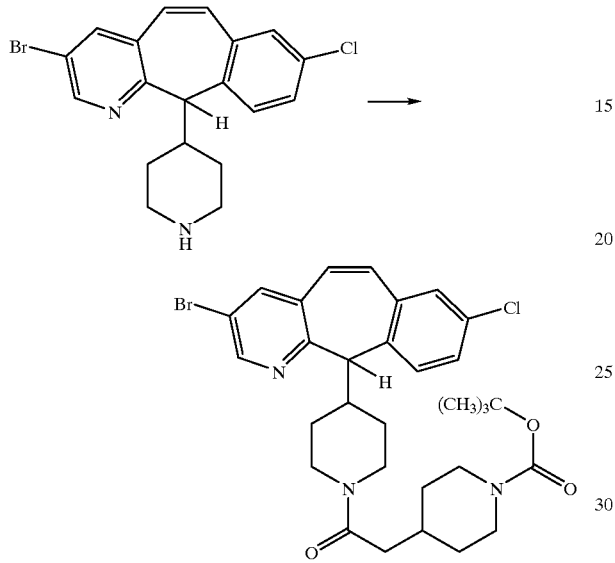

Dissolve 1.160 g (2.98 mmol) of the title compound from Step D in 20 mL of DMF, stir at room temperature, and add 0.3914 g (3.87 mmol) of 4-methyl-morpholine, 0.7418 g (3.87 mmol) of DEC, 0.5229 g (3.87 mmol) of HOBT, and 0.8795 g (3.87 mmol) of 1-N-t-butoxycarbonyl-piperidinyl-4-acetic acid. Stir the mixture at room temperature for 2 days, then concentrate in vacuo to s residue and partition the residue between CH₂Cl₂ and water. Wash the organic phase successively with saturated NaHCO₃ (aqueous), 10% NaH₂PO₄ (aqueous) and brine. Dry the organic phase over MgSO₄, filter and concentrate in vacuo to a residue. Chromatograph the residue (silica gel, 2% MeOH/CH₂Cl₂+NH₃) to give 1.72 g of the product. m.p.=94.0–94.5° C., Mass Spec.: MH⁺=616.3, Elemental analysis: calculated—C, 60.54; H, 6.06; N, 6.83; found—C, 59.93; H, 6.62; N, 7.45.

Step F:

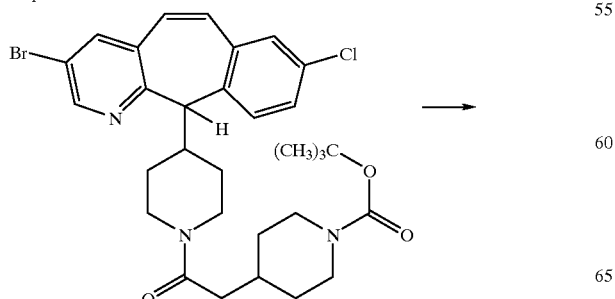

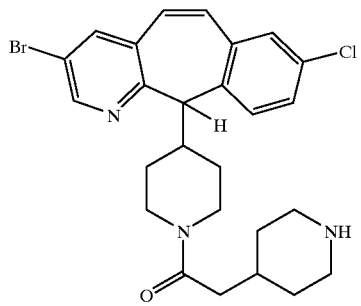

Combine 1.67 g (2.7 mmol) of the product of Step E and 20 mL of CH₂Cl₂ and stir at 0° C. Add 20 mL of TFA, stir the mixture for 2 hours, then basify the mixture with 1 N NaOH (aqueous). Extract with CH₂Cl₂, dry the organic phase over MgSO₄, filter and concentrate in vacuo to give 1.16 g of the product. m.p.=140.2–140.8° C., Mass Spec.: MH⁺=516.2.

PREPARATIVE EXAMPLE 4

Step A:

Combine 25.86 g (55.9 mmol) of 4-(8-chloro-3-bromo-5,6-dihydro-11H-benzo[5,6]cyclohepta[1,2-b]pyridin-11-ylidene)-1-piperidine- 1-carboxylic acid ethyl ester and 250 mL of concentrated H₂SO₄ at −5° C., then add 4.8 g (56.4 mmol) of NaNO₃ and stir for 2 hours. Pour the mixture into 600 g of ice and basify with concentrated NH₄OH (aqueous). Filter the mixture, wash with 300 mL of water, then extract with 500 mL of CH₂Cl₂. Wash the extract with 200 mL of water, dry over MgSO₄, then filter and concentrate in vacuo to a residue. Chromatograph the residue (silica gel, 10% EtOAc/CH₂Cl₂) to give 24.4 g (86% yield) of the product. m.p.=165–167° C., Mass Spec.: MH⁺=506 (CI), Elemental analysis: calculated—C, 52.13; H, 4.17; N, 8.29; found—C, 52.18; H, 4.51; N, 8.16.

Step B:

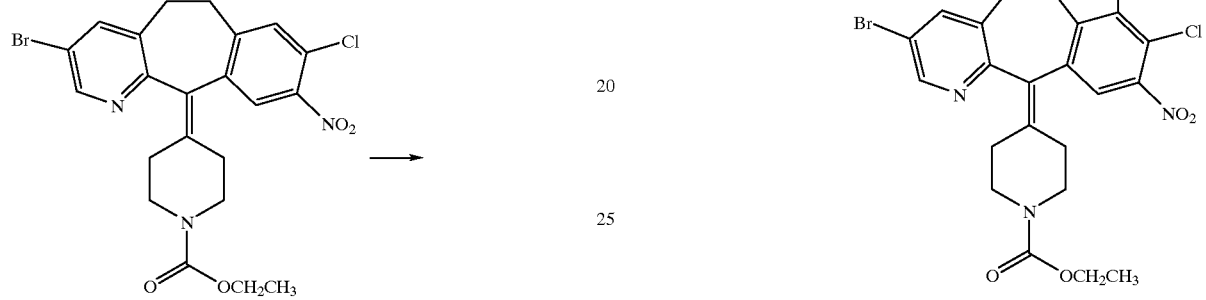

Combine 20 g (40.5 mmol) of the product of Step A and 200 mL of concentrated H₂SO₄ at 20° C., then cool the mixture to 0° C. Add 7.12 g (24.89 mmol) of 1,3-dibromo-5,5-dimethylhydantoin to the mixture and stir for 3 hours at 20° C. Cool to 0° C., add an additional 1.0 g (3.5 mmol) of the dibromohydantoin and stir at 20° C. for 2 hours. Pour the mixture into 400 g of ice, basify with concentrated NH₄OH (aqueous) at 0° C., and collect the resulting solid by filtration. Wash the solid with 300 mL of water, slurry in 200 mL of acetone and filter to provide 19.79 g (85.6% yield) of the product. m.p.=236–237° C., Mass Spec.: MH⁺=584 (CI), Elemental analysis: calculated—C, 45.11; H, 3.44; N, 7.17; found—C, 44.95; H, 3.57; N, 7.16.

Step C:

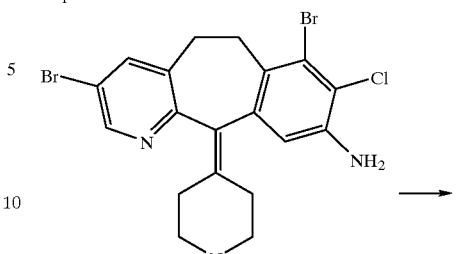

Combine 25 g (447 mmol) of Fe filings, 10 g (90 mmol) of CaCl₂ and a suspension of 20 g (34.19 mmol) of the product of Step B in 700 mL of 90:10 EtOH/water at 50° C. Heat the mixture at reflux overnight, filter through Celite® and wash the filter cake with 2×200 mL of hot EtOH. Combine the filtrate and washes, and concentrate in vacuo to a residue. Extract the residue with 600 mL of CH₂Cl₂, wash with 300 mL of water and dry over MgSO₄. Filter and concentrate in vacuo to a residue, then chromatograph (silica gel, 30% EtOAc/CH₂Cl₂) to give 11.4 g (60% yield) of the product. m.p.=211–212° C., Mass Spec.: MH⁺=554 (CI), Elemental analysis: calculated—C, 47.55; H, 3.99; N, 7.56; found—C, 47.45; H, 4.31; N, 7.49.

Step D:

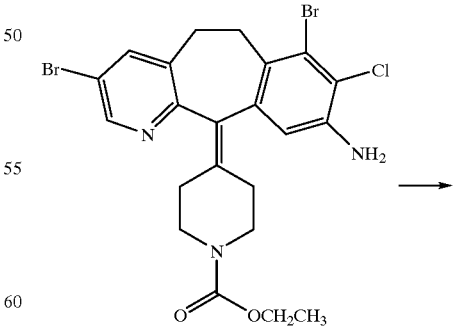

-continued

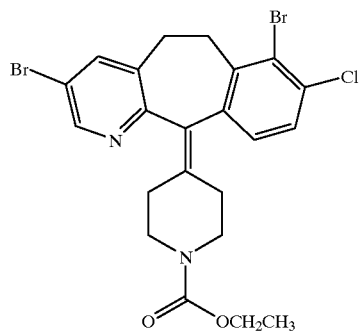

Slowly add (in portions) 20 g (35.9 mmol) of the product of Step C to a solution of 8 g (116 mmol) of NaNO₂ in 120 mL of concentrated HCl (aqueous) at −10° C. Stir the resulting mixture at 0° C. for 2 hours, then slowly add (dropwise) 150 mL (1.44 mole) of 50% H₃PO₂ at 0° C. over a 1 hour period. Stir at 0° C. for 3 hours, then pour into 600 g of ice and basify with concentrated NH₄OH (aqueous). Extract with 2×300 mL of CH₂Cl₂, dry the extracts over MgSO₄, then filter and concentrate in vacuo to a residue. Chromatograph the residue (silica gel, 25% EtOAc/hexanes) to give 13.67 g (70% yield) of the product. m.p.=163–165° C., Mass Spec.: MH⁺=539 (CI), Elemental analysis: calculated—C, 48.97; H, 4.05; N, 5.22; found—C, 48.86; H, 3.91; N, 5.18.

Step E:

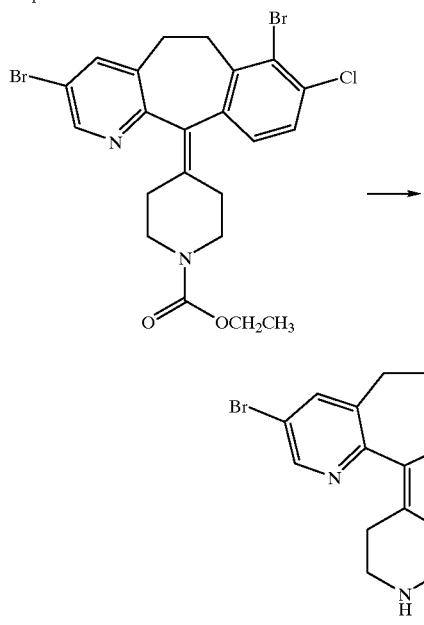

Combine 6.8 g (12.59 mmol) of the product of Step D and 100 mL of concentrated HCl (aqueous) and stir at 85° C. overnight. Cool the mixture, pour it into 300 g of ice and basify with concentrated NH₄OH (aqueous). Extract with 2×300 mL of CH₂Cl₂, then dry the extracts over MgSO₄. Filter, concentrate in vacuo to a residue, then chromatograph (silica gel, 10% MeOH/EtOAc +2% NH₄OH (aqueous)) to give 5.4 g (92% yield) of the title compound. m.p.= 172–174° C., Mass Spec.: MH⁺=467 (FAB), Elemental analysis: calculated—C, 48.69; H, 3.65; N, 5.97; found—C, 48.83; H, 3.80; N, 5.97.

Step F:

Following essentially the same procedure as Step C of Preparative Example 5 below, the title compound from Step E above is reacted with 1-N-t-butoxycarbonylpiperidinyl-4-acetic acid to produce the compound

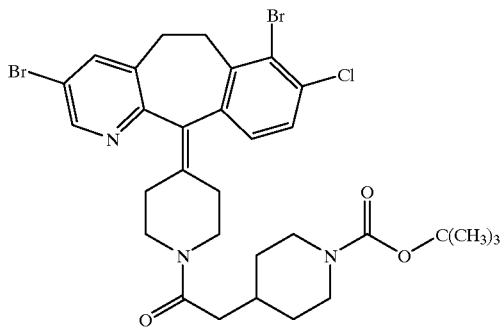

Step G:

Following essentially the same procedure as Step D of Preparative Example 5 below, the title compound from Step F above is deprotected to yield the title compound of Preparative Example 4.

PREPARATIVE EXAMPLE 5

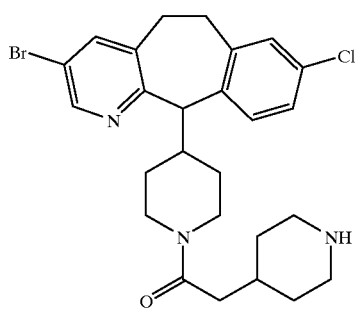

Step A:

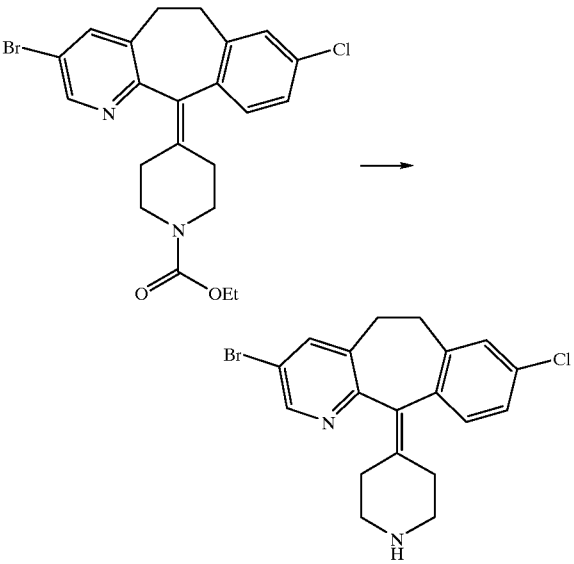

Hydrolyze 2.42 g of 4-(8-chloro-3-bromo-5,6-dihydro-1H-benzo[5,6]cyclohepta[1,2-b]pyridin-11-ylidene)-1-piperidine-1-carboxylic acid ethyl ester via substantially the same procedure as described in Preparative Example 3, Step D, to give 1.39 g (69% yield) of the product.

Step B:

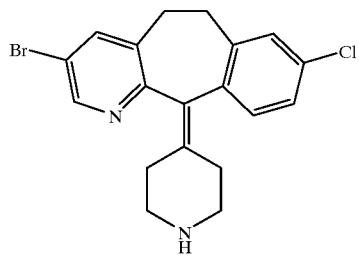
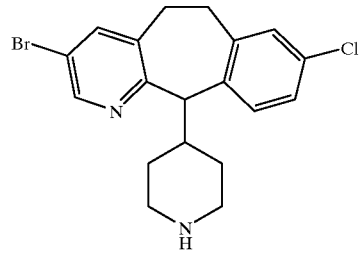

Combine 1 g (2.48 mmol) of the product of Step A and 25 mL of dry toluene, add 2.5 mL of 1 M DIBAL in toluene and heat the mixture at reflux. After 0.5 hours, add another 2.5 mL of 1 M DIBAL in toluene and heat at reflux for 1 hour. (The reaction is monitored by TLC using 50% MeOH/ CH$_2$Cl$_2$+NH$_4$OH (aqueous).) Cool the mixture to room temperature, add 50 mL of 1 N HCl (aqueous) and stir for 5 min. Add 100 mL of 1 N NaOH (aqueous), then extract with EtOAc (3×150 mL). Dry the extracts over MgSO$_4$, filter and concentrate in vacuo to give 1.1 g of the title compound.

Step C:

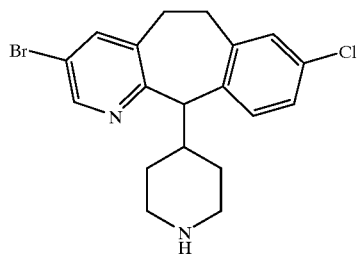
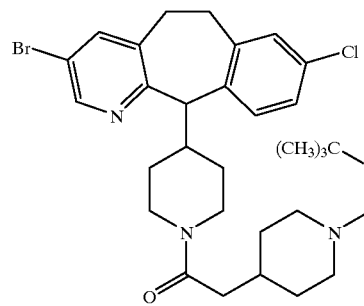

Combine 0.501 g (1.28 mmol) of the title compound of Step B and 20 mL of dry DMF, then add 0.405 g (1.664 mmol) of 1-N-t-butoxycarbonylpiperidinyl-4-acetic acid, 0.319 g (1.664 mmol) of DEC, 0.225 g (1.664 mmol) of HOBT, and 0.168 g (1.664 mmol) of 4-methylmorpholine and stir the mixture at room temperature overnight. Concentrate the mixture in vacuo to a residue, then partition the residue between 150 mL of CH$_2$Cl$_2$ and 150 mL of saturated NaHCO$_3$ (aqueous). Extract the aqueous phase with another 150 mL of CH$_2$Cl$_2$. Dry the organic phase over MgSO$_4$, and concentrate in vacuo to a residue. Chromatograph the residue (silica gel, 500 mL hexane, 1 L of 1% MeOH/CH$_2$Cl$_2$+ 0.1% NH$_4$OH (aqueous), then 1 L of 2% MeOH/CH$_2$Cl$_2$+ 0.1% NH$_4$OH (aqueous)) to give 0.575 g of the product. m.p.=115°–125° C.; Mass Spec.: MH$^+$=616.

Step D:

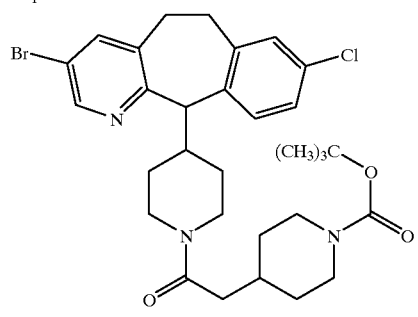

Combine 0.555 g (0.9 mmol) of the product of Step C and 15 mL of CH$_2$Cl$_2$ and cool the mixture to 0° C. Add 15 mL of TFA and stir at 0° C. for 2 hours. Concentrate in vacuo at 40–45° C. to a residue, then partition the residue between 150 mL of CH$_2$Cl$_2$ and 100 mL of saturated NaHCO$_3$ (aqueous). Extract the aqueous layer with 100 mL of CH$_2$Cl$_2$, combine the extracts and dry over MgSO$_4$. Concentrate in vacuo to give 0.47 g of the product. m.p.= 140°–150° C.; Mass Spec.: MH$^+$=516.

PREPARATIVE EXAMPLE 6

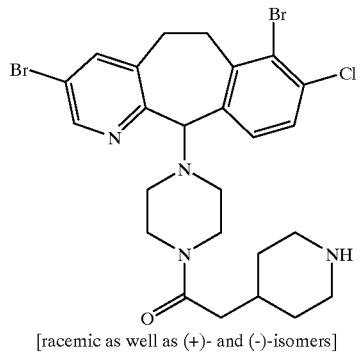

[racemic as well as (+)- and (−)-isomers]

Step A:

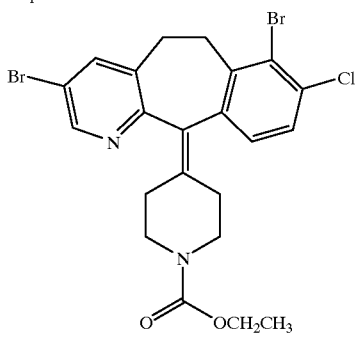

Combine 16.6 g (0.03 mole) of the product of Preparative Example 4, Step D, with a 3:1 solution of CH$_3$CN and water (212.65 mL CH$_3$CN and 70.8 mL of water) and stir the resulting slurry overnight at room temperature. Add 32.833 g (0.153 mole) of NaIO$_4$ and then 0.31 g (2.30 mmol) of RuO$_2$ and stir at room temperature give 1.39 g (69% yield) of the product. (The addition of RuO is accompanied by an exothermic reaction and the temperature climbs from 20° to 30° C.) Stir the mixture for 1.3 hrs. (temperature returned to 25° C. after about 30 min.), then filter to remove the solids and wash the solids with CH$_2$Cl$_2$. Concentrate the filtrate in vacuo to a residue and dissolve the residue in CH$_2$Cl$_2$. Filter to remove insoluble solids and wash the solids with CH$_2$Cl$_2$. Wash the filtrate with water, concentrate to a volume of about 200 mL and wash with bleach, then with water. Extract with 6 N HCl (aqueous). Cool the aqueous extract to 0° C. and slowly add 50% NaOH (aqueous) to adjust to pH=4 while keeping the temperature <30° C. Extract twice with CH$_2$Cl$_2$, dry over MgSO$_4$ and concentrate in vacuo to a residue. Slurry the residue in 20 mL of EtOH and cool to 0° C. Collect the resulting solids by filtration and dry the solids in vacuo to give 7.95 g of the product. $^1$H NMR (CDCl$_3$, 200 MHz): 8.7 (s, 1H); 7.85 (m, 6H); 7.5 (d, 2H); 3.45 (m, 2H); 3.15 (m, 2H).

Step B:

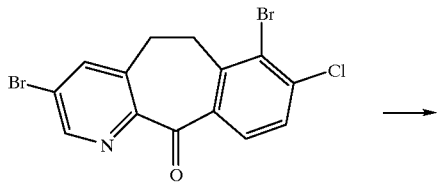

Combine 21.58 g (53.75 mmol) of the product of Step A and 500 mL of an anhydrous 1:1 mixture of EtOH and toluene, add 1.43 g (37.8 mmol) of NaBH$_4$ and heat the mixture at reflux for 10 min. Cool the mixture to 0° C., add 100 mL of water, then adjust to pH~4–5 with 1 M HCl (aqueous) while keeping the temperature <10° C. Add 250 mL of EtOAc and separate the layers. Wash the organic layer with brine (3×50 mL) then dry over Na$_2$SO$_4$. Concentrate in vacuo to a residue (24.01 g) and chromatograph the residue (silica gel, 30% hexane/CH$_2$Cl$_2$) to give the product. Impure fractions were purified by rechromatography. A total of 18.57 g of the product was obtained. $^1$H NMR (DMSO-d$_6$, 400 MHz): 8.5 (s, 1H); 7.9 (s, 1H); 7.5 (d of d, 2H); 6.2 (s, 1H); 6.1 (s, 1H); 3.5 (m, 1H); 3.4 (m, 1H); 3.2 (m, 2H).

Step C:

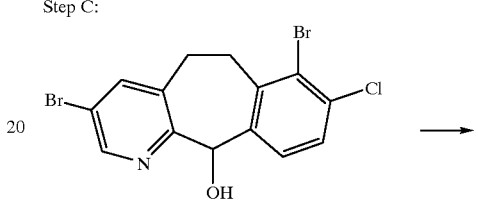

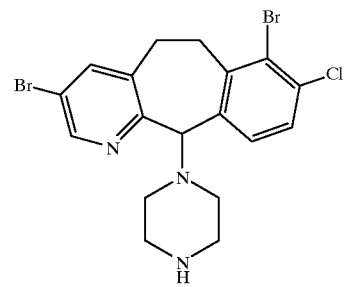

Combine 18.57 g (46.02 mmol) of the product of Step B and 500 mL of CHCl$_3$, then add 6.70 mL (91.2 mmol) of SOCl$_2$, and stir the mixture at room temperature for 4 hrs. Add a solution of 35.6 g (0.413 mole) of piperazine in 800 mL of THF over a period of 5 min. and stir the mixture for 1 hr. at room temperature. Heat the mixture at reflux overnight, then cool to room temperature and dilute the mixture with 1 L of CH$_2$Cl$_2$. Wash with water (5×200 mL), and extract the aqueous wash with CHCl$_3$ (3×100 mL). Combine all of the organic solutions, wash with brine (3×200 mL) and dry over MgSO$_4$. Concentrate in vacuo to a residue and chromatograph (silica gel, gradient of 5%, 7.5%, 10% MeOH/CH$_2$Cl$_2$+NH$_4$OH) to give 18.49 g of the title compound as a racemic mixture.

Step D - Separation of Enantiomers:

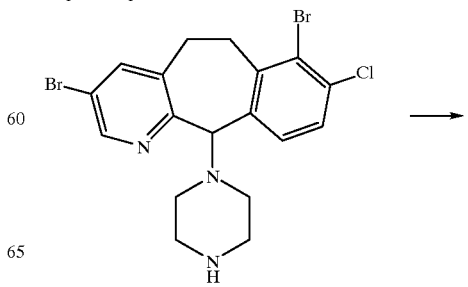

-continued

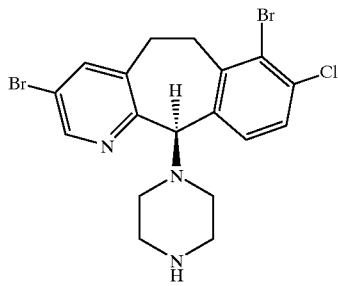

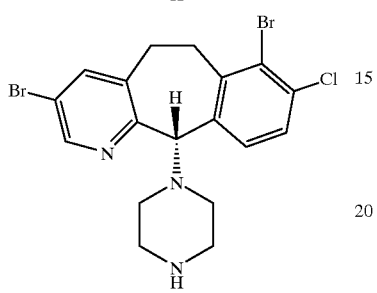

The racemic title compound of Step C is separated by preparative chiral chromatography (Chiralpack AD, 5 cm×50 cm column, flow rate 100 mL/min., 20% iPrOH/hexane+0.2% diethylamine), to give 9.14 g of the (+)-isomer and 9.30 g of the (−)-isomer.

Physical chemical data for (+)-isomer: m.p.=74.5°–77.5° C.; Mass Spec. MH$^+$=471.9; $[\alpha]_D^{25}$=+97.4° (8.48 mg/2 mL MeOH).

Physical chemical data for (−)-isomer: m.p.=82.9°–84.5° C.; Mass Spec. MH$^+$=471.8; $[\alpha]_D^{25}$=−97.4° (8.32 mg/2 mL MeOH).

Step E:

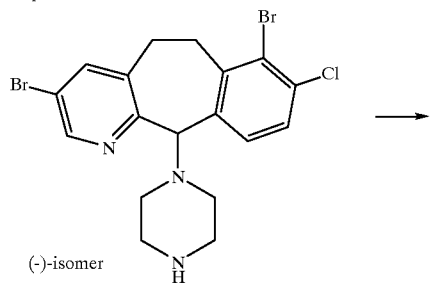

(−)-isomer

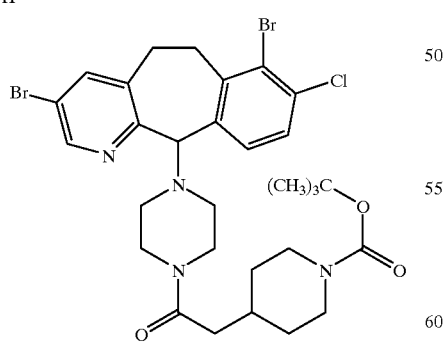

Combine 3.21 g (6.80 mmol) of the (−)-isomer product of Step D and 150 muL of anhydrous DMF. Add 2.15 g (8.8 mmol) of 1-N-t-butoxycarbonylpiperidinyl-4-acetic acid, 1.69 g (8.8 mmol) of DEC, 1.19 g (8.8 mmol) of HOBT and 0.97 mL (8.8 mmol) of N-methylmorpholine and stir the mixture at room temperature overnight. Concentrate in vacuo to remove the DMF and add 50 mL of saturated NaHCO$_3$ (aqueous). Extract with CH$_2$Cl$_2$ (2×250 mL), wash the extracts with 50 mL of brine and dry over MgSO$_4$. Concentrate in vacuo to a residue and chromatograph (silica gel, 2% MeOH/CH$_2$Cl$_2$+10% NH$_4$OH) to give 4.75 g of the product. m.p.=75.7°–78.5° C.; Mass Spec.: MH$^+$=697; $[\alpha]_D^{25}$=−5.5° (6.6 mg/2 mL MeOH).

Step F:

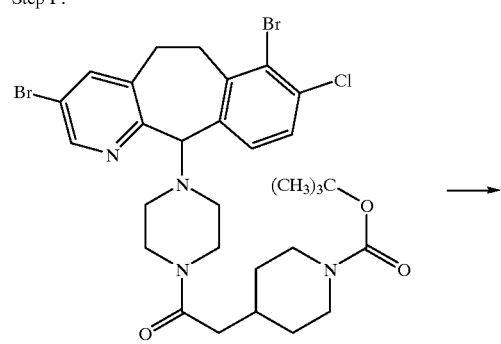

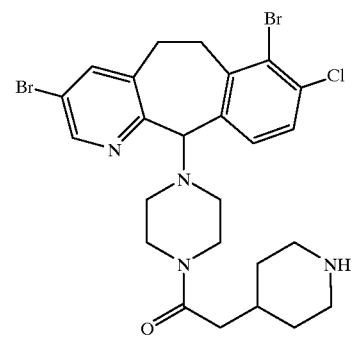

Combine 4.70 g (6.74 mmol) of the product of Step E and 30 mL of MeOH, then add 50 mL of 10% H$_2$SO$_4$/dioxane in 10 mL aliquots over a 1 hr. period. Pour the mixture into 50 mL of water and add 15 mL of 50% NaOH (aqueous) to adjust to pH~10–11. Filter to remove the resulting solids and extract the filtrate with CH$_2$Cl$_2$ (2×250 mL). Concentrate the aqueous layer in vacuo to remove the MeOH and extract again with 250 mL of CH$_2$Cl$_2$. Dry the combined extracts over MgSO$_4$ and concentrate in vacuo to give the product. m.p.=128.1°–131.5° C.; Mass Spec.: MH$^+$=597; $[\alpha]_D^{25}$=−6.02° (9.3 mg/2 mL MeOH).

PREPARATIVE EXAMPLE 7

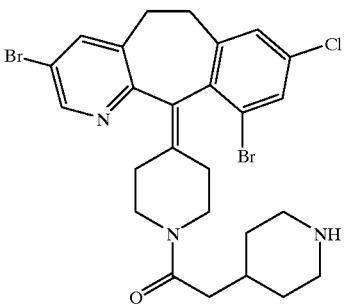

Step A:

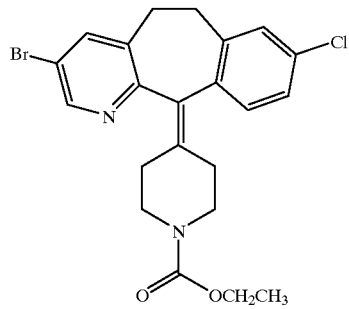

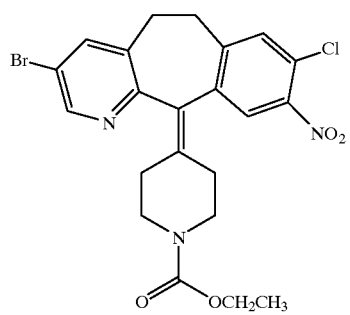

Combine 15 g (38.5 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 150 mL of concentrated H$_2$SO$_4$ at −5° C., then add 3.89 g (38.5 mmol) of KNO$_3$ and stir for 4 hours. Pour the mixture into 3 L of ice and basify with 50% NaOH (aqueous). Extract with CH$_2$Cl$_2$, dry over MgSO$_4$, then filter and concentrate in vacuo to a residue. Recrystallize the residue from acetone to give 6.69 g of the product. $^1$H NMR (CDCl$_3$, 200 MHz): 8.5 (s, 1H); 7.75 (s, 1H); 7.6 (s, 1H); 7.35 (s, 1H); 4.15 (q, 2H); 3.8 (m, 2H); 3.5–3.1 (m, 4H); 3.0–2.8 (m, 2H); 2.6–2.2 (m, 4H); 1.25 (t, 3H).

Step B:

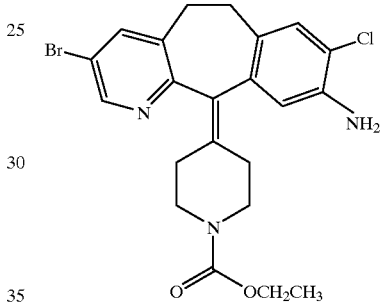

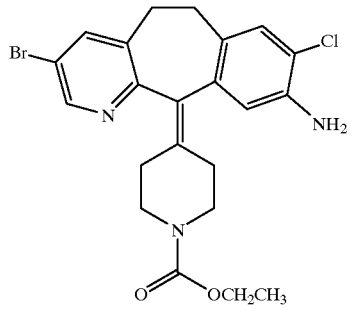

combine 6.69 g (13.1 mmol) of the product of Step A and 100 mL of 85% EtOH/water, then add 0.66 g (5.9 mmol) of CaCl$_2$ and 6.56 g (117.9 mmol) of Fe and heat the mixture at reflux overnight. Filter the hot reaction mixture through celite® and rinse the filter cake with hot EtOH. Concentrate the filtrate in vacuo to give 7.72 g of the product. Mass Spec.: MH$^+$=478.0.

Step C:

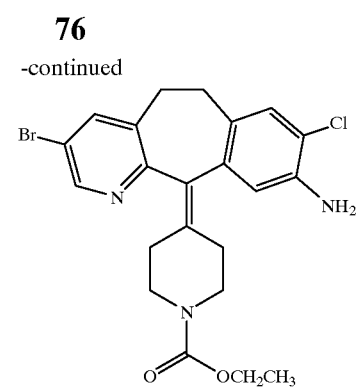

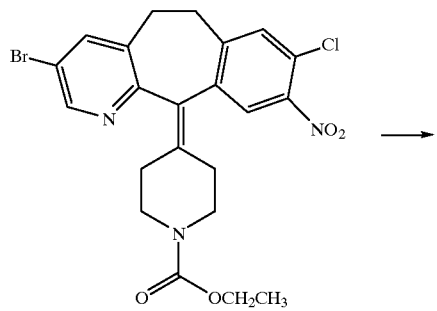

Combine 7.70 g of the product of Step B and 35 mL of HOAc, then add 45 mL of a solution of Br$_2$ in HOAc and stir the mixture at room temperature overnight. Add 300 mL of 1 N NaOH (aqueous), then 75 mL of 50% NaOH (aqueous) and extract with EtOAc. Dry the extract over MgSO$_4$ and concentrate in vacuo to a residue. Chromatograph the residue (silica gel, 20%–30% EtOAc/hexane) to give 3.47 g of the product (along with another 1.28 g of partially purified product). Mass Spec.: MH$^+$=555.9.

$^1$H NMR (CDCl$_3$, 300 MHz): 8.5 (s, 1H); 7.5 (s, 1H); 7.15 (s, 1H), 4.5 (s, 2H); 4.15 (m, 3H); 3.8 (br s, 2H); 3.4–3.1 (m,

4H); 9–2.75 (m, 1H); 2.7–2.5 (m, 2H); 2.4–b 2.2 (m, 2H); 1.25 (m, 3H).

Step D:

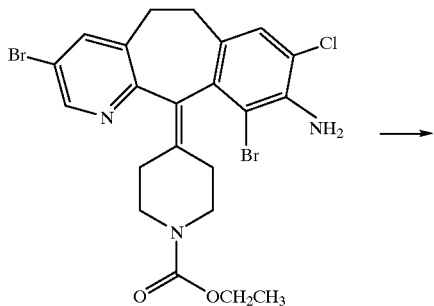

Combine 0.557 g (5.4 mmol) of t-butylnitrite and 3 mL of DMF, and heat the mixture at to 60°–70° C. Slowly add (dropwise) a mixture of 2.00 g (3.6 mmol) of the product of Step C and 4 mL of DMF, then cool the mixture to room temperature. Add another 0.64 mL of t-butylnitrite at 40° C. and reheat the mixture to 60°–70° C. for 0.5 hrs. Cool to room temperature and pour the mixture into 150 mL of water. Extract with $CH_2Cl_2$, dry the extract over $MgSO_4$ and concentrate in vacuo to a residue. Chromatograph the residue (silica gel, 10%–20% EtOAc/hexane) to give 0.74 g of the product. Mass Spec.: $MH^+$=541.0.

$^1H$ NMR (CDCl3, 200 MHz): 8.52 (s, 1H); 7.5 (d, 2H); 7.2 (s, 1H); 4.15 (q, 2H); 3.9–3.7 (m, 2H); 3.5–3.1 (m, 4H); 3.0–2.5 (m, 2H); 2.4–2.2 (m, 2H); 2.1–1.9 (m, 2H); 1.26 (t, 3H).

Step E:

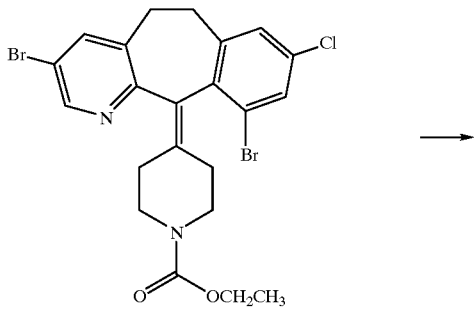

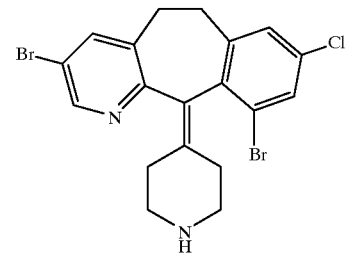

Combine 0.70 g (1.4 mmol) of the product of Step D and 8 mL of concentrated HCl (aqueous) and heat the mixture at reflux overnight. Add 30 mL of 1 N NaOH (aqueous), then 5 mL of 50% NaOH (aqueous) and extract with $CH_2Cl_2$. Dry the extract over $MgSO_4$ and concentrate in vacuo to give 0.59 g of the title compound. Mass Spec.: $M^+$=468.7. m.p.=123.9°–124.2° C.

Step F:

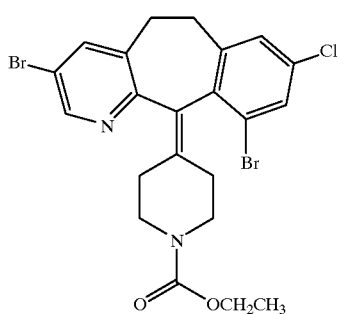

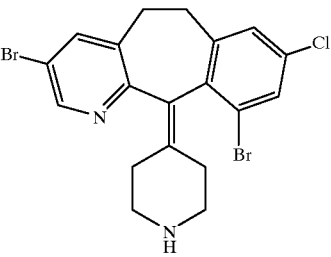

React 6.0 g (12.8 mmol) of the title compound from Step E and with 3.78 g (16.6 mmol) of 1-N-t-butoxycarbonylpiperidinyl-4-acetic acid using substantially the same procedures as described for Preparative Example 5, Step C, to give 8.52 g of the product. Mass Spec.: $MH^+$= 694.0 (FAB). $^1H$ NMR (CDCl$_3$, 200 MHz): 8.5 (d, 1H); 7.5 (d, 2H); 7.2 (d, 1H); 4.15–3.9 (m, 3H); 3.8–3.6 (m, 1H); 3.5–3.15 (m, 3H); 2.9 (d, 2H); 2.8–2.5 (m, 4H); 2.4–1.8 (m, 6H); 1.8–1.6 (br d, 2H); 1.4 (s, 9H); 1.25–1.0 (m, 2H).

Step G:

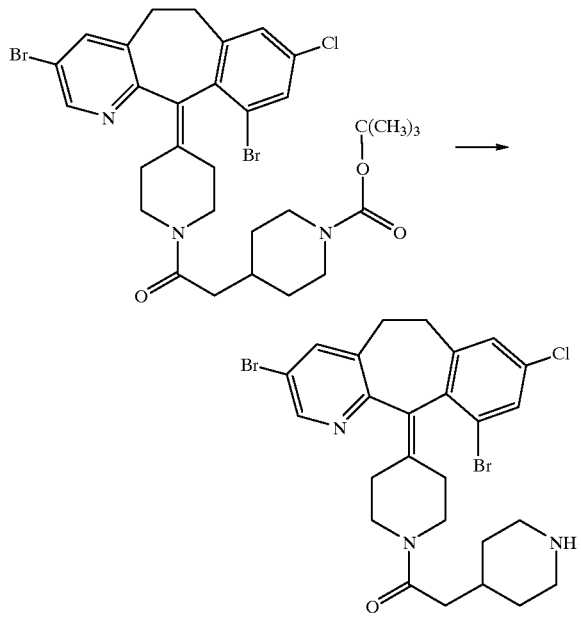

Combine 8.50 g of the product of Step F and 60 mL of $CH_2Cl_2$, then cool to 0° C. and add 55 mL of TFA. Stir the mixture for 3 h at 0° C., then add 500 mL of 1 N NaOH (aqueous) followed by 30 mL of 50% NaOH (aqueous). Extract with $CH_2Cl_2$, dry over $MgSO_4$ and concentrate in vacuo to give 7.86 g of the product. Mass Spec.: $M^+$=593.9 (FAB). $^1H$ NMR ($CDCl_3$, 200 MHz): 8.51 (d, 1H); 7.52 (d of d, 2H); 7.20 (d, 1H); 4.1–3.95 (m, 2H); 3.8–3.65 (m, 2H); 3.5–3.05 (m, 5H); 3.0–2.5 (m, 6H); 2.45–1.6 (m, 6H);1.4–1.1 (m, 2H).

PREPARATIVE EXAMPLE 8

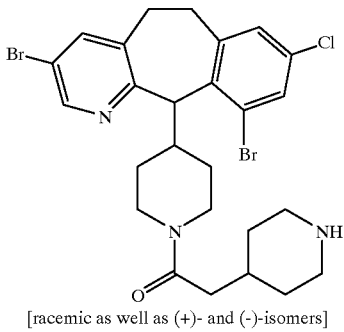

[racemic as well as (+)- and (-)-isomers]

Step A:

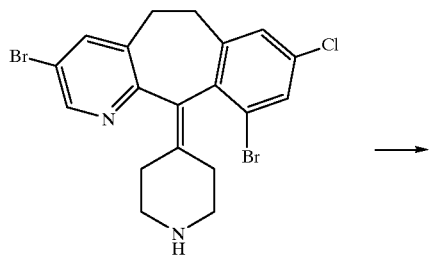

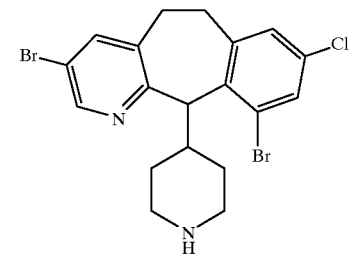

-continued

Prepare a solution of 8.1 g of the title compound from Preparative Example 7, Step E, in toluene and add 17.3 mL of a 1M solution of DIBAL in toluene. Heat the mixture at reflux and slowly add (dropwise) another 21 mL of 1 M DIBAL/toluene solution over a period of 40 min. Cool the reaction mixture to about 0° C. and add 700 mL of 1 M HCl (aqueous). Separate and discard the organic phase. Wash the aqueous phase with $CH_2Cl_2$, discard the extract, then basify the aqueous phase by adding 50% NaOH (aqueous). Extract with $CH_2Cl_2$, dry the extract over $MgSO_4$ and concentrate in vacuo to give 7.30 g of the title compound, which is a racemic mixture of enantiomers.

Step B - Separation of Enantiomers:

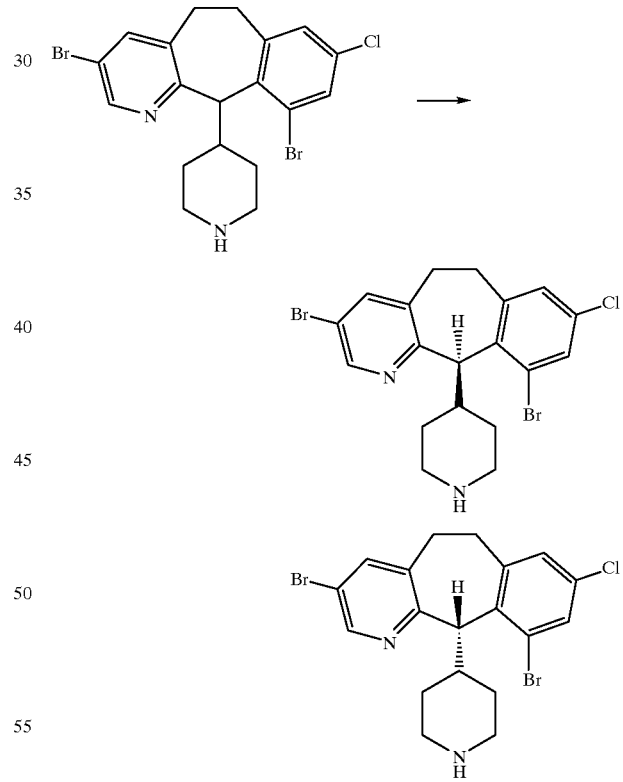

The racemic title compound of Step A is separated by preparative chiral chromatography (Chiralpack AD, 5 cm×50 cm column, using 20% iPrOH/hexane +0.2% diethylamine), to give the (+)-isomer and the (-)-isomer of the title compound.

Physical chemical data for (+)-isomer: m.p.=148.8° C.; Mass Spec. $MH^+$=469; $[\alpha]_D^{25}$=+65.6° (12.93 mg/2 mL MeOH).

Physical chemical data for (−)-isomer: m.p.=112° C.; Mass Spec. MH+=469; $[\alpha]_D^{25}=-65.2°$ (3.65 mg/2 mL MeOH).

Step C:

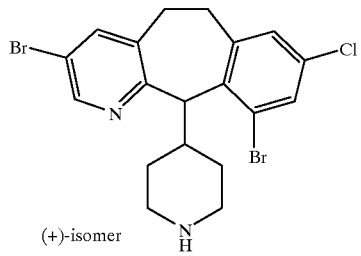

(+)-isomer

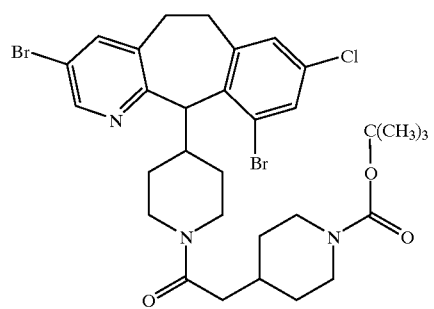

React 1.33 g of the (+)-isomer of the title compound of Preparative Example 8, Step B, with 1.37 g of 1-N-t-butoxycarbonylpiperidinyl-4-acetic acid using substantially the same procedures as described for Preparative Example 5, Step C, to give 2.78 g of the product. Mass Spec.: MH+= 694.0 (FAB); $[\alpha]_D^{25}=+34.1°$ (5.45 mg/2 mL, MeOH).

Step D:

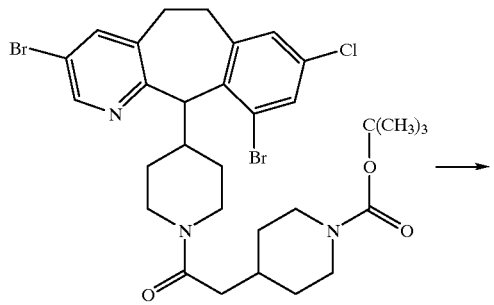

Treat 2.78 g of the product of Step C via substantially the same procedure as described for Preparative Example 5, Step D, to give 1.72 g of the product. m.p.=104.1° C.; Mass Spec.: MH+=594; $[\alpha]_D^{25}=+53.4°$ (11.42 mg/2 mL, MeOH).

PREPARATIVE EXAMPLE 9

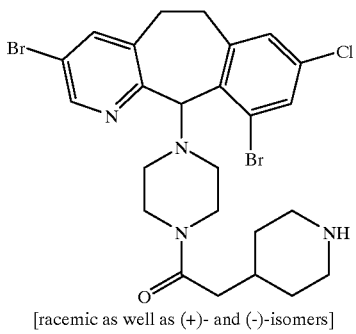

[racemic as well as (+)- and (−)-isomers]

Step A:

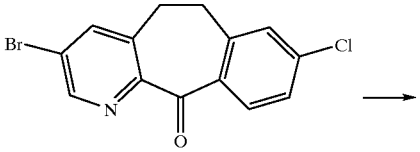

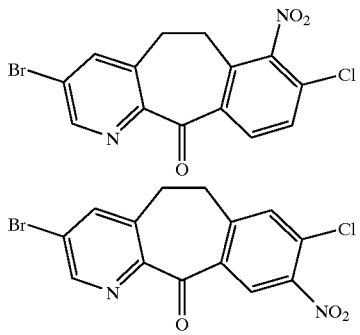

Combine 40.0 g (0.124 mole) of the starting ketone and 200 mL of $H_2SO_4$ and cool to 0° C. Slowly add 13.78 g (0.136 mole) of $KNO_3$ over a period of 1.5 hrs., then warm to room temperature and stir overnight. Work up the reaction using substantially the same procedure as described for Preparative Example 4, Step A. Chromatograph (silica gel, 20%, 30%, 40%, 50% EtOAc/hexane, then 100% EtOAc) to give 28 g of the 9-nitro product, along with a smaller quantity of the 7-nitro product and 19 g of a mixture of the 7-nitro and 9-nitro Step B:

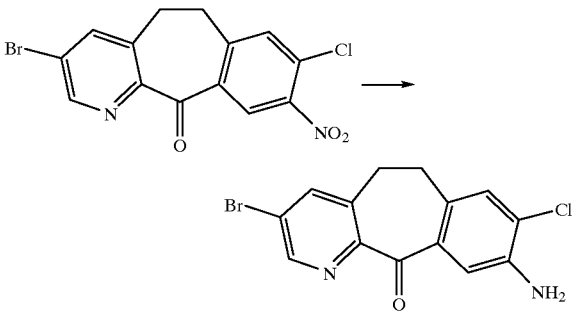

React 28 g (76.2 mmol) of the 9-nitro product of Step A, 400 mL of 85% EtOH/water, 3.8 g (34.3 mmol) of $CaCl_2$ and 38.28 g (0.685 mole) of Fe using substantially the same procedure as described for Preparative Example 4, Step C, to give 24 g of the product Step C:

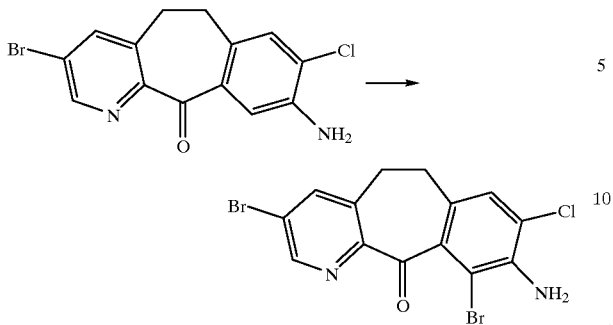

Combine 13 g (38.5 mmol) of the product of Step B, 140 mL of HOAc and slowly add a solution of 2.95 mL (57.8 mmol) of Br$_2$ in 10 mL of HOAc over a period of 20 min. Stir the reaction mixture at room temperature, then concentrate in vacuo to a residue. Add CH$_2$Cl$_2$ and water, then adjust to pH=8–9 with 50% NaOH (aqueous). Wash the organic phase with water, then brine and dry over Na$_2$SO$_4$. Concentrate in vacuo to give 11.3 g of the product.

Step D:

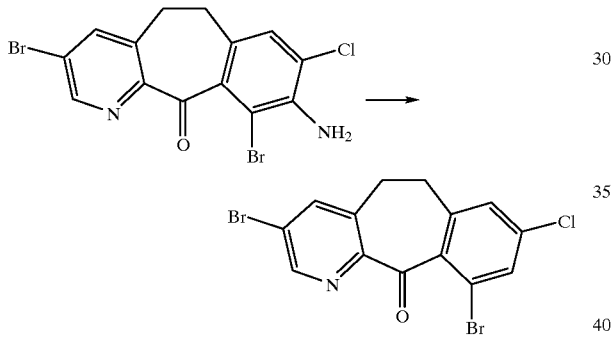

Cool 100 mL of concentrated HCl (aqueous) to 0° C., then add 5.61 g (81.4 mmol) of NaNO$_2$ and stir for 10 min. Slowly add (in portions) 11.3 g (27.1 mmol) of the product of Step C and stir the mixture at 0°–3° C. for 2.25 hrs. Slowly add (dropwise) 180 mL of 50% H$_3$PO$_2$ (aqueous) and allow the mixture to stand at 0° C. overnight. Slowly add (dropwise) 150 mL of 50% NaOH over 30 min., to adjust to pH=9, then extract with CH$_2$Cl$_2$. Wash the extract with water, then brine and dry over Na$_2$SO$_4$. Concentrate in vacuo to a residue and chromatograph (silica gel, 2% EtOAc/CH$_2$Cl$_2$) to give 8.6 g of the product.

Step E:

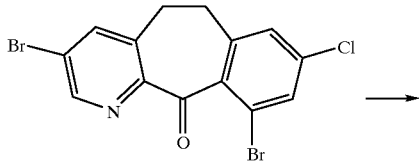

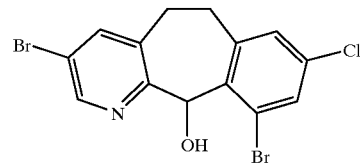

Combine 8.6 g (21.4 mmol) of the product of Step D and 300 mL of MeOH and cool to 0°–2° C. Add 1.21 g (32.1 mmol) of NaBH$_4$ and stir the mixture at ~0° C. for 1 hr. Add another 0.121 g (3.21 mmol) of NaBH$_4$, stir for 2 hr. at 0° C., then let stand overnight at 0° C. Concentrate in vacuo to a residue then partition the residue between CH$_2$Cl$_2$ and water. Separate the organic phase and concentrate in vacuo (50° C.) to give 8.2 g of the product.

Step F:

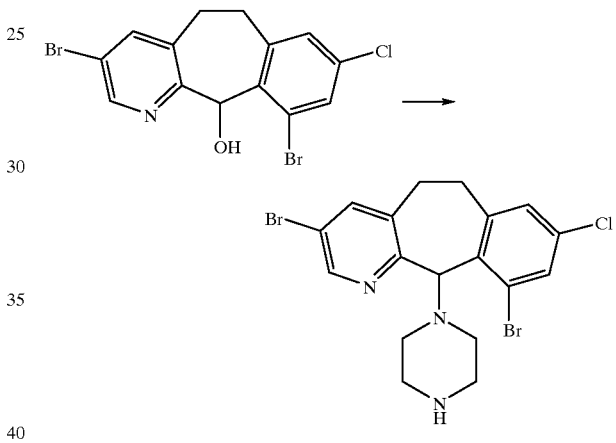

Combine 8.2 g (20.3 mmol) of the product of Step E and 160 mL of CH$_2$Cl$_2$, cool to 0° C., then slowly add (dropwise) 14.8 mL (203 mmol) of SOCl$_2$ over a 30 min. period. Warm the mixture to room temperature and stir for 4.5 hrs., then concentrate in vacuo to a residue, add CH$_2$Cl$_2$ and wash with 1 N NaOH (aqueous) then brine and dry over Na$_2$SO$_4$. Concentrate in vacuo to a residue, then add dry THF and 8.7 g (101 mmol) of piperazine and stir at room temperature overnight. Concentrate in vacuo to a residue, add CH$_2$Cl$_2$, and wash with 0.25 N NaOH (aqueous), water, then brine. Dry over Na$_2$SO$_4$ and concentrate in vacuo to give 9.46 g of the crude product. Chromatograph (silica gel, 5% MeOH/CH$_2$Cl$_2$+NH$_3$) to give 3.59 g of the title compound, as a racemate. $^1$H NMR (CDCl$_3$, 200 MHz): 8.43 (d, 1H); 7.55 (d, 1H); 7.45 (d, 1H); 7.11 (d, 1H); 5.31 (s, 1H); 4.86–4.65 (m, 1H); 3.57–3.40 (m, 1H); 2.98–2.55 (m, 6H); 2.45–2.20 (m, 5H).

Step G - Separation of Enantiomers:

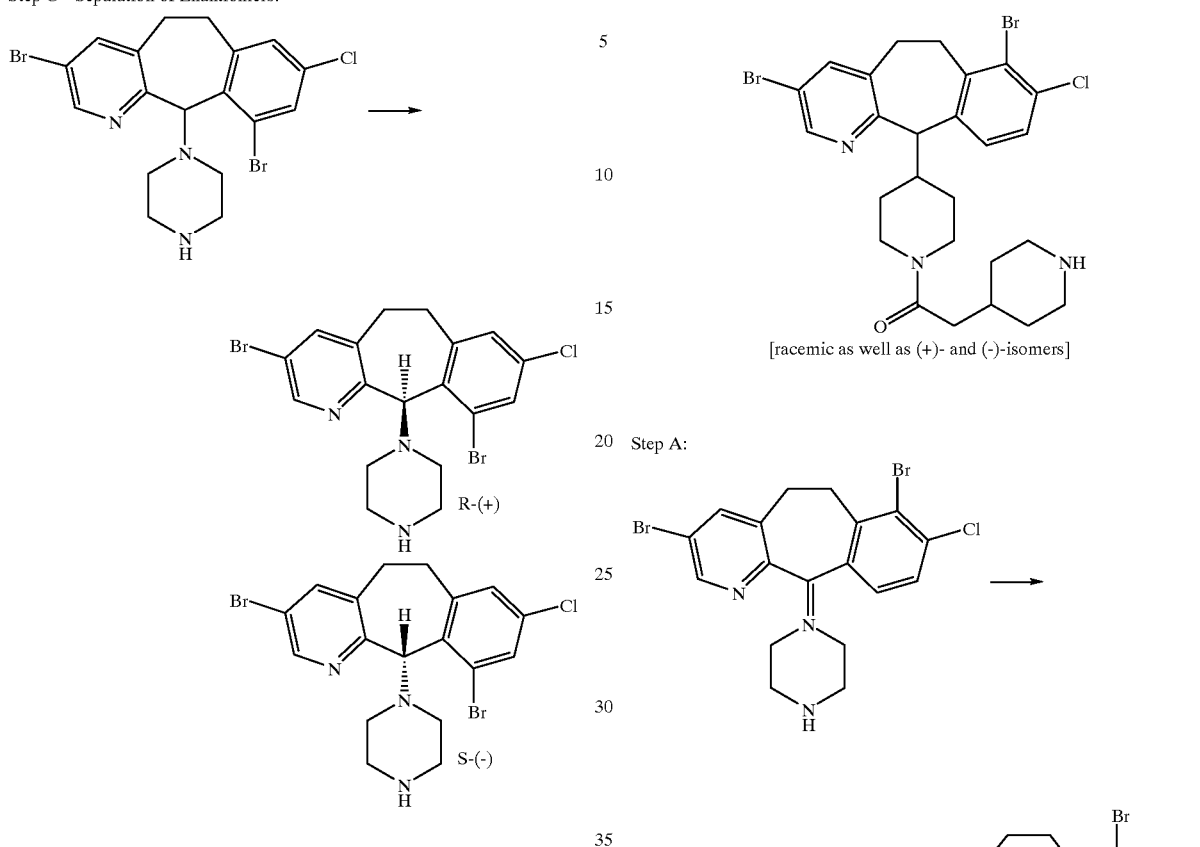

The racemic title compound from Step F (5.7 g) is chromatographed as described for Preparative Example 6, Step D, using 30% iProH/hexane+0.2% diethylamine, to give 2.88 g of the R-(+)-isomer and 2.77 g of the S-(−)-isomer of the title a compound.

Physical chemical data for the R-(+)-isomer: Mass Spec. MH$^+$=470.0; [$\alpha_D^{25}$]=+12.1° (10.9 mg/2 mL MeOH).

Physical chemical data for the S-(−)-isomer: Mass Spec. MH$^+$=470.0; [$\alpha$]$_D^{25}$=13.2° (11.51 mg/2 mL MeOH).

Step H:

Following essentially the same procedure as Preparative Example 5, Steps C and D, the racemic title compound of Preparative Example 9 is obtained from the racemic compound of Step F. Similarly, using the (−)- or (+)-isomer from Step G, the (−)- or (+)-isomer of the title compound of Preparative Example 9 is obtained, respectively.

PREPARATIVE EXAMPLE 10

[racemic as well as (+)- and (−)-isomers]

Step A:

Combine 13 g (33.3 mmol) of the title compound from Preparative Example 4, Step E, and 300 mL of toluene at 20° C., then add 32.5 mL (32.5 mmol) of a 1 M solution of DIBAL in toluene. Heat the mixture at reflux for 1 hr., cool to 20° C., add another 32.5 mL of 1 M DIBAL solution and heat at reflux for 1 hr. Cool the mixture to 20° C. and pour it into a mixture of 400 g of ice, 500 mL of EtOAc and 300 mL of 10% NaOH (aqueous). Extract the aqueous layer with CH$_2$Cl$_2$ (3×200 mL), dry the organic layers over MgSO$_4$, then concentrate in vacuo to a residue. Chromatograph (silica gel, 12% MeOH/CH$_2$Cl$_2$+4% NH$_4$OH) to give 10.4 g of the title compound as a racemate. Mass Spec.: MH$^+$=469 (FAB). partial $^1$H NMR (CDCl$_3$, 400 MHz): 8.38 (s, 1H); 7.57 (s, 1H); 7.27 (d, 1H); 7.06 (d, 1H); 3.95 (d, 1H).

Step B - Separation of Enantiomers:

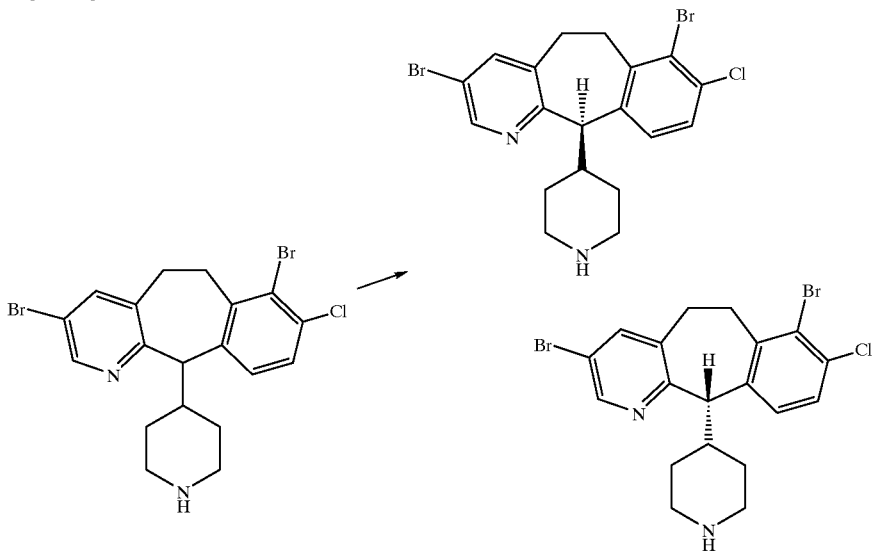

The racemic title compound of Step A is separated by preparative chiral chromatography (Chiralpack AD, 5 cm×50 cm column, using 5% iPrOH/hexane +0.2% diethylamine), to give the (+)-isomer and the (−)-isomer of the title compound.

Physical chemical data for (+)-isomer: Mass Spec. MH$^+$= 469 (FAB); $[\alpha]^{25}_D$=+43.5° (c=0.402, EtOH); partial $^1$H NMR (CDCl$_3$, 400 MHz): 8.38 (s, 1H); 7.57 (s, 1H); 7.27 (d, 1H); 7.05 (d, 1H); 3.95 (d, 1H).

Physical chemical data for (−)-isomer: Mass Spec. MH$^+$= 469 (FAB); $[\alpha]^{25}_D$=−41.8° (c=0.328 EtOH); partial $^1$H NMR (CDCl$_3$, 400 MHz): 8.38 (s, 1H); 7.57 (s, 1H); 7.27 (d, 1H); 7.05 (d, 1H); 3.95 (d, 1H).

Step C:

Following the procedure of Preparative Example 9, Step H, the racemic compound, the (+)-isomer or the (−)-isomer of the title compound of Preparative Example 10 can be obtained.

PREPARATIVE EXAMPLE 11

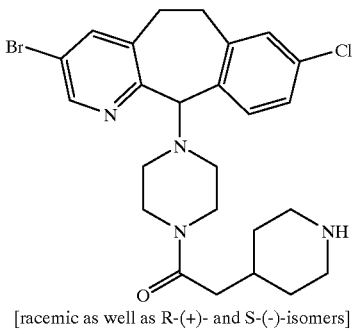

[racemic as well as R-(+)- and S-(−)-isomers]

The compound

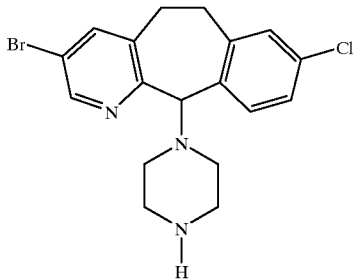

is prepared according to the procedures of Preparative Example 40 of WO 95/10516 (published Apr. 20, 1995), by following the procedures described in Example 193 of WO 95/10516.

The (+)- and (−)-isomers can be separated by following essentially the same procedure as Step D of Preparative Example 6.

Physical chemical data for the R-(+)-isomer: $^{13}$C NMR (CDCl$_3$): 155.8 (c); 146.4 (CH); 140.5 (CH); 140.2 (C); 136.2 (C); 135.3 (C); 133.4 (C); 132.0 (CH); 129.9 (CH); 125.6 (CH); 119.3 (C); 79.1 (CH); 52.3 (CH$_2$); 52.3 (CH); 45.6 (CH$_2$); 45.6 (CH$_2$); 30.0 (CH$_2$); 29.8 (CH$_2$). $[\alpha]^{25}_D$=+ 25.8° (8.46 mg/2 mL MeOH).

Physical chemical data for the S-(−)-isomer: $^{13}$C NMR (CDCl$_3$): 155.9 (C); 146.4 (CH); 140.5 (CH); 140.2 (C); 136.2 (C); 135.3 (C); 133.3 (C); 132.0 (CH); 129.9 (CH); 125.5 (CH); 119.2 (C); 79.1 (CH); 52.5 (CH$_2$); 52.5 (CH); 45.7 (CH$_2$); 45.7 (CH$_2$); 30.0 (CH$_2$); 29.8 (CH$_2$). $[\alpha]^{25}_D$=− 27.9° (8.90 mg/2 mL MeOH).

Following essentially the same procedure as Preparative Example 5, Steps C and D, the racemic compound, (+)-isomer or (−)-isomer of the title compound of Preparative Example 11 can be obtained from the corresponding racemic compound, (+)-isomer or (−)-isomer of the compound

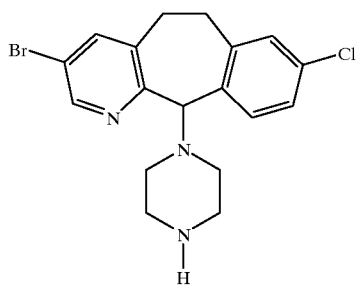

PREPARATIVE EXAMPLE 12

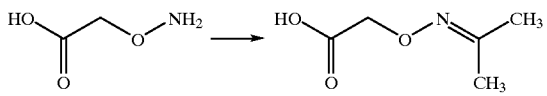

Follow a procedure outlined in Collect. Czech. Chem. Comm. (1990) 55, 2086. Dissolve 0.2 g (0.915 mmol) of (aminooxy)acetic acid hemihydrochloride and 0.2 g (3 mmol) of a acetone in 2 mL of pyridine and allow to stand for 18 hr. Concentrate under vacuum and partition the residue between ethyl acetate and 1 N Hcl. Dry the organic layer over magnesium sulfate and concentrate under vacuum to give a white solid mp=77.3–78° C.

PREPARATIVE EXAMPLE 13

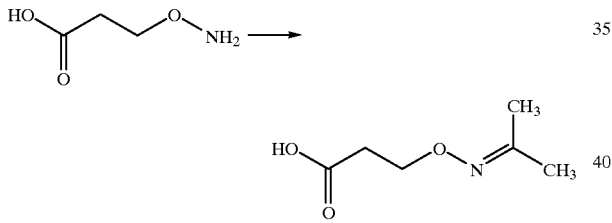

Follow the procedure of Preparative Example 12 but use 2-aminooxypropionic acid hemihydrochloride instead of (aminooxy)acetic acid to obtain the product as a colorless oil.

PREPARATIVE EXAMPLE 14

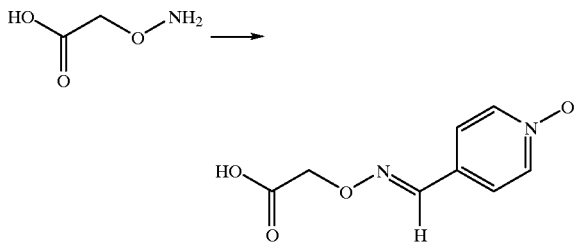

Follow the procedure of Preparative Example 12 but use 4-pyridinecarboxaldehyde N-oxide instead of acetone to obtain the product that was recrystallized from water to give a white solid mp=227–228° C.

PREPARATIVE EXAMPLE 15

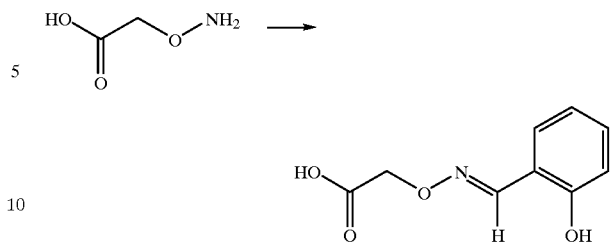

Follow the procedure of Preparative Example 12 but use 2-hydroxybenzaldehyde instead of acetone to obtain the product as a white solid mp=152–153.5° C.

EXAMPLE 1

(28.0) ⟶

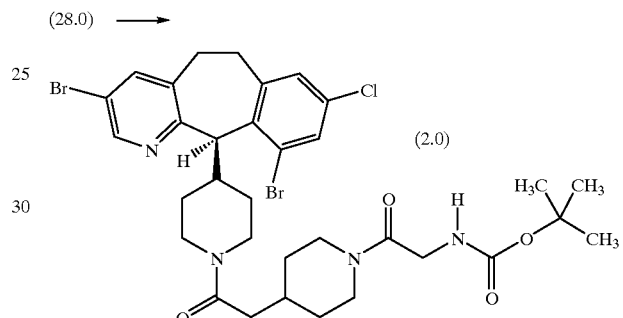

The compound of Formula 28.0

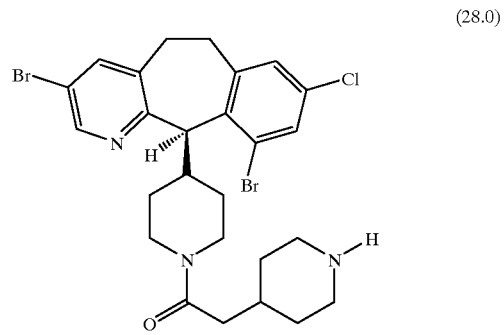

(Preparative Example 8) (0.149 g, 0.25 mmol) was combined with 1-hydroxybenzotriazole hydrate (0.067 g, 0.5 mmol), 1-(3-dimethylaminopropyl)-3-ethylcarbodiimide hydrochloride (0.096 g, 0.5 mmol), N-BOC-glycine (0.087 g, 0.5 mmol) and anhydrous dimethylformamide (5 mL) and the resulting mixture was stirred at room temperature under nitrogen overnight. Concentration in vacuo provided an oil which was diluted with dichloromethane, washed with 1M hydrochloric acid and 1 M aqueous sodium hydroxide, then dried over anhydrous magnesium sulfate. Filtration and concentration in vacuo afforded the compound of Formula 2.0 (+-isomer)(0.16 g, 85%, mp 116–123° C.).

EXAMPLE 2

(2.0) →

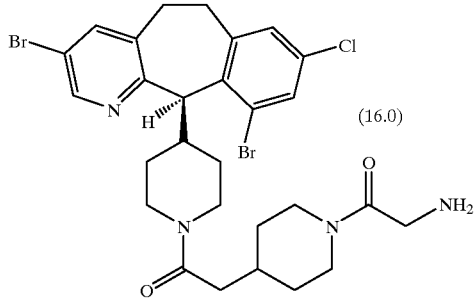

(16.0)

To the compound of Formula 2.0 (Example 1) (0.145 g) dissolved in anhydrous dichloromethane (10 mL) was added trifluoroacetic acid (2 mL) and the resulting solution was stirred at room temperature for 1 hour. 50% Aqueous sodium hydroxide was added slowly followed by dichloromethane and brine. The mixture was shaken well, the organic phase was separated and dried over anhydrous magnesium sulfate. Filtration and concentration in vacuo afforded the compound of Formula 16.0 (+-isomer) (0.086 g, 68%, mp 131–138° C.).

EXAMPLE 3

(28.0) →

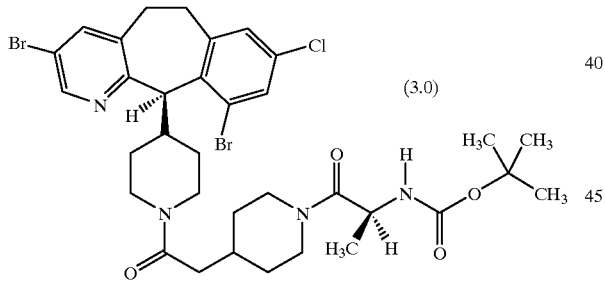

(3.0)

The compound of Formula 28.0 (Preparative Example 8) (0.10 g, 0.17 mmol) was combined with 1-hydroxybenzotriazole hydrate (0.045 g, 0.34 mmol), 1-(3-dimethylaminopropyl)-3-ethylcarbodiimide hydrochloride (0.064 g, 0.34 mmol), N-tert-butoxycarbonyl-L-alanine (0.064 g, 0.34 mmol) and anhydrous dimethylformamide (10 mL) and the resulting mixture was stirred at room temperature under nitrogen overnight. Concentration in vacuo provided an oil which was diluted with dichloromethane, washed with 1M hydrochloric acid and 1 M aqueous sodium hydroxide, then dried over anhydrous magnesium sulfate. Filtration and concentration in vacuo afforded the compound of Formula 3.0 (+-isomer) (0.095 g, 74%, mp 135–142° C.).

EXAMPLE 4

(3.0) →

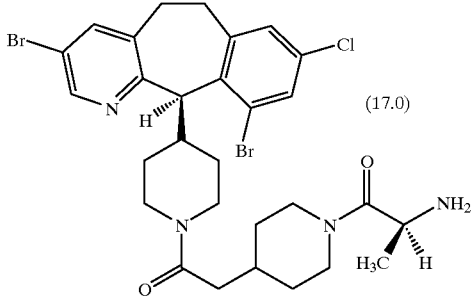

(17.0)

To the compound of Formula 3.0 (Example 3) (0.09 g) dissolved in anhydrous dichloromethane (10 mL) was added trifluoroacetic acid (1 mL) and the resulting solution was stirred at room temperature for 1 hour. 50% Aqueous sodium hydroxide was added slowly followed by dichloromethane and brine. The mixture was shaken well, the organic phase was separated and dried over anhydrous magnesium sulfate. Filtration and concentration in vacuo afforded the compound of Formula 17.0 (+-isomer) (0.053 g, 68%, mp 122.7–128° C.).

EXAMPLE 5

(28.0) →

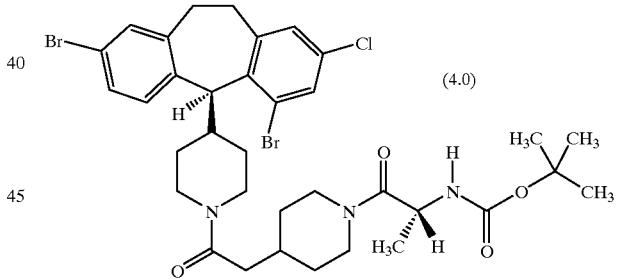

(4.0)

The compound of Formula 28.0 (Preparative Example 8) (0.10 g, 0.17 mmol) was combined with 1-hydroxybenzotriazole hydrate (0.045 g, 0.34 mmol), 1-(3-dimethylaminopropyl)-3-ethylcarbo-diimide hydrochloride (0.064 g, 0.34 mmol), N-tert-butoxy-carbonyl-D-alanine (0.064 g, 0.34 mmol) and anhydrous dimethylformamide (10 mL) and the resulting mixture was stirred at room temperature under nitrogen overnight. Concentration in vacuo provided an oil which was diluted with dichloromethane, washed with 1M hydrochloric acid and 1 M aqueous sodium hydroxide, then dried over anhydrous magnesium sulfate. Filtration and concentration in vacuo afforded the compound of Formula 4.0 (+-isomer) (0.104 g, 81%, mp 135.1–142.3° C.).

EXAMPLE 6

(4.0) →

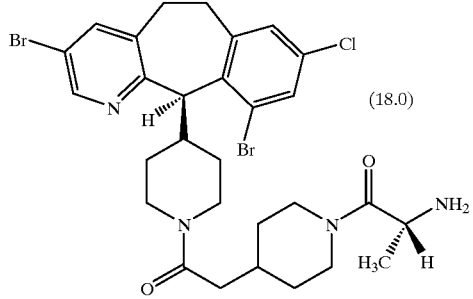

(18.0)

To the compound of Formula 4.0 (Example 5) (0.10 g) dissolved in anhydrous dichloromethane (10 mL) was added trifluoroacetic acid (1 mL) and the resulting solution was stirred at room temperature for 1 hour. 50% Aqueous sodium hydroxide was added slowly followed by dichloromethane and brine. The mixture was shaken well, the organic phase was separated and dried over anhydrous magnesium sulfate. Filtration and concentration in vacuo afforded the compound of formula 18.0 (+-isomer) (0.056 g, 64%, mp 103° C. (DEC)).

EXAMPLE 7

(28.0) →

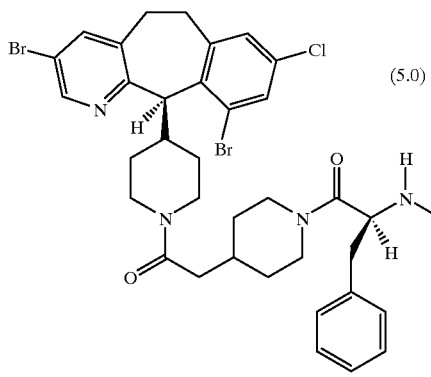

(5.0)

The compound of Formula 5.0 (+-isomer) was prepared, according to procedures similar to those of Examples 1, 3, and 5, by reacting the compound of Formula 28.0 (Preparative Example 8) with the amino acid N-tert-butoxycarbonyl-L-phenylalanine. Yield: 76%, mp: 128.6–134° C.

EXAMPLE 8

(28.0) →

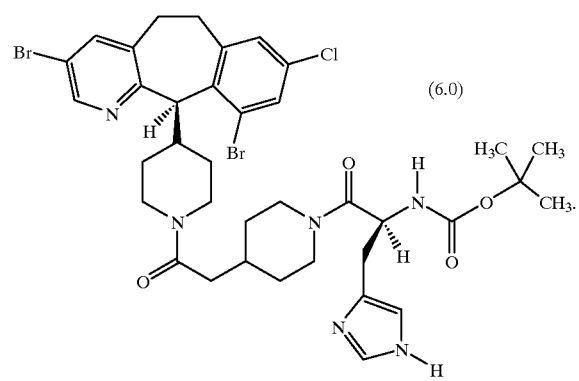

(6.0)

The compound of Formula 6.0 (+-isomer) was prepared, according to procedures similar to those of Examples 1, 3, and 5, by reacting the compound of Formula 28.0 (Preparative Example 8) with the amino acid N-(alpha)-tert-butoxycarbonyl-L-histidine. Yield: 32%, mp: 96.0–99.7° C.

EXAMPLE 9

(28.0) →

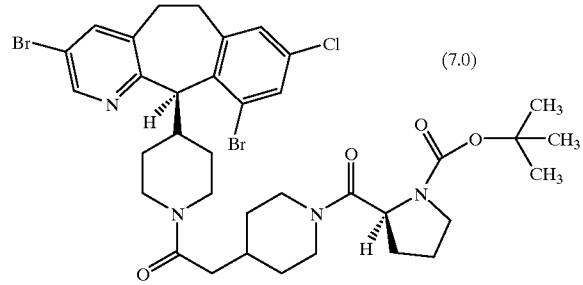

(7.0)

The compound of Formula 7.0 (+-isomer) was prepared, according to procedures similar to those of Examples 1, 3, and 5, by reacting the compound of Formula 28.0 (Preparative Example 8) with the amino acid N-(alpha)-tert-butoxycarbonyl-L-proline. Yield: 52%, mp: 110° C.

EXAMPLE 10

(5.0) →

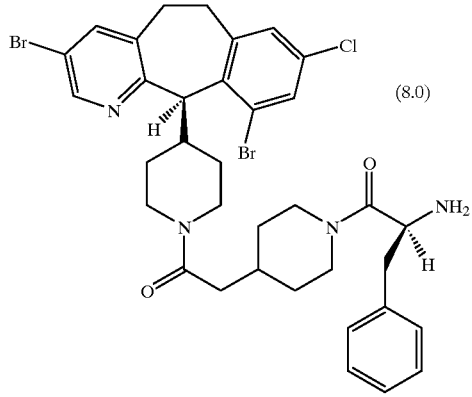

(8.0)

The compound of Formula 8.0 (+-isomer) was prepared, according to procedures similar to those of Examples 2, 4, and 6, from the compound of Formula 5.0 (Example 7). Yield: 70%, mp: 116–119° C.

EXAMPLE 11

(6.0) ⟶

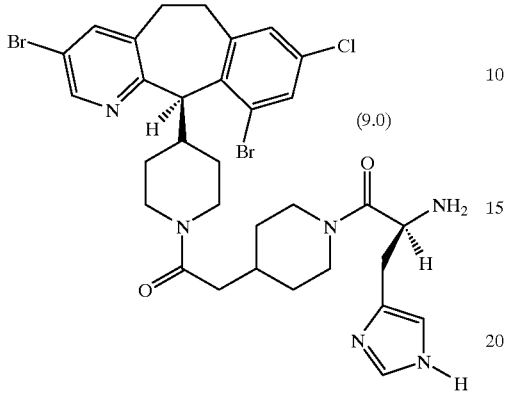

The compound of Formula 9.0 (+-isomer) was prepared, according to procedures similar to those of Examples 2, 4, and 6, from the compound of Formula 6.0 (Example 8). Yield: 51%, mp: 101° C.

EXAMPLE 12

(7.0) ⟶

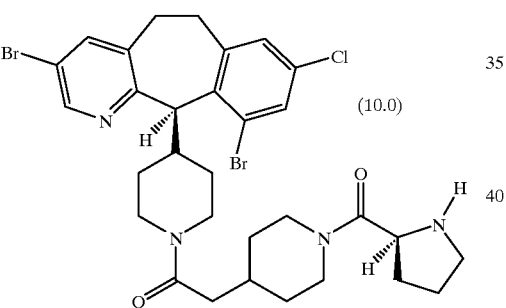

The compound of Formula 10.0 (+-isomer) was prepared, according to procedures similar to those of Examples 2, 4, and 6, from the compound of Formula 7.0 (Example 9). Yield: 46%, mp: 131.6° C.

EXAMPLE 13

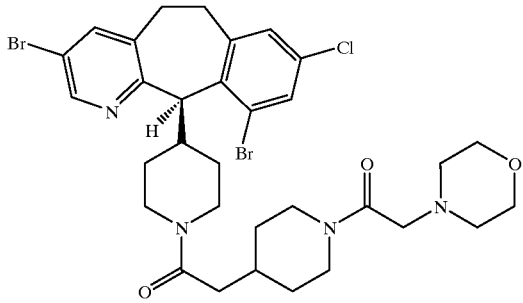

STEP A:

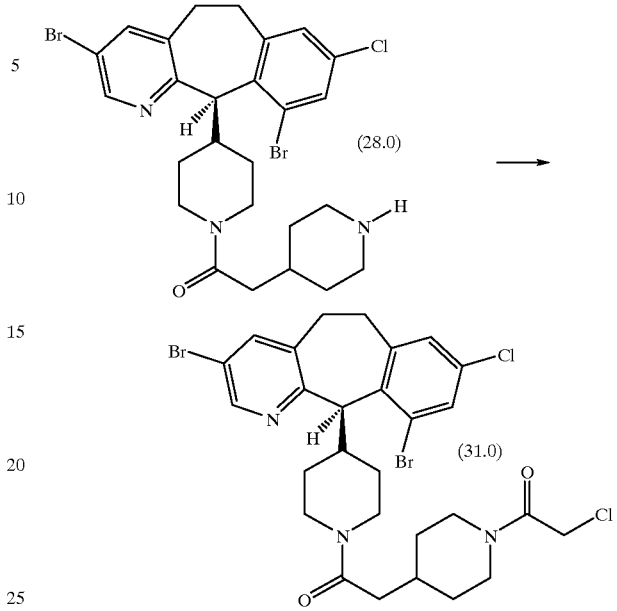

To the compound of Formula 28.0 (Preparative Example 8) (0.51 g, 0.85 mmol) and triethylamine (0.18 mL, 1.3 mmol) dissolved in anhydrous dichloromethane (50 mL) was added ClCH$_2$C(O)Cl (chloroacetyl chloride) (0.28 mL, 1.2 eq) dissolved in dichloromethane (10 mL) at 0° C. After stirring for 1.5 hours, 1 M hydrochloric acid was added and the mixture was shaken. The organic phase was separated and washed with 1 N aqueous sodium hydroxide, then brine, and dried over anhydrous magnesium sulfate. Filtration and concentration in vacuo afforded the compound of Formula 31.0 (0.58 g, 100%, mp 124.0–134.5° C.).

STEP B
(31.0) ⟶

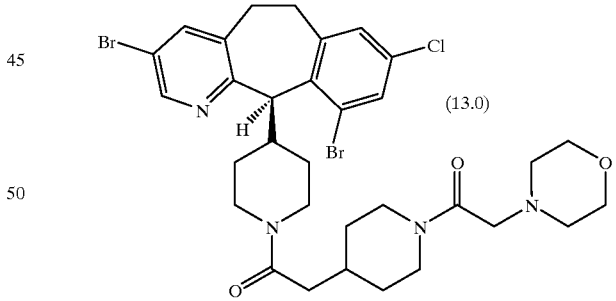

The compound of Formula 31.0 (0.12 g, 0.18 mmol), morpholine (5 mL) and anhydrous sodium carbonate (0.038 g, 2 eq) were stirred at 130° C. overnight. After concentration in vacuo, the residue was diluted with dichloromethane, washed with water and dried over anhydrous magnesium sulfate. Filtration and concentration in vacuo afforded a yellow residue (0.17 g) which was purified by preparative plate chromatography (silica gel) using 5% methanol-dichloromethane and concentrated ammonium hydroxide to provide the compound of Formula 13.0 (0.096 g, 75%, mp 116.6° C.).

EXAMPLE 14

(31.0) →

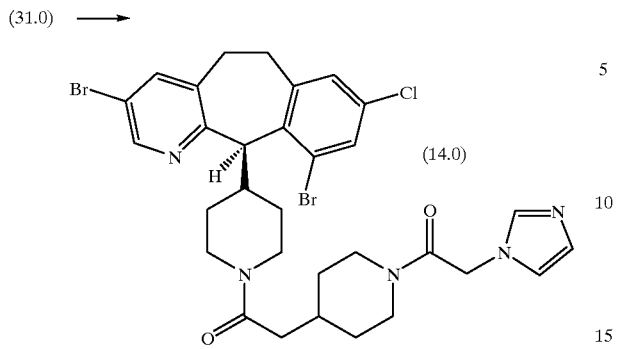

(14.0)

The compound of Formula 31.0 (Example 13) (0.12 g, 0.18 mmol), anhydrous dimethylformamide (10 mL), imidazole 10.037 g, 0.54 mmol) and anhydrous sodium carbonate (0.057 g, 0.54 mmol) were stirred at 130° C. overnight. The mixture was cooled to room temperature, diluted with water, filtered and the solids washed with water. The solids were diluted with dichloromethane, washed with water and then with 1 N aqueous sodium hydroxide. The organic phase was separated, dried over anhydrous magnesium sulfate, filtered and concentrated in vacuo to afford a solid (0.084 g) which was purified by preparative plate chromatography (silica gel) using 5% methanol-dichloromethane and concentrated ammonium hydroxide to provide the compound of Formula 14.0 (0.06 g, 48%, mp 148.9° C.).

EXAMPLE 15

(28.0) →

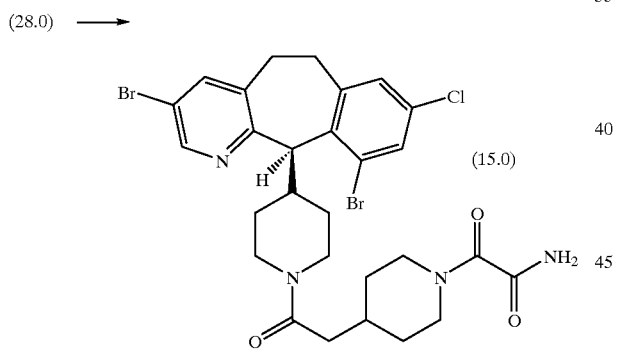

(15.0)

The compound of Formula 28.0 (Preparative Example 8) (0.21 g, 0.34 mmol) dissloved in anhydrous dichloromethane (10 mL) was added to a dichloromethane solution (10 mL) of oxallyl chloride (1.0 mL) and pyridine (0.08 mL, 3 eq) at 0° C. After stirring the resulting solution for 5 min, concentrated ammonium hydroxide was added and the mixture was allowed to stir overnight. The mixture was diluted with dichloromethane and water, shaken and then the phases were separated. The organic phase was washed with brine, then with 1 M hydrochloric acid, 1 N aqueous sodium hydroxide and brine. The organic phase was separated, dried over anhydrous magnesium sulfate, filtered and concentrated in vacuo to afford a solid (0.17 g) which was purified by preparative plate chromatography (silica gel) using 5% methanol-dichloromethane and concentrated ammonium hydroxide to provide the compound of Formula 15.0 (0.086 g, 37%, mp 152.8° C.).

EXAMPLE 16

(16.0) →

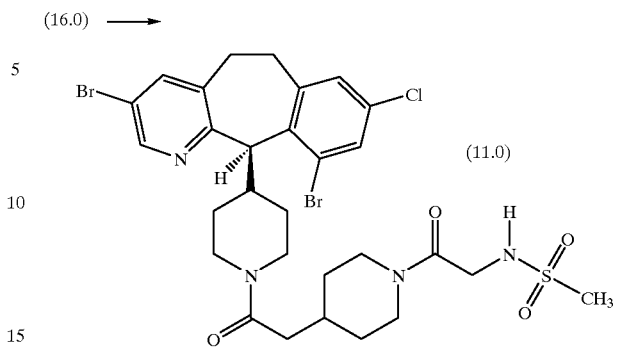

(11.0)

To the compound of Formula 16.0 (Example 2) (0.10 g) dissolved in anhydrous dichloromethane (10 mL) was added triethylamine (0.032 mL, 1.5 eq)) and methanesulfonyl chloride (0.014 mL, 1.2 eq) and the resulting solution was stirred at room temperature overnight. The solution was diluted with dichloromethane and washed with 1M hydrochloric acid and then with 1 M aqueous sodium hydroxide. The organic phase was separated and dried over anhydrous magnesium sulfate. Filtration and concentration in vacuo afforded the compound of Formula 11.0 (0.099 g, 89%, mp 116° C.).

EXAMPLE 17

(16.0) →

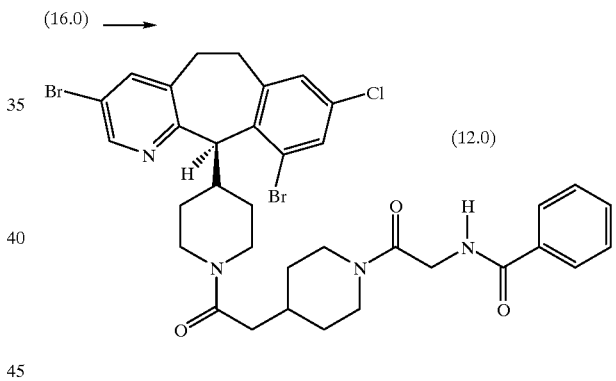

(12.0)

To the compound of Formula 16.0 (Example 2) (0.07 g) dissolved in anhydrous dichloromethane (10 mL) was added triethylamine (0.022 mL, 1.5 eq)) and benzoyl chloride (0.014 mL, 1.2 eq) and the resulting solution was stirred at room temperature overnight. The solution was diluted with dichloromethane and washed with 1M hydrochloric acid and then with 1 M aqueous sodium hydroxide. The organic phase was separated and dried over anhydrous magnesium sulfate. Filtration and concentration in vacuo afforded the compound of formula 12.0 (0.066 g, 85%, mp 117.2° C.).

EXAMPLE 18

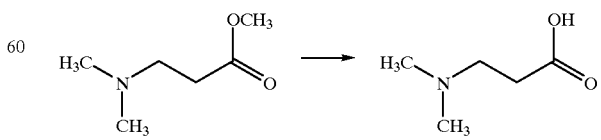

Dissolve 2 g (15 mmol) of methyl 3-(dimethyl amino) propionate in 20 mL of EtOH and then add 20 mL of 1M LiOH. Stir the reaction mixture at room temperature for 16 h. Strip off the solvents. Dissolve the resulting material in water and adjust pH to ~6. Concentrate the reaction mixture to give the product. Mass Spec.: MH$^+$=118.

EXAMPLE 19

(+)-4-(3,10-DIBROMO-8-CHLORO-6,11-DIHYDRO-5H-BENZO[5,6]CYCLOHEPTA[1,2-b]PYRIDIN-11-YL)-1-[4-(DIMETHYLAMINO)-1-OXOBUTYL]-4-PIPERIDINYL]ACETYL]PIPERIDINE (12.2)

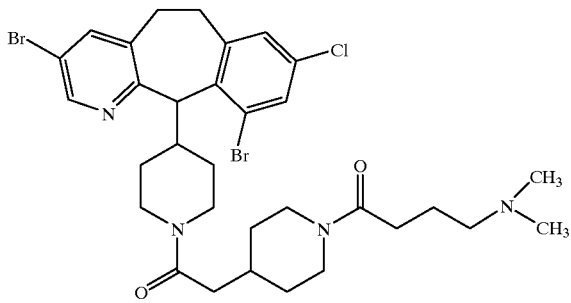

Dissolve 0.1 g (0.23 mmol) of the product of Preparative Example 8

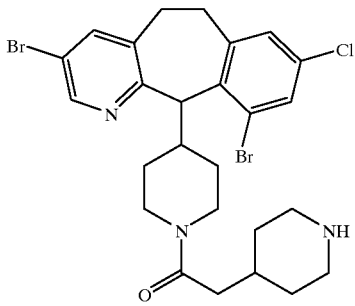

in 8 mL DMF, add 0.04 g (0.22 mmol) 4-(dimethylamino) butyric acid hydrochloride, 0.04 g (0.22 mmol) of DEC, 0.03 g (0.22 mmol) of HOBT and 0.1 mL of N-methyl morpholine at about 0 to about 4° C. Stir the reaction mixture overnight letting it warm to room temperature. Remove all the volatiles and then partition between H$_2$O—CH$_2$Cl$_2$. Extract the aqueous phase with CH$_2$Cl$_2$. Combine the CH$_2$Cl$_2$ fractions and dry over MgSO$_4$ and concentrate. Purify by flash chromatography, first eluting with 5% MeOH—(NH$_3$)—CH$_2$Cl$_2$ and then 10% MeOH—(NH$_3$)—CH$_2$Cl$_2$ to obtain the compound of Formula 12.2. Mass Spec. MH+=709, mp=69–71° C.

EXAMPLE 20

(+)-4-(3,10-DIBROMO-8-CHLORO-6,11-DIHYDRO-5H-BENZO[5,6]CYCLOHEPTA[1,2-b]PYRIDIN-11-YL)-1-[4-(DIMETHYLAMINO)-1-OXOPROPYL]-4-PIPERIDINYL]ACETYL]PIPERIDINE (12.3)

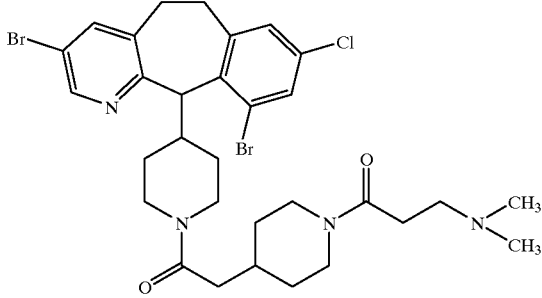

By following essentially the same procedure as described in Example 19 above, but using 3-(dimethylamino) propionic acid (Example 18) instead of 4-(dimethylamino) butyric acid hydrochloride, the compound of Formula 12.3 was prepared. FAB-MS–MH+=695, mp=82–84° C.

EXAMPLE 21

(+)-4-(3,10-DIBROMO-8-CHLORO-6,11-DIHYDRO-5H-BENZO[5,6]CYCLOHEPTA[1,2-b]PYRIDIN-11-YL)-1-[4-(DIMETHYLAMINO)-1-OXOETHYL]-4-PIPERIDINYL]ACETYL]PIPERIDINE (12.1)

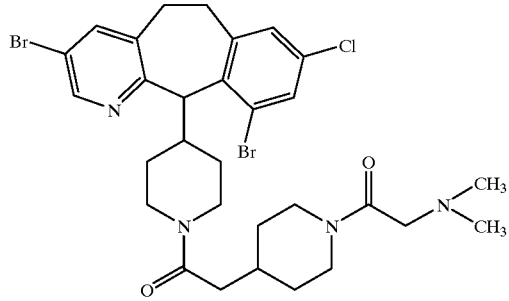

By following essentially the same procedure as described in Example 19 above, but using N,N-dimethyl glycine instead of 4-(dimethylamino) butyric acid hydrochloride, the compound of Formula 12.1 was prepared. FAB-MS—MH+=681, mp=123–124° C.

EXAMPLE 22

(+)-4-(3,10-DIBROMO-8-CHLORO-6,11-DIHYDRO-5H-BENZO[5,6]CYCLOHEPTA[1,2-b]PYRIDIN-11-YL)-1-[4-(PIPERIDINYL)-1-OXOETHYL]-4-PIPERIDINYL]ACETYL]PIPERIDINE (14.2)

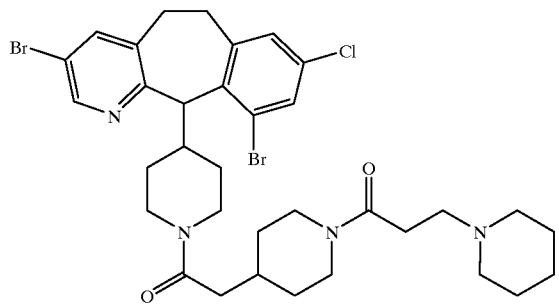

By following essentially the same procedure as described in Example 19 above, but using 1-piperidine propionic acid instead of 4-(dimethylamino) butyric acid hydrochloride, the compound of Formula 14.2 was prepared. FAB-MS: MH$^+$735, mp=127–128° C.

EXAMPLE 23

(+)-4-(3,10-DIBROMO-8-CHLORO-6,11-DIHYDRO-5H-BENZO[5,6]CYCLOHEPTA[1,2-b]PYRIDIN-11-YL)-1-[4-(TETRAHYDRO-2H-1,4-THIAZIN-4-YL)-1-OXOETHYL 1-1-DIOXIDE]-4-PIPERIDINYL]ACETYL]PIPERIDINE (14.1)

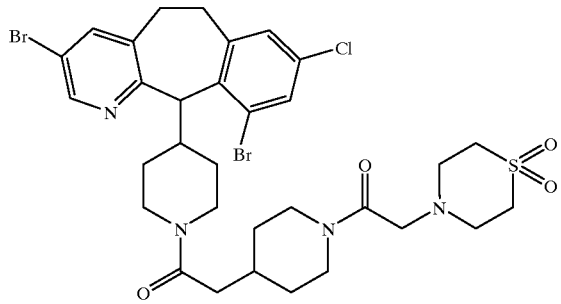

By following essentially the same procedure as described in Example 19 above, but using thiomorpholine S-dioxide acetic acid instead of 4-(dimethylamino) butyric acid hydrochloride, the compound of Formula 14.1 was prepared. mp=140–141° C.

EXAMPLE 24

(+)-METHYL-4-[2-[4-[(3,10-DIBROMO-8-CHLORO-6,11-DIHYDRO-5H-BENZO[5,6]CYCLOHEPTA[1,2-b]PYRIDIN-11-YL)-1-PIPERIDINYL]-2-OXOETHYL]-DELTA-OXO-1-PIPERIDINE-PENTANOATE (15.1)

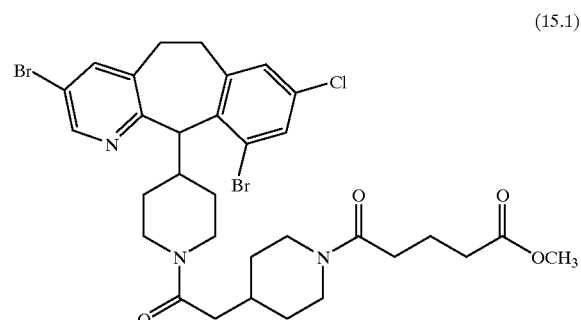

By following essentially the same procedure as described in Example 19 above, but using monomethyl glutarate instead of 4-(dimethylamino) butyric acid hydrochloride, the compound of Formula 15.1 was prepared. FAB-MS—MH+=724, mp=101–102° C.

EXAMPLE 25

(+)-METHYL-4-[2-[4-[(3,10-DIBROMO-8-CHLORO-6,11-DIHYDRO-5H-BENZO[5,6]CYCLOHEPTA[1,2-b]PYRIDIN-11-YL)-1-PIPERIDINYL]-2-OXOETHYL]-GAMMA-OXO-1-PIPERIDINEBUTANOATE (15.2)

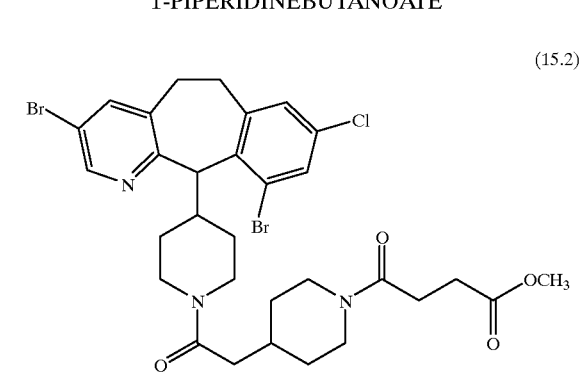

By following essentially the same procedure as described in Example 19 above, but using monomethyl succinate instead of 4-(dimethylamino) butyric acid hydrochloride, the compound of Formula 15.2 was prepared. FAB-MS—MH+=710, mp=114–115° C.

EXAMPLE 26

(+)-ETHYL-4-[2-[4-[(3,10-DIBROMO-8-CHLORO-6,11-DIHYDRO-5H-BENZO[5,6]CYCLOHEPTA[1,2-b]PYRIDIN-11-YL)-1-PIPERIDINYL]-2-OXOETHYL]-BETA-OXO-1-PIPERIDINE-BUTANOATE (15.3)

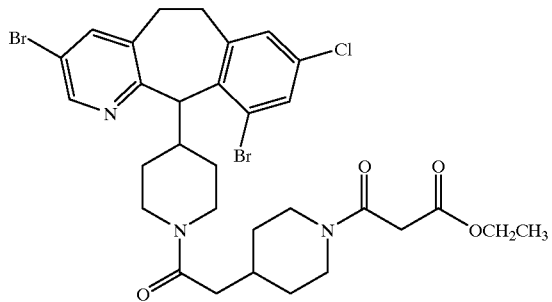

By following essentially the same procedure as Example 19 above, but using monoethyl malonate instead of 4-(dimethylamino) butyric acid hydrochloride, the compound of Formula 15.3 was obtained. FAB-MS—MH$^+$=710, m.p.=77–78° C.

EXAMPLE 27

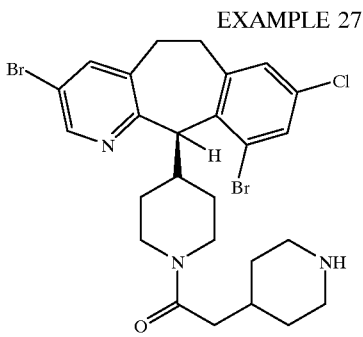

Dissolve the (+) product of Preparative Example 8, Step D (0.01 g, 0.017 mmol) in 0.5 mL of DMF, stir at room temperature and add 0.003 g (0.017 mmol) of DEC, 0.002 g (0.017 mmol) of HOBT and 0.003 g (0.017 mmole) of the product of Preparative Example 12. Stir the mixture at room temperature for 18 hr, then concentrate in vacuo to a residue and partition between ethyl acetate and water. Wash the organic phase with aqueous sodium bicarbonate solution then brine. Dry the organic phase over magnesium sulfate, filter and concentrate in vacuo to a residue. Chromatograph the residue on silica gel, eluting with dichlorornethane (saturated with ammonia)—methanol (95%–5%) to yield the product (0.01 g) as a white solid. M.p.=84°–°90° C., Mass Spec.: MH+=709.

EXAMPLES 28–60

Follow the procedure of Example 27 but use the acid shown in Table 1 below instead of the product of Preparative Example 12 to obtain the compounds of Formula 1.7

(1.7)

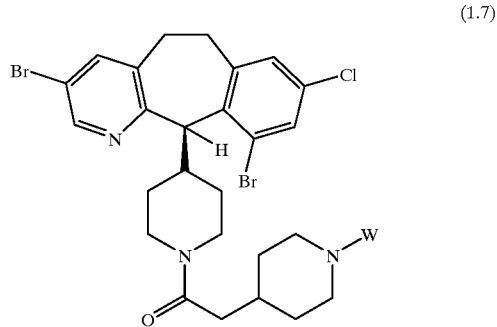

wherein W is defined in Table 1. The Formula number of the compound formed is given in parenthesis below the W substituent.

TABLE 1
| EX. | Acid | W | mp (° C.) |
|---|---|---|---|
| 28 | 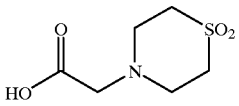 | 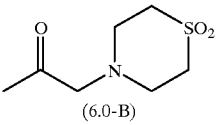 (6.0-B) | 140–140.8 |
| 29 | 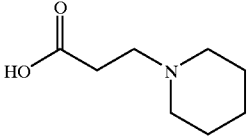 | 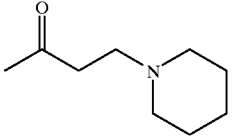 (7.0-B) | 127.2–127.7 |
| 30 | 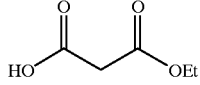 | 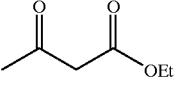 (8.0-B) | 77.2–78.1 |
| 31 | 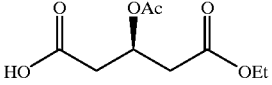 | 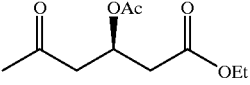 (16.0-B) | 103.5–106.4 |
| 32 | 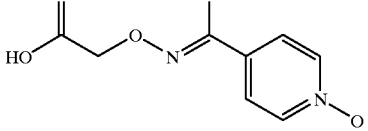 Preparative Ex. 4 | 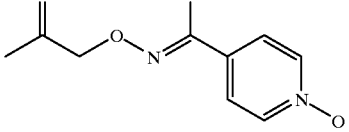 (22.0-B) | 129 (d) |
| 33 | 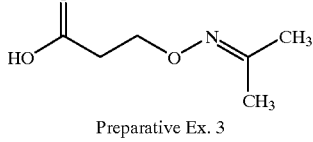 Preparative Ex. 3 | 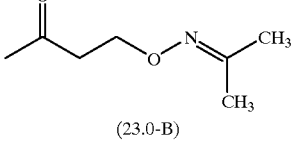 (23.0-B) | 75 |
| 34 | 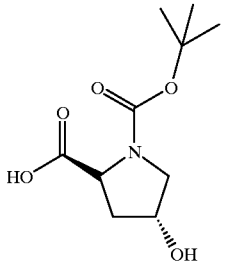 | 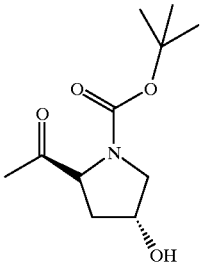 (24.0-B) | 145.8–147.7 |
| 35 | 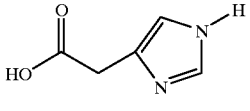 | 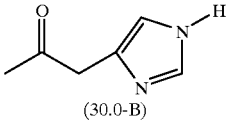 (30.0-B) | 125.8–127.3 |

TABLE 1-continued

| EX. | Acid | W | mp (° C.) |
|---|---|---|---|
| 36 | HOOC-C(=O)-N(CH₃)₂ | CH₃-C(=O)-C(=O)-N(CH₃)₂ (33.0-B) | 95–143 |
| 37 | HOOC-CH₂-OH | CH₃-C(=O)-CH₂-OH (37.0-B) | — |
| 38 | HOOC-CH₂-CN | CH₃-C(=O)-CH₂-CN (44.0-B) | 124–125 |
| 39 | HOOC-C(=O)-NH-OCH₃ | CH₃-C(=O)-C(=O)-NH-OCH₃ (49.0-B) | 204.5 |
| 40 | HOOC-CH₂-C(=O)-NH₂ | CH₃-C(=O)-CH₂-C(=O)-NH₂ (50.0-B) | 137.4–138 |
| 41 | HOOC-CH₂-C(=O)-NH-CH(iPr)-OCH₃ | CH₃-C(=O)-CH₂-C(=O)-NH-CH(iPr)-OCH₃ (51.0-B) | 115.8–116.4 |
| 42 | 3,5-dimethylisoxazole-4-carboxylic acid | 4-acetyl-3,5-dimethylisoxazole (65.0-B) | — |
| 43 | HOOC-(CH₂)₅-C(=O)-OCH₃ | CH₃-C(=O)-(CH₂)₅-C(=O)-OCH₃ (68.0-B) | — |
| 44 | HOOC-C(=O)-CH₃ | CH₃-C(=O)-C(=O)-CH₃ (72.0-B) | 113–120 |

TABLE 1-continued
| EX. | Acid | W | mp (° C.) |
|---|---|---|---|
| 45 | 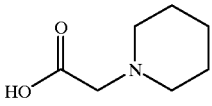 | 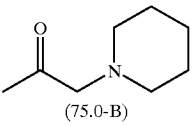 (75.0-B) | 95–100 |
| 46 | 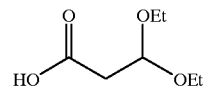 | 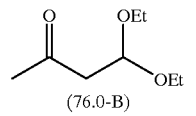 (76.0-B) | 100–108 |
| 47 | 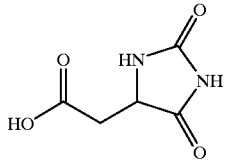 | 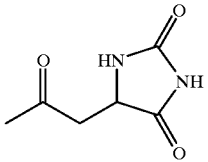 (77.0-B) | 192–203 |
| 48 | 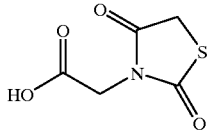 | 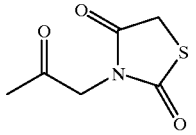 (79.0-B) | 172–190 |
| 49 | 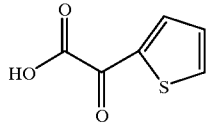 | 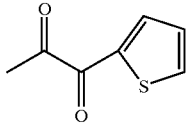 (81.0-B) | 154–163 |
| 50 | 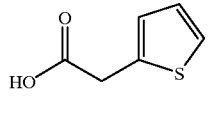 | 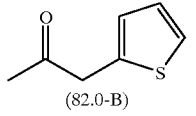 (82.0-B) | 129–139 |
| 51 | 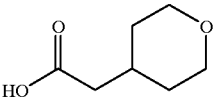 J. Med. Chem. (1993), 36, 2300 | 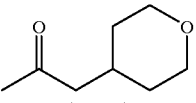 (85.0-B) | 114.5–119.3 |
| 52 | 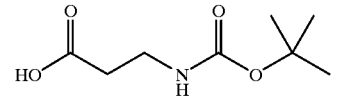 | 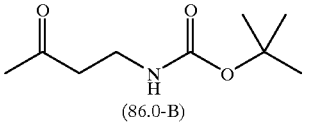 (86.0-B) | 87–88 |
| 53 | 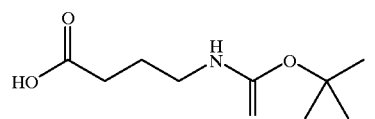 | 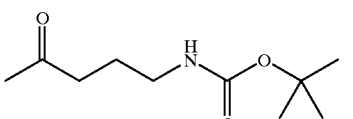 (89.0-B) | 102.7–103.3 |

TABLE 1-continued
| EX. | Acid | W | mp (° C.) |
|---|---|---|---|
| 54 | 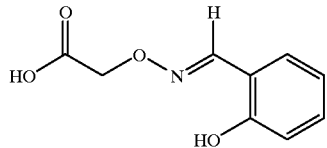<br>Preparative Ex. 5 | 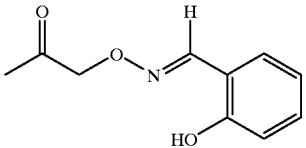<br>(95.0-B) | 145 (d) |
| 55 | 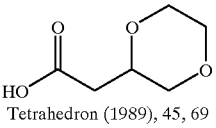<br>Tetrahedron (1989), 45, 69 | 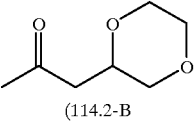<br>(114.2-B | 129–143 |
| 56 | 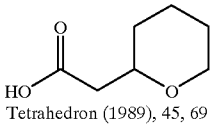<br>Tetrahedron (1989), 45, 69 | 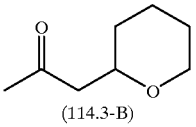<br>(114.3-B) | 124–132 |
| 57 | 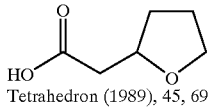<br>Tetrahedron (1989), 45, 69 | 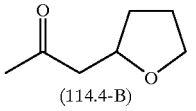<br>(114.4-B) | 127–136 |
| 58 | 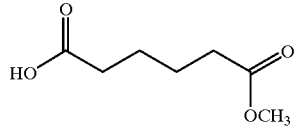 | 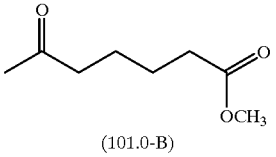<br>(101.0-B) | 74–75 |
| 59 | 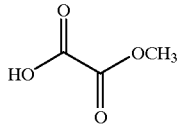 | 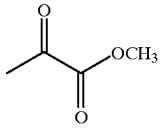<br>(104.0-B) | — |
| 60 | 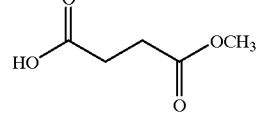 | 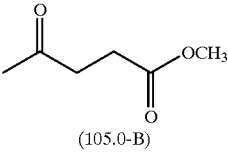<br>(105.0-B) | 114–115 |
| 61 | 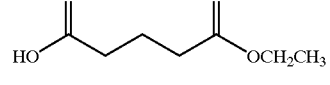 | 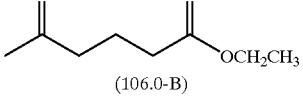<br>(106.0-B) | 101.1–101.5 |

EXAMPLE 62

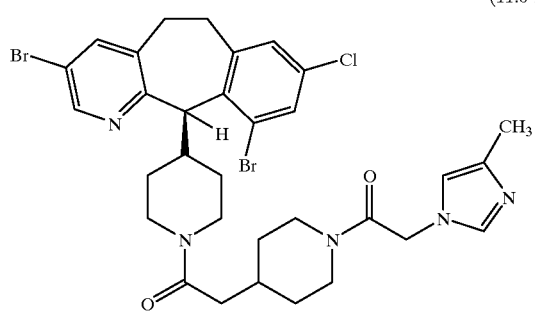

Step A

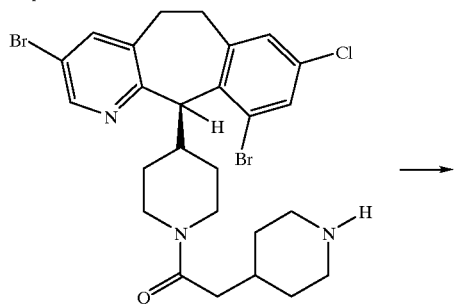

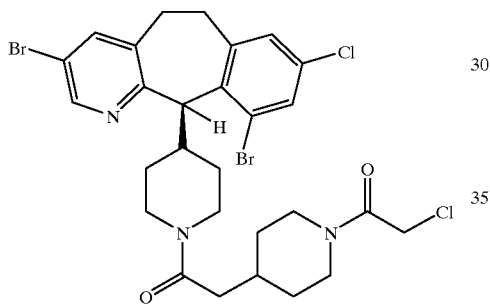

Dissolve the (+) product of Preparative Example 8, Step D (0.744 g, 1.25 mmol) in 20 mL of dichloromethane containing 0.348 mL (2.5 mmol) of triethylamine, stir at room temperature and add 0.1 mL (1.26 mmol) of chloroacetylchloride. Stir for 10 hr then add 20 mL of 1N HCl. Wash the organic layer with aqueous sodium bicarbonate, dry over magnesium sulfate, and concentrate under vacuum to give 0.71 g of the product.

Step B

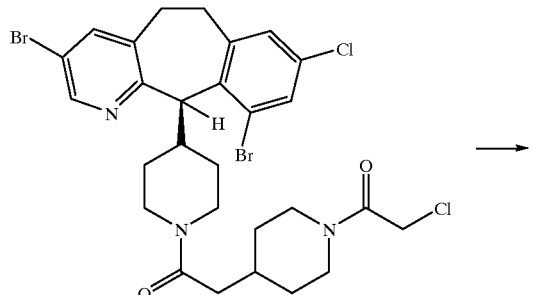

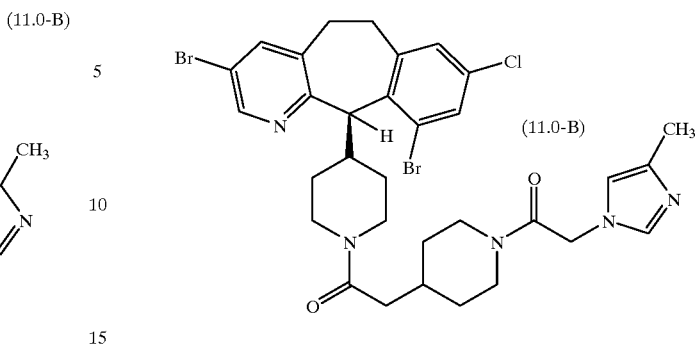

Dissolve 0.120 g (0.78 mmol) of the product from Step A, 0.0365 g (0.535 mmol) of 4-methylimidazole and 0.057 g (0.535 mmol) of sodium carbonate in 10 mL of DMF and stir at 120–130° C. for 18 hr. Cool to 25° C. and 30 mL of water and filter the precipitated solid. Dissolve the solid in 50 mL of dichloromethane and wash with 1N NaOH. Dry the organic layer over magnesium sulfate and concentrate under vacuum. Chromatograph the residue on a silica gel TLC plate using methanol-dichloromethane saturated with ammonia (5–95) to give 0.06 g of the product as a white solid mp=148.9° C.

EXAMPLES 63–75

Follow the procedure of Example 62, but use the amine shown in Table 2 below instead of 4-methylimidazole, to obtain the compounds of Formula 1.7

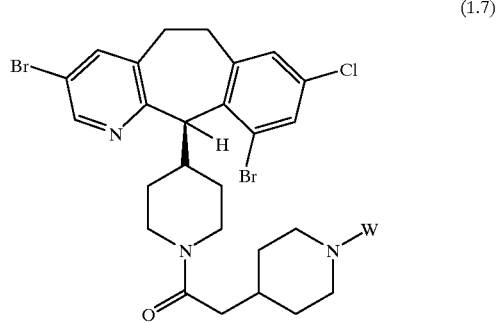

(1.7)

wherein W is defined in Table 2. The Formula number of the compound formed is given in parenthesis below the W substituent.

TABLE 2

| EX. | Amine | W | mp (°C.) |
|---|---|---|---|
| 63 | 2-methyl-1H-imidazole | (10.0-B) 1-(2-methyl-1H-imidazol-1-yl)propan-2-one | 137.8 |
| 64 | 1H-benzimidazole | (12.0-B) 1-(1H-benzimidazol-1-yl)propan-2-one | 151.3 |
| 65 | imidazo[4,5-b]pyridine | (13.0-B) | 154.2 |
| 66 | 4-phenyl-1H-imidazole | (20.0-B) | 150.3 (d) |
| 67 | 4-nitro-1H-imidazole | (26.0-B) | 168.1 |
| 68 | 1H-pyrrole | (34.0-B) | 123.4 |
| 69 | methyl 1H-pyrrole-2-carboxylate | (35.0-B) | 184–190 |
| 70 | benzyl 1H-pyrrole-2-carboxylate | (52.0-B) CO₂H | 178.6 |

TABLE 2-continued

| EX. | Amine | W | mp (° C.) |
|---|---|---|---|
| 71 | (imidazole with CH3 and CO2Et) | (53.0-B) | 156.1 |
| 72 | (imidazole with CO2Et and CH3) | (54.0-B) | 158.7 |
| 73 | (pyrrole with CO2CH2Ph) | (55.0-B) | 130.4 |
| 74 | (imidazole-CH2-CO-OCH3) | (56.0-B) | 122.8 |
| 75 | (Na-triazole) | (57.0-B) | 125.3 |

EXAMPLE 76

(17.0-B)

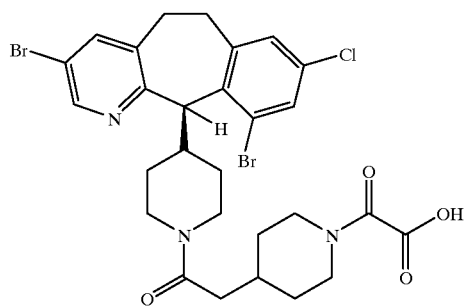

Dissolve 1 equivalent of the product of Example 59 (Compound 104.0-B, Table 1) in methanol containing 1.2 equivalents of 1N KOH in methanol and stir for 48 hr at 25° C. Acidify to pH 2 with 1N HCl and extract with dichloromethane. Dry the organic layer over magnesium sulfate and concentrate under vacuum. Purify the residue by preparative silica gel TLC using methanol-dichloromethane-acetic acid (5-94-1) to give the product as a white solid mp=240.1° C.

EXAMPLE 77

(14.0-B)

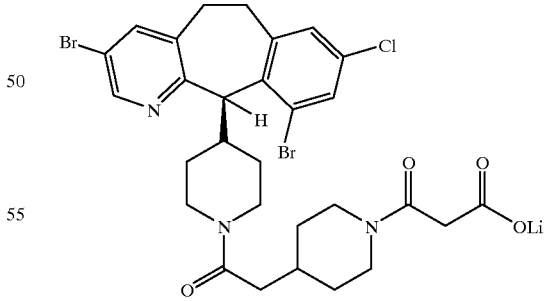

Dissolve 1 equivalent of the product of Example 30 (Compound 8.0-B, Table 1) in 95% aqueous ethanol containing 1.1 equivalents of LiOH and stir for 16 hr at 25° C. Concentrate under vacuum to give the product as a white solid.

EXAMPLE 78

(18.0-B)

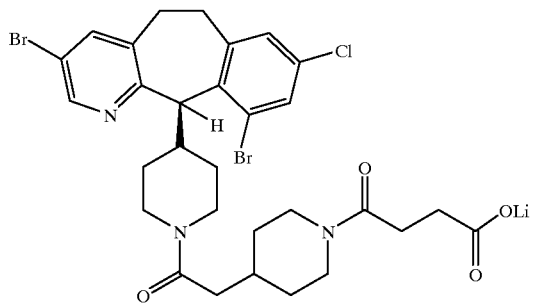

Follow the procedure of Example 77 but use the product of Example 60 (Compound 105.0-B, Table 1) instead of the product of Example 59 (Compound 104.0-B, Table 1) to obtain the product as a white solid.

EXAMPLE 79

(19.0-B)

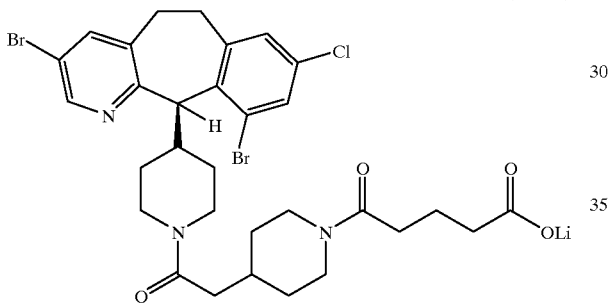

Follow the procedure of Example 77 but use the product of Example 61 (Compound 106.0-B, Table 1) instead of the product of Example 59 (Compound 104.0-B, Table 1) to obtain the product as a white solid.

EXAMPLE 80

(70.0-B)

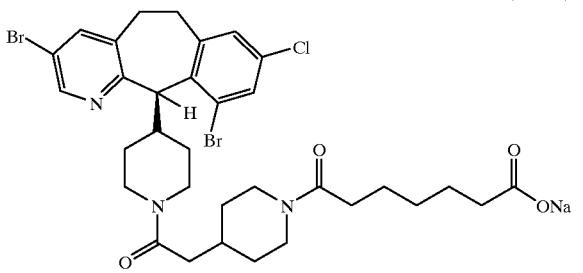

Dissolve 1 equivalent of the product of Example 43 (Compound 68.0-B, Table 1) in 95% aqueous methanol containing 1.1 equivalents of NaOH and stir for 16 hr at 25° C. Concentrate under vacuum to give the product as a white solid. mp=215.5–216.2° C.

EXAMPLE 81

(107.0-B)

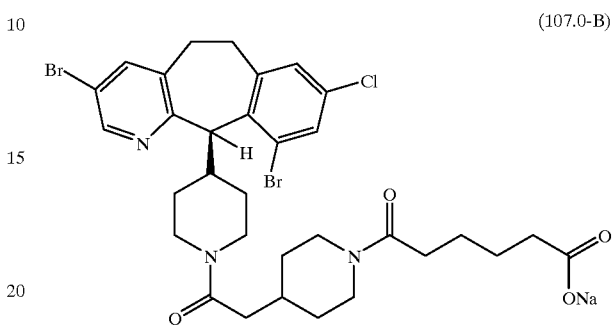

Dissolve 1 equivalent of the product of Example 58 (Compound 101.0-B, Table 1) in 95% aqueous methanol containing 1.1 equivalents of NaOH and stir for 16 hr at 25° C. Concentrate under vacuum to give the product as a white solid. mp=240° C. (d).

EXAMPLE 82

(67.0-B)

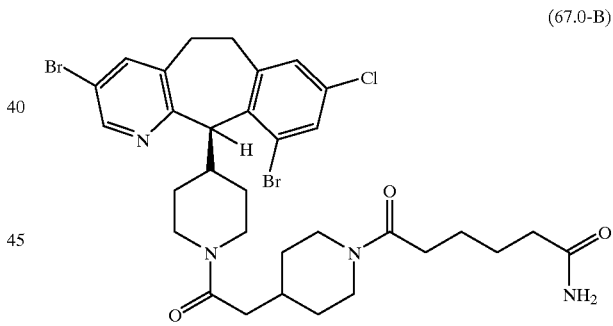

Dissolve 1.0 equivalent of the product of Example 81 (Compound 107.0-B) in DMF containing 5.0 equivalents of ammonium chloride and 1.0 equivalent each of DEC, HOBT and N-methylmorpholine. Stir the mixture at room temperature for 18 hr, then concentrate in vacuo to a residue and partition between ethyl acetate and water. Wash the organic phase with aqueous sodium bicarbonate solution then brine. Dry the organic phase over magnesium sulfate, filter and concentrate in vacuo to a residue. Chromatograph the residue on silica gel to obtain the product as a white solid mp=125.5–126.5° C.

EXAMPLE 83

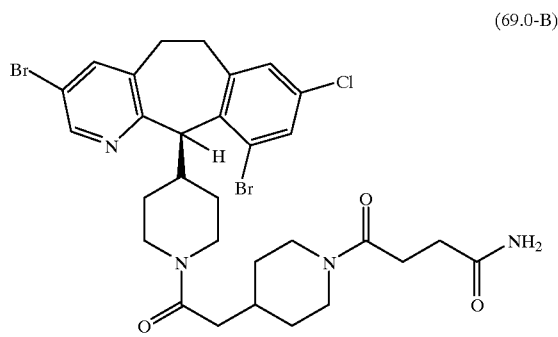

(69.0-B)

Dissolve 1.0 equivalent of the product of Example 78 (Compound 18.0-B) in DMF containing 5.0 equivalents of ammonium chloride and 1.0 equivalent each of DEC, HOBT and N-methylmorpholine. Stir the mixture at room temperature for 18 hr, then concentrate in vacuo to a residue and partition between ethyl acetate and water. Wash the organic phase with aqueous sodium bicarbonate solution then brine. Dry the organic phase over magnesium sulfate, filter and concentrate in vacuo to a residue. Chromatograph the residue on silica gel to obtain the product as a white solid mp=142.8–143.3° C.

EXAMPLE 84

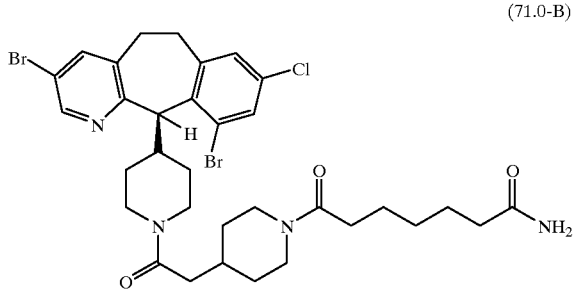

(71.0-B)

Dissolve 1.0 equivalent of the product of Example 80 (Compound 70.0-B) in DMF containing 5.0 equivalents of ammonium chloride and 1.0 equivalent each of DEC, HOBT and N-methylmorpholine. Stir the mixture at room temperature for 18 hr, then concentrate in vacuo to a residue and partition between ethyl acetate and water. Wash the organic phase with aqueous sodium bicarbonate solution then brine. Dry the organic phase over magnesium sulfate, filter and concentrate in vacuo to a residue. Chromatograph the residue on silica gel to obtain the product as a white solid mp=119.2–120° C.

EXAMPLE 85

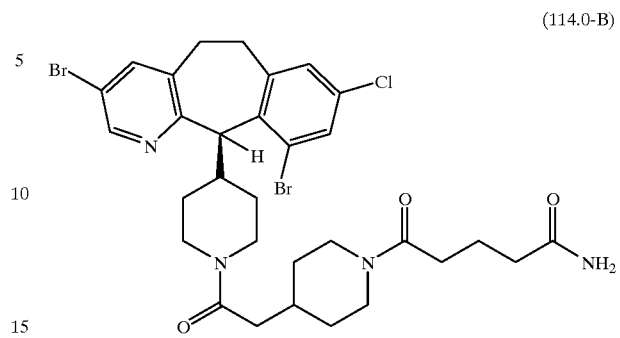

(114.0-B)

Dissolve 1.0 equivalent of the product of Example 81 (Compound 107.0-B) in DMF containing 5.0 equivalents of ammonium chloride and 1.0 equivalent each of DEC, HOBT and N-methylmorpholine. Stir the mixture at room temperature for 18 hr, then concentrate in vacuo to a residue and partition between ethyl acetate and water. Wash the organic phase with aqueous sodium bicarbonate solution then brine. Dry the organic phase over magnesium sulfate, filter and concentrate in vacuo to a residue. Chromatograph the residue on silica gel to obtain the product as a white solid.

EXAMPLE 86

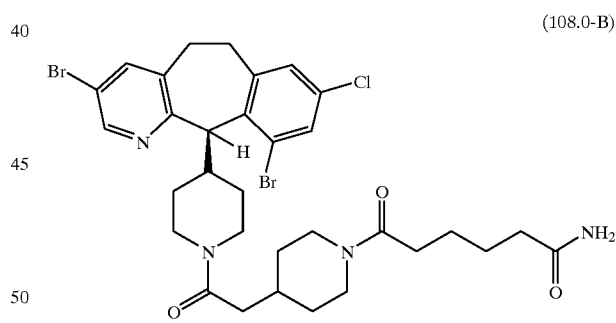

(108.0-B)

Dissolve 1.0 equivalent of the product of Example 79 (Compound 19.0-B) in DMF containing 5.0 equivalents of ammonium chloride and 1.0 equivalent each of DEC, HOBT and N-methylmorpholine. Stir the mixture at room temperature for 18 hr, then concentrate in vacuo to a residue and partition between ethyl acetate and water. Wash the organic phase with aqueous sodium bicarbonate solution then brine. Dry the organic phase over magnesium sulfate, filter and concentrate in vacuo to a residue. Chromatograph the residue on silica gel to obtain the product as a white solid.

EXAMPLE 87

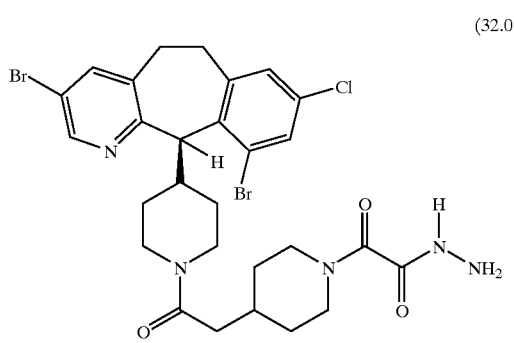
(32.0-B)

Dissolve 1.0 equivalent of the product of Example 59 (Compound 104.0-B, Table 1) in dichloromethane containing 4.0 equivalents of anhydrous hydrazine and stir for 48 hr. Concentrate under vacuum and chromatograph the residue on preparative silica gel TLC using methanol-dichloromethane 5–95) to yield the product as a yellow solid, mp=90° C.

EXAMPLE 88

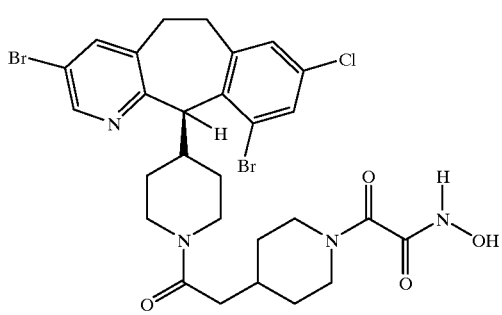
(58.0-B)

Dissolve 1.0 equivalent of the product of Example 59 (Compound 104.0-B, Table 1) in methanol containing 1.4 equivalents of LiOH and stir for 18 hr. Add DMF containing 1.0 equivalent each of DEC, HOBT and N-methylmorpholine and O-tert-butyldimethylsilyl hydroxylamine. Stir the mixture at room temperature for 48 hr, then concentrate in vacuo to a residue and partition between ethyl acetate and water. Dry the organic phase over magnesium sulfate, filter and chromatograph on silica gel using methanol-dichloromethane (5–95) to obtain the product as a white solid, mp=103.0° C.

EXAMPLE 89

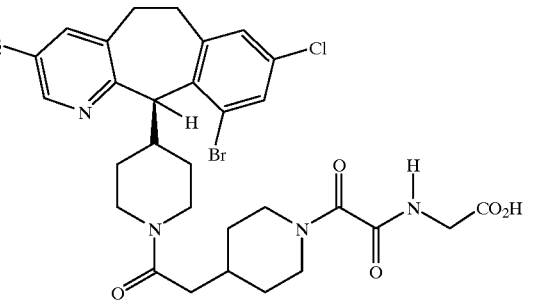
(59.0-B)

Dissolve 1.0 equivalent the product of Example 59 (Compound 104.0-B, Table 1) in methanol containing 3.0 equivalents of KOH and 3.0 equivalent of glycine hydrochloride tert-butyl ester and stir for 7 days. Concentrate under vacuum and chromatograph the residue on silica gel using methanol-dichloromethane (5–95 to obtain the product as a yellow solid, mp=108° C.

EXAMPLE 90

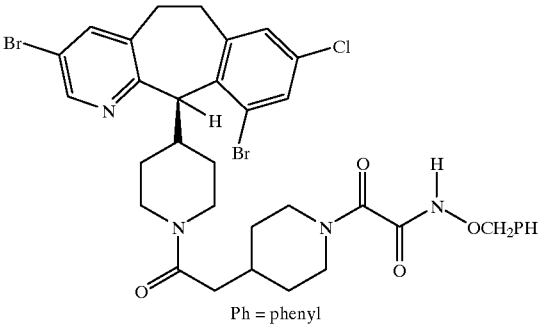
(60.0-B)

Ph = phenyl

Dissolve 1.0 equivalent the product of Example 59 (Compound 104.0-B, Table 1) in methanol containing 3.0 equivalents of KOH and 3.0 equivalent of O-benzylhydroxyl-amine hydrochloride and stir for 48 hr. Concentrate under vacuum and chromatograph the residue on silica gel using methanol-dichloromethane-acetic acid (10-89.5-0.5) to obtain the product as a yellow solid mp=75° C.

EXAMPLE 91

(64.0-B)

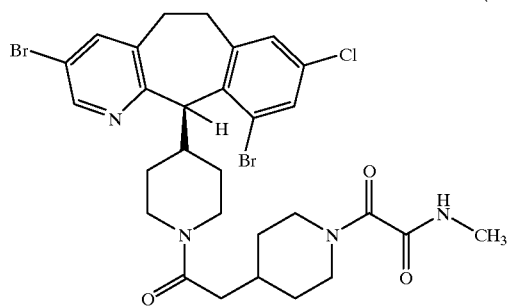

Dissolve 1.0 equivalent the product of Example 59 (Compound 104.0-B, Table 1) in methanol 4.0 equivalent of methylamine and stir for 18 hr. Concentrate under vacuum and chromatograph the residue on silica gel using methanol-dichloromethane saturated with ammonia (5–95) to obtain the product as a yellow solid mp=86–132° C.

EXAMPLE 92

(88.0-A)

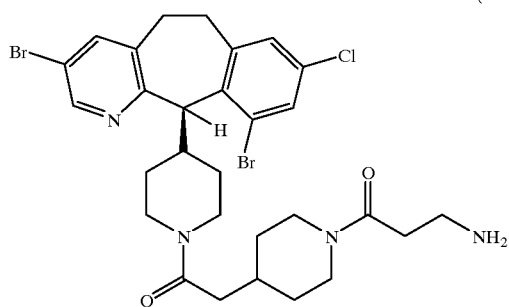

Dissolve 1.0 equivalent of the product from Example 52 (Compound 86.0-B, Table 1) in dichloromethane containing 2 equivalents of trifluoroacetic acid and stir for 2 hr. Concentrate under vacuum and partition the residue between dichloromethane and aqueous sodium bicarbonate. Dry the organic layer over magnesium sulfate and concentrate under vacuum to yield the product as a white solid, mp=120.6–120.8° C.

EXAMPLE 93

(90.0-B)

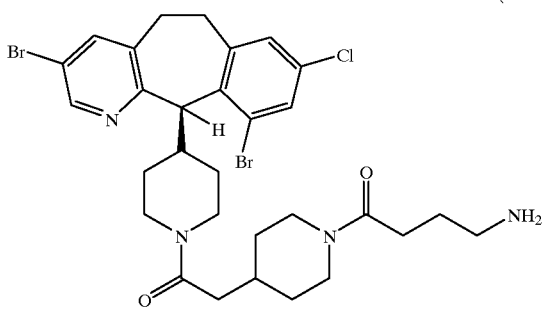

Dissolve 1.0 equivalent of the product from Example 53 (Compound 89.0-B, Table 1) in dichloromethane containing 2 equivalents of trifluoroacetic acid and stir for 2 hr. Concentrate under vacuum and partition the residue between dichloromethane and aqueous sodium bicarbonate. Dry the organic layer over magnesium sulfate and concentrate under vacuum to yield the product as a white solid, mp=114–115° C.

EXAMPLE 94

(38.0-B)

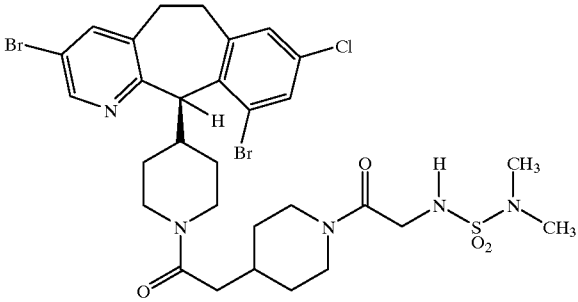

Dissolve 1.0 equivalent of the product from Example 1 in dichloromethane containing 2 equivalents of trifluoroacetic acid and stir for 2 hr. Concentrate under vacuum and partition the residue between dichloro-methane and aqueous sodium bicarbonate. Dry the organic layer over magnesium sulfate and concentrate under vacuum. Dissolve the residue in dichloromethane containing 1.5 equivalents of triethyl amine and 1.2 equivalents of dimethylsulfamoyl chloride. Stir for 18 hr then wash with 1N HCl followed by 1N NaOH. Dry the organic layer over magnesium sulfate and concentrate under vacuum to obtain the produce, mp=124.4–130° C.

EXAMPLE 95

(39.0-B)

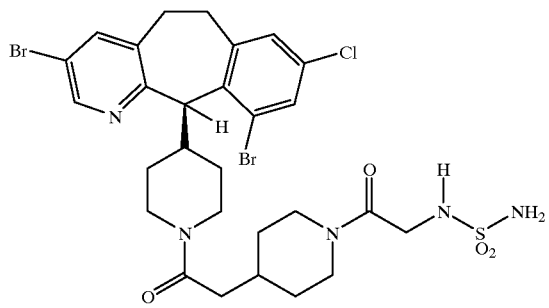

Dissolve 1.0 equivalent of the product from Example 1 in dichloromethane containing 2 equivalents of trifluoroacetic acid and stir for 2 hr. Concentrate under vacuum and partition the residue between dichloro-methane and aqueous sodium bicarbonate. Dry the organic layer over magnesium sulfate and concentrate under vacuum. Dissolve the residue in 10.0 equivalents of aqueous sulfamide and reflux for 48 hr. Concentrate under vacuum and chromatograph the residue on silica gel using methanol-dichloromethane saturated with ammonia (5–95) to obtain the product, mp=151.9° C.

EXAMPLE 96

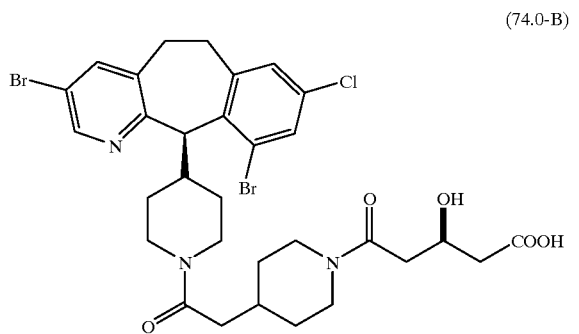

(74.0-B)

The product of Example 31 (Compound 16.0-B, Table 1) (372.1 mg, 0.468 mmol) was dissolved in 3 mL of 6 M HCl and the solution stirred at room temperature overnight. The reaction mixture was added to 25 mL water, and the resulting precipitate was filtered and washed with 0.1 M HCl. The filtrate was saturated with NaCl and extracted continuously for 48 h to provide additional crude product. Purify the combined crude material by flash chromatoghrapy (C-18 reverse phase silica, gradient of 50% MeOH/0.17 M HOAc to 90% MeOH/0.17 M HOAc). The resulting material was dissolved in MeOH and added to water and the resulting suspension evaporated to dryness to give the title compound as a white solid (mp 133.5°–141.2° C., heating 2°–3° C./min).

EXAMPLE 97

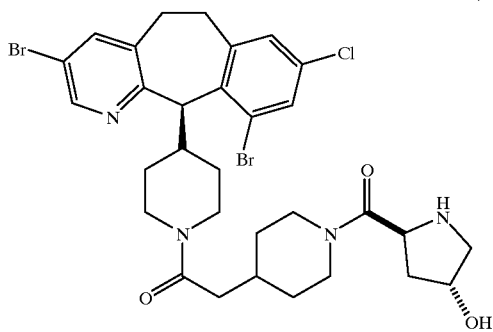

(63.0-B)

The product of Example 34 (Compound 24.0-B, Table 1) (450.0 mg, 0.56 mmol) was dissolved in 20 mL $CH_2Cl_2$, cooled to 0° C., and 8 mL of trifluoroacetic acid was added slowly. After 1 h the cold mixture was diluted with 50% NaOH (aq) and water. The mixture was extracted with $CH_2Cl_2$, which was then dried ($MgSO_4$) and evaporated to give the title compound as a yellow solid (230 mg, mp 161.0°–163.0° C.).

EXAMPLE 98

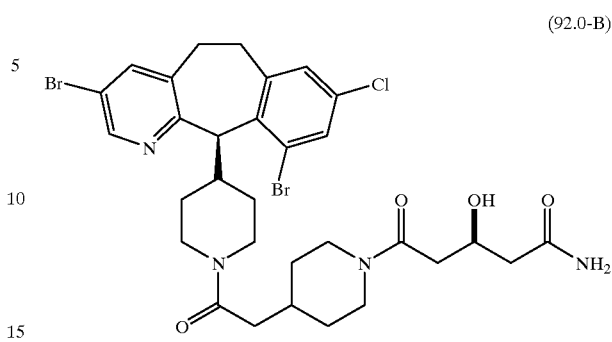

(92.0-B)

The product of Example 96 (Compound 74.0-B) (93.6 mg, 0.129 mmol) and 1-hydroxybenzotriazole (27.3 mg, 0.202 mmol) were dissolved in 1 mL of DMF. $NH_4Cl$ (14.8 mg, 0.276 mmol), N-methylmorpholine (70 µL) and DEC•HCl (30.8 mg, 0.161 mmol) were added. After 4 h the mixture was evaporated and the residue purified by flash chromatoghrapy (C-18 reverse phase silica, gradient of 50% MeOH/0.17 M HOAc to 90% MeOH/0.17 M HOAc). The resulting material was lyophilized from $HOAc/H_2O$ to give the title compound as a tan solid (67.7 mg, mp 115.2°–122.0° C., heating 2°–3° C./min).

EXAMPLE 99

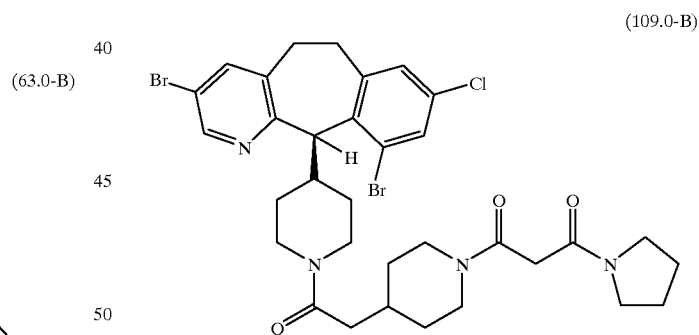

(109.0-B)

Dissolve 1.0 equivalent of the product of Example 77 (Compound 14.0-B) in DMF containing 1.0 equivalent each of DEC, HOBT, N-methylmorpholine and pyrrolidine. Stir the mixture at room temperature for 18 hr, then concentrate in vacuo to a residue and partition between ethyl acetate and water. Wash the organic phase with aqueous sodium bicarbonate solution then brine. Dry the organic phase over magnesium sulfate, filter and concentrate in vacuo to a residue. Chromatograph the residue on silica gel to obtain the product as a white solid.

EXAMPLE 100

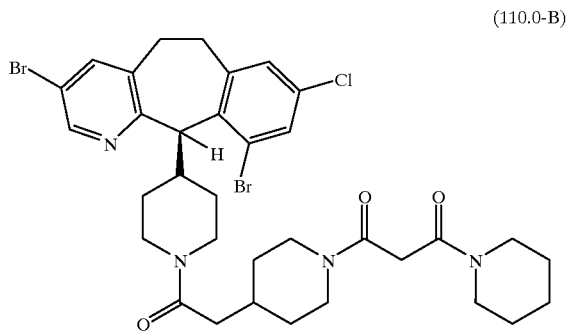

(110.0-B)

Dissolve 1.0 equivalent of the product of Example 77 (Compound 14.0-B) in DMF containing 1.0 equivalent each of DEC, HOBT, N-methylmorpholine and piperidine. Stir the mixture at room temperature for 18 hr, then concentrate in vacuo to a residue and partition between ethyl acetate and water. Wash the organic phase with aqueous sodium bicarbonate solution then brine. Dry the organic phase over magnesium sulfate, filter and concentrate in vacuo to a residue. Chromatograph the residue on silica gel to obtain the product as a white solid mp=135–136° C.

EXAMPLE 101

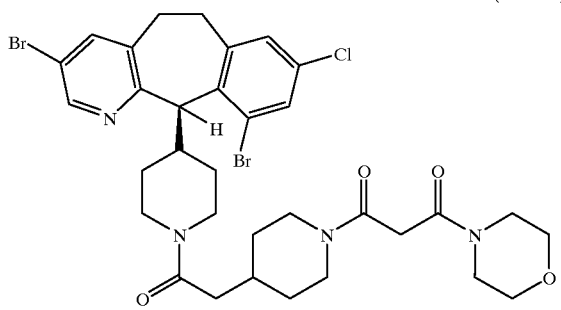

(111.0-B)

Dissolve 1.0 equivalent of the product of Example 77 (Compound 14.0-B) in DMF containing 1.0 equivalent each of DEC, HOBT, N-methylmorpholine and morpholine. Stir the mixture at room temperature for 18 hr, then concentrate in vacuo to a residue and partition between ethyl acetate and water. Wash the organic phase with aqueous sodium bicarbonate solution then brine. Dry the organic phase over magnesium sulfate, filter and concentrate in vacuo to a residue. Chromatograph the residue on silica gel to obtain the product as a white solid mp=135–136° C.

EXAMPLE 102

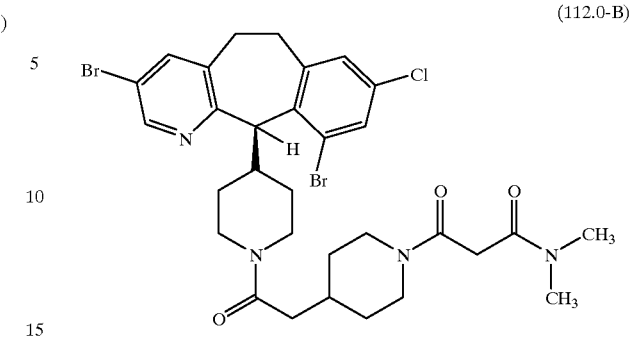

(112.0-B)

Dissolve 1.0 equivalent of the product of Example 77 (Compound 14.0-B) in DMF containing 1.0 equivalent each of DEC, HOBT, N-methylmorpholine and dimethylamine. Stir the mixture at room temperature for 18 hr, then concentrate in vacuo to a residue and partition between ethyl acetate and water. Wash the organic phase with aqueous sodium bicarbonate solution then brine. Dry the organic phase over magnesium sulfate, filter and concentrate in vacuo to a residue. Chromatograph the residue on silica gel to obtain the product as a white solid mp=133–134° C.

ASSAYS

FPT $IC_{50}$ (inhibition of farnesyl protein transferase, in vitro enzyme assay) and COS Cell $IC_{50}$ (Cell-Based Assay) were determined following the assay procedures described in WO 95/10516, published Apr. 20, 1995. GGPT $IC_{50}$ (inhibition of geranylgeranyl protein transferase, in vitro enzyme assay), Cell Mat Assay, and anti-tumor activity (in vivo anti-tumor studies) could be determined by the assay procedures described in WO 95/10516. The disclosure of WO 95/10516 is incorporated herein by reference thereto.

Additional assays can be carried out by following essentially the same procedure as described above, but with substitution of alternative indicator tumor cell lines in place of the T24-BAG cells. The assays can be conducted using either DLD-1-BAG human colon carcinoma cells expressing an activated K-ras gene or SW620-BAG human colon carcinoma cells expressing an activated K-ras gene. Using other tumor cell lines known in the art, the activity of the compounds of this invention against other types of cancer cells could be demonstrated.

Soft Agar Assay:

Anchorage-independent growth is a characteristic of tumorigenic cell lines. Human tumor cells are suspended in growth medium containing 0.3% agarose and an indicated concentration of a farnesyl transferase inhibitor. The solution is overlayed onto growth medium solidified with 0.6% agarose containing the same concentration of farnesyl transferase inhibitor as the top layer. After the top layer is solidified, plates are incubated for 10–16 days at 37° C. under 5% $CO_2$ to allow colony outgrowth. After incubation, the colonies are stained by overlaying the agar with a solution of MTT (3-[4,5-dimethylthiazol 2-yl]-2,5-diphenyltetrazolium bromide, Thiazolyl blue) (1 mg/ml in PBS). Colonies can be counted and the $IC_{50}$'s can be determined.

The results are given in Table 3. In Table 3 "Ex. No." stands for "Example Number".

TABLE 3

| Ex No. | Formula No. | FPT IC$_{50}$ (nM) (H-ras) | COS Cell IC$_{50}$ (nM) |
|---|---|---|---|
| 1 | 2.0 | 12.3 | — |
| 2 | 11.0 | 5 | 30 |
| 3 | 3.0 | 6.3 | — |
| 4 | 12.0 | 5.2 | 140 |
| 5 | 4.0 | 8.4 | — |
| 6 | 13.0 | 8.1 | 39 |
| 7 | 5.0 | 31.7 | — |
| 8 | 6.0 | 7.4 | 125 |
| 9 | 7.0 | 11.6 | 700 |
| 10 | 8.0 | 8.3 | 300 |
| 11 | 9.0 | 15 | — |
| 12 | 10.0 | 4.4 | 55 |
| 19 | 12.2 | 35 | — |
| 20 | 12.3 | 5.8 | 10 |
| 21 | 12.1 | 2.5 | 10 |
| 22 | 14.2 | <2.6 | 43 |
| 23 | 14.1 | 2.7 | 14 |
| 24 | 15.1 | 4.8 | 10 |
| 25 | 15.2 | 5.1 | 39 |
| 26 | 15.3 | <2 | 125 |

Additional results are given in Table 4. "Cmpd" represents "compound" and the number in that column is the compound or structure number. The FPT IC$_{50}$ results are expressed as nanomolar (nM) in Table 4.

TABLE 4

| Cmpd | FPT IC$_{50}$ | Cmpd | FPT IC$_{50}$ | Cmpd | FPT IC$_{50}$ |
|---|---|---|---|---|---|
| 6.0-B | 2.7 | 7.0-B | <2.6 | 8.0-B | 2.8 |
| 9.0-B | 5.8 | 10.0-B | 2.5 | 11.0-B | 1.6 |
| 12.0-B | 3.0 | 13.0-B | 4.1 | 14.0-B | 0.9, 1.9 |
| 16.0-B | 5.3 | 17.0-B | 1.2 | 18.0-B | 1.2 |
| 19.0-B | 1.1 | 20.0-B | 5.6 | 21.0-B | 5.7 |
| 22.0-B | 1.8 | 23.0-B | 2.8 | 24.0-B | 0.7 |
| 26.0-B | 3.2 | 30.0-B | 2.9 | 32.0-B | 3.5 |
| 33.0-B | 2.1 | 34.0-B | 4.2 | 35.0-B | 6.4 |
| 37.0-B | 2.6 | 38.0-B | 3.2 | 39.0-B | 4.1 |
| 44.0-B | 2.6 | 49.0-B | 2.1 | 50.0-B | 3.3 |
| 51.0-B | 8.1 | 52.0-B | 1.3 | 53.0-B | 3.6 |
| 54.0-B | 3.9 | 55.0-B | 9.2 | 56.0-B | 3.3 |
| 57.0-B | 1.8 | 58.0-B | 16 | 59.0-B | 4.0 |
| 60.0-B | 5.4 | 63.0-B | 3.5 | 64.0-B | 5.2 |
| 67.0-B | 3.5 | 68.0-B | 6.9 | 69.0-B | 2.5 |
| 70.0-B | 1.4 | 71.0-B | 3.3 | 72.0-B | 5.4 |
| 74.0-B | 1.7 | 75.0-B | 4.7 | 76.0-B | 6.7 |
| 77.0-B | 3.2 | 79.0-B | 4.4 | 81.0-B | 9.3 |
| 82.0-B | 7.1 | 85.0-B | 5.0 | 86.0-B | 18 |
| 88.0-B | 2.2 | 89.0-B | 8.7 | 90.0-B | 3.8 |
| 92.0-B | 2.2 | 95.0-B | 8.3 | 101.0-B | 5.3 |
| 107.0-B | 3.6 | 114.0-B | 3.9 | 114.2-B | 3.9 |
| 114.3-B | 7.2 | 114.4-B | 7.8 | — | — |

The following compounds had the following FPT IC$_{50}$ (H-ras) results: 79.0-B, 4.4 nM; 23.0-B, 2.8 nM; 104.0-B, 4.6 nM, 108.0-B, 3.5 nM; 16.0, 5 nM; 17.0, 5.2 nM; and 18.0, 8.1 nM.

The following compounds had the following FPT IC$_{50}$ (K-ras) results: 2.0, 43.2 nM; 3.0, 30 nM; 4.0, 22 nM; 6.0, 41 nM; 8.0, 71.2 nM; 9.0, 49 nM; 12.1, 19.4 nM; 12.3, 19.8 nM; 7.0, 34.8 nM; 10.0, 35 nM; 6.0-B, 14.5 nM; 9.0-B, 41 nM: 10.0-B, 15.8 nM; 11.0-B, 12.6 nM; 12.0-B, 26.7 nM; 13.0-B, 19.7 nM; 7.0-B, 15.4 nM; 16.0, 20.5 nM; 17.0, 23.8 nM; and 18.0, 31 nM.

Additional results are given in Table 5. "Cmpd" represents "compound" and the number in that column is the compound or structure number. The FPT IC$_{50}$, COS Cell IC$_{50}$ and Soft Agar IC$_{50}$ results are expressed as nanomolar (nM) in Table 5.

TABLE 5

| Cmpd | Cos Cell | Soft Agar | Cmpd | Cos Cell | Soft Agar |
|---|---|---|---|---|---|
| 6.0 | 125 | — | 12.1 | — | 160, 90 |
| 12.3 | — | 190 | 88.0-B | 23 | >500 |
| 89.0-B | 550 | >500 | 10.0 | — | 250 |
| 24.0-B | 100 | >500 | 63.0-B | 55 | 500 |
| 6.0-B | 30 | 210 | 9.0-B | 25 | >500 |
| 10.0-B | 20 | >300 | 11.0-B | 29 | >500 |
| 12.0-B | 20 | >500 | 13.0-B | 25 | >500 |
| 16.0-B | 16 | 90 | 21.0-B | — | >500 |
| 22.0-B | 35 | 19.5, 27.5 | 26.0-B | 30 | >500 |
| 30.0-B | 9 | 500 | 34.0-B | 9 | 460 |
| 35.0-B | 30, 50 | 300 | 37.0-B | 100, <10 | 75 |
| 38.0-B | 10 | 210 | 39.0-B | 16 | 220 |
| 44.0-B | <10 | 120 | 52.0-B | 400 | 500 |
| 53.0-B | 50 | >500 | 54.0-B | 100 | >500 |
| 55.0-B | 200 | >500 | 56.0-B | 50 | >500 |
| 57.0-B | <10 | 110 | 75.0-B | 10 | 150 |
| 77.0-B | 14 | 240, 214 | 79.0-B | 150 | >500 |
| 82.0-B | <10 | >500 | 85.0-B | 14 | 333 |
| 95.0-B | 11 | >500 | 114.2-B | 10 | 75 |
| 114.3-B | 11 | 432 | 114.4-B | 10 | 363 |
| 7.0-B | 43 | — | 23.0-B | <10 | >500 |
| 17.0-B | >1000 | >500 | 32.0-B | 28 | >500 |
| 33.0-B | 10 | >120 | 49.0-B | 38 | >500 |
| 59.0-B | 50 | 500 | 60.0-B | 120 | 500 |
| 64.0-B | 10 | 130 | 72.0-B | 10 | 320 |
| 81.0-B | 28 | >500 | 104.0-B | 40 | >500 |
| 15.2 | — | 250 | 14.0-B | 250, 200 | >500 |
| 18.0-B | 75 | >500 | 19.0-B | 17.5, <10 | 440, 500 275, 197 |
| 50.0-B | <10 | 95 | 51.0-B | 280 | — |
| 68.0-B | 10 | 220 | 69.0-B | 25 | 190 |
| 70.0-B | 25 | 250 | 71.0-B | 19 | 240 |
| 74.0-B | 40 | 500 | 92.0-B | 15 | 45 |
| 101.0-B | 10 | 320 | 107.0-B | 30 | 480 |
| 108.0-B | 30 | — | 114.0-B | 35 | 395 |
| 16.0 | 30 | 75 | 17.0 | 140 | — |
| 18.0 | 39 | 200 | | | |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

PHARMACEUTICAL DOSAGE FORM EXAMPLES

Example A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp ogranules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

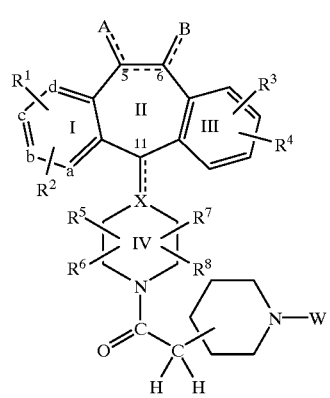

(1.0)

or a pharmaceutically acceptable salt or solvate thereof, wherein:

One of a, b, c and d represents N or $NR^9$ wherein $R^9$ is $O^-$, $-CH_3$ or $-(CH_2)_nCO_2H$ wherein n is 1 to 3, and the remaining a, b, c and d groups represent $CR^1$ or $CR^2$; or each of a, b, c, and d are independently selected from $CR^1$ or $CR^2$; each $R^1$ and each $R^2$ is independently selected from H, halo, $-CF_3$, $-OR^{10}$, $-COR^{10}$, $-SR^{10}$, $-S(O)_tR^{11}$ (wherein t is 0, 1 or 2), $-SCN$, $-N(R^{10})_2$, $-NR^{10}R^{11}$, $-NO_2$, $-OC(O)R^{10}$, $-CO_2R^{10}$, $-OCO_2R^{11}$, $-CN$, $-NHC(O)R^{10}$, $-NHSO_2R^{10}$, $-CONHR^{10}$, $-CONHCH_2CH_2OH$, $-NR^{10}COOR^{11}$,

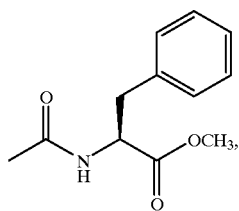

—SR$^{11}$C(O)OR$^{11}$, —SR$^{11}$N(R$^{75}$)$_2$ wherein each R$^{75}$ is independently selected from H and —C(O)OR$^{11}$, benzotriazol-1-yloxy, tetrazol-5-ylthio, or substituted tetrazol-5-ylthio, alkynyl, alkenyl or alkyl, said alkyl or alkenyl group optionally being substituted with halo, —OR$^{10}$ or —CO$_2$R$^{10}$;

R$^3$ and R$^4$ are the same or different and each independently represents H, any of the substituents of R$^1$ and R$^2$, or R$^3$ and R$^4$ taken together represent a saturated or unsaturated C$_5$–C$_7$ fused ring to the benzene ring (Ring III);

R$^5$, R$^6$, R$^7$ and R$^8$ each independently represents H, —CF$_3$, —COR$^{10}$, alkyl or aryl, said alkyl or aryl optionally being substituted with —OR$^{10}$, —SR$^{10}$, —S(O)$_t$R$^{11}$, —NR$^{10}$COOR$^{11}$, —N(R$^{10}$)$_2$, —NO$_2$, —COR$^{10}$, —OCOR$^{10}$, —OCO$_2$R$^{11}$, —CO$_2$R$^{10}$, OPO$_3$R$^{10}$, or R$^5$ is combined with R$^6$ to represent =O or =S and/or R$^7$ is combined with R$^8$ to represent =O or =S;

R$^{10}$ represents H, alkyl, aryl, or aralkyl;

R$^{11}$ represents alkyl or aryl;

X represents CH when the optional bond to carbon 11 is absent and C when the optional bond is present;

the dotted line between carbon atoms 5 and 6 represents ail optional double bond, such that when a double bond is present, A and B independently represent —R$^{10}$, halo, —OR$^{11}$, —OCO$_2$R$^{11}$ or —OC(O)R$^{10}$, and when no double bond is present between carbon atoms 5 and 6, A and B each independently represent H$_2$, —(OR$^{11}$)$_2$; H and halo, dihalo, alkyl and H, (alkyl)$_2$, —H and —OC(O)R$^{10}$, H and —OR$^{10}$, =O, aryl and H, =NOR$^{10}$ or —O—(CH$_2$)$_p$—O— wherein p is 2, 3 or 4; and W represents a group selected from the group consisting of:

(1)

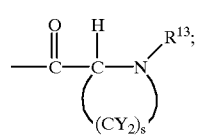

(2)

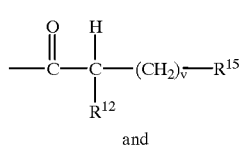

and (3)

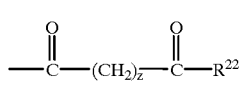

wherein:

R$^{12}$ is selected from the group consisting of: (a) H; (b) alkyl; (c) aralkyl; and (d) heteroarylalkyl;

R$^{13}$ is selected from the group consisting of: (a) H; (b) —C(O)OR$^{16}$ wherein R$^{16}$ represents alkyl, aralkyl, and heteroaralkyl; (c) —SO$_2$R$^{17}$ wherein R$^{17}$ is selected from the group consisting of: NH$_2$, —N(alkyl)$_2$ wherein each alkyl is the same or different, alkyl, aryl, aralkyl, heteroaryl and heteroaralkyl; (d) —C(O)R$^{18}$ wherein R$^{18}$ is selected from the group consisting of: aryl, alkyl, aralkyl, heteroaryl, and heteroaralkyl; (e) C$_{1-6}$ alkyl; (f) alkaryl; and (g) C$_{3-6}$ cycloalkyl;

r is 0, 1 or 2;

s represents 1, 2, 3, 4, or 5, and each Y for each —CY$_2$— group is independently selected from H or —OH, provided that both Y substituents of each —CY$_2$— group are not —OH, and provided that for the —CY$_2$— group alpha to the nitrogen both Y substituents are H, such that the group

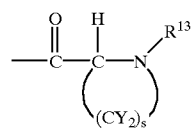

forms a 3, 4, 5, 6, or 7 membered ring;

v is 0, 1 or 2;

R$^{15}$ is selected from the group consisting of:
(a) heteroaryl;
(b) a group selected from:

(1)

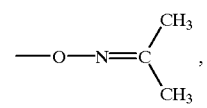

(2)

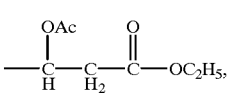

(3)

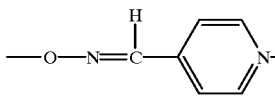

(4)

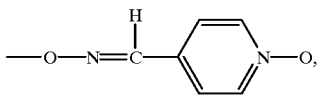

(5) —CH(OCH$_2$CH$_3$)$_2$,
(6) —OH, and
(7) —CN; and
(c) heterocycloalkyl selected from the group consisting of:

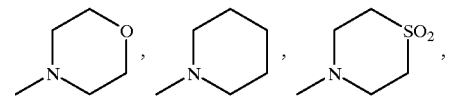

-continued

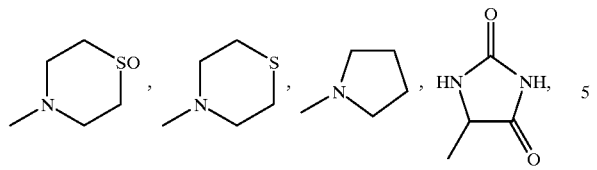

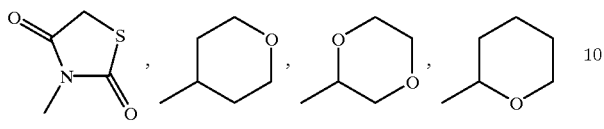

and

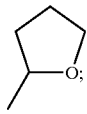

z is 0, 1, 2, 3, 4, or 5 wherein each —CH$_2$— group is optionally substituted with a —OH group;

R$^{22}$ represents a group selected from:

(1) 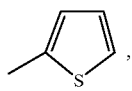

(2) 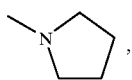

(3) 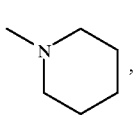

(4) 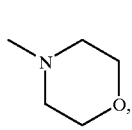

(5) alkyl, (6) —OR$^{23}$ wherein R$^{23}$ is selected from the group consisting of: alkyl, aryl and H, and (7) 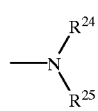

wherein R$^{24}$ and R$^{25}$ are independently selected from the group consisting of: —NH$_2$, alkoxy, —OH, —CH$_2$CO$_2$H, —OCH$_2$Ph, —CH(OCH$_3$)CH(CH$_3$)$_2$, alkyl, aryl, H, aralkyl, and heteroaralkyl; or R$^{24}$ and R$^{25}$ taken together form a carbon chain having 4 or 5 (—CH$_2$—) groups such that R$^{24}$ and R$^{25}$ taken together with the nitrogen to which they are bound form a 5 or 6 membered heterocycloalkyl ring.

2. The compound of claim 1 wherein R$^2$ is H; R$^1$ is selected from the group consisting of: Br and Cl; R$^3$ is selected from the group consisting of: Br and Cl; R$^4$ is selected from the group consisting of: H, Br and Cl; R$^5$, R$^6$, R$^7$ and R$^8$ are H; A and B are each H$_2$; and the optional bond between C5 and C6 is absent.

3. The compound of claim 2 wherein R$^4$ is H.

4. The compound of claim 2 wherein R$^4$ is selected from the group consisting of: Cl or Br.

5. The compound of claim 4 wherein W is selected from the group consisting of:

(A)

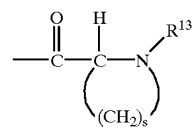

wherein:

(1) s is 1, 2, 3,4 or 5; and (2) R$^{13}$ is selected from the group consisting of: (a) H and —C(O)OR$^{16}$ wherein R$^{16}$ is alkyl;

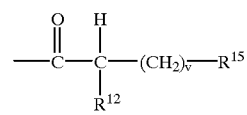

wherein:

(1) v is 0;

(2) R$^{12}$ is H; and (3) R$^{15}$ is selected from the group consisting of:

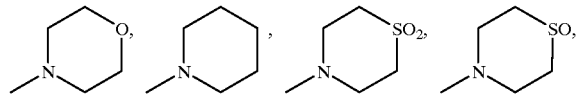

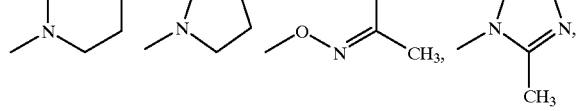

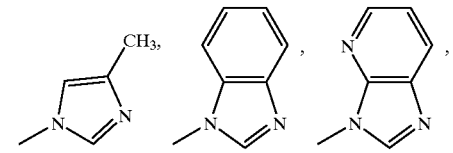

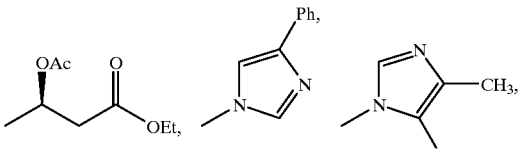

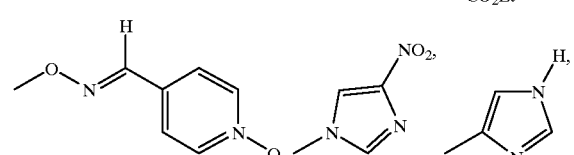

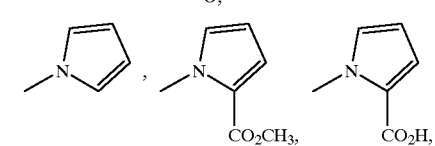

-continued

[chemical structures: N-methyl pyrrole with CO₂Et and CH₃; N-methyl pyrrole with CO₂CH₂Ph; N-methyl imidazole with CH₂C(O)OCH₃; N-methyl triazole; CH(OEt)₂; methylhydantoin; N-methyl thiazolidinedione; methylthiophene; methyltetrahydropyran]

[chemical structures: salicylaldehyde O-methyloxime; dioxane derivative; tetrahydropyran derivative]

[chemical structure: tetrahydrofuran derivative]

and —OH, —CN;

(C)

$$-\overset{O}{\underset{}{C}}-\overset{H}{\underset{R^{12}}{C}}-(CH_2)_v-R^{15}$$

wherein:

(1) v is 1 or 2;
(2) $R^{12}$ is H; and
(3) $R^{15}$ is heterocycloalkyl (D)

$$-\overset{O}{\underset{}{C}}-(CH_2)_z-\overset{O}{\underset{}{C}}-R^{22}$$

wherein:

(1) z is 0;
(2) $R^{22}$ is —NR²⁴R²⁵; and
(3) $R^{24}$ and $R^{25}$ are independently selected from: H, —NH₂, alkyl, alkoxy, —OH, —CH₂CO₂H, or —OCH₂C₆H₅; and (E)

$$-\overset{O}{\underset{}{C}}-(CH_2)_z-\overset{O}{\underset{}{C}}-R^{22}$$

wherein:

(1) z is 1, 2, 3, 4 or 5;
(2) $R^{22}$ is selected from: —OR²³, —ONa, —OLi, alkyl, —NR²⁴R²⁵ or

[methylthiophene structure];

(3) $R^{23}$ is alkyl; and
(4) $R^{24}$ and $R^{25}$ are independently selected from H, —CH(OCH₃)CH(CH₃)₂, or $R^{24}$ and $R^{25}$ together form

[pyrrolidine, piperidine, or morpholine structures]

6. The compound of claim 5 wherein X is CH.

7. The compound of claim 6 wherein $R^1$ is Br, $R^3$ is Cl and $R^4$ is Br.

8. The compound of claim 1 selected from:

(1.4)

[tricyclic structure with R¹, R³, R⁴ substituents, A, B, X positions, and piperidine-acetyl-piperidine-W side chain]

or (1.5)

[tricyclic structure similar to 1.4 with different R⁴ position]

wherein $R^1$, $R^3$ and $R^4$ are each independently selected from halo; and A, B, X and W are as defined in claim 1.

9. The compound of claim 8 wherein $R^1$ is selected from the group consisting of: Br and Cl; $R^3$ and $R^4$ are independently selected from the group consisting of: Br and Cl; A and B are each H₂; and the optional bond between C5 and C6 is absent.

10. The compound of claim 9 wherein $R^1$ is Br; $R^3$ is Cl; and $R^4$ is Br.

11. The compound of claim 10 wherein W is selected from the group consisting of:

(A)
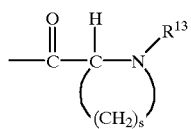
wherein:
(1) s is 1, 2, 3, 4 or 5; and
(2) $R^{13}$ is selected from the group consisting of: (a) H and —C(O)OR$^{16}$ wherein R$^{16}$ is alkyl;
(B)
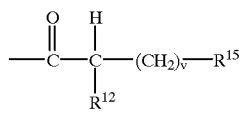
wherein:
(1) v is 0;
(2) $R^{12}$ is H; and
(3) $R^{15}$ is selected from the group consisting of:
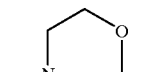 , 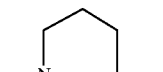 ,
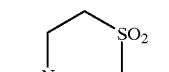 , 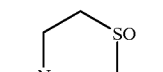 ,
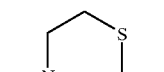 ,  ,
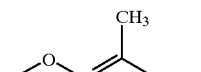 , 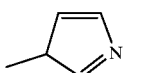 ,
 , 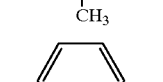 ,
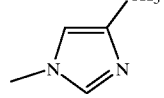 , 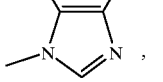 ,
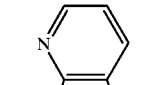 ,  ,
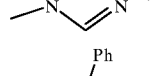 ,  ,
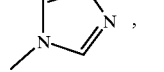 , 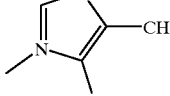 ,
-continued
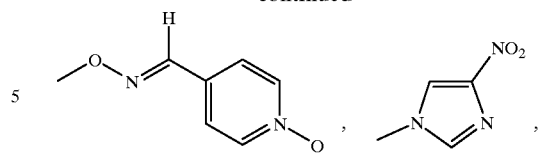
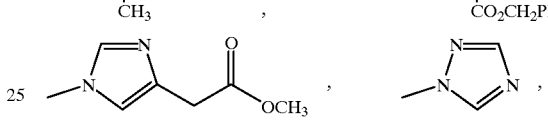
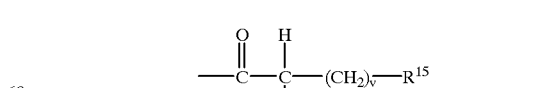
and —OH, —CN;
(C)
wherein:
(1) v is 1 or 2;
(2) $R^{12}$ is H; and (3) $R^{15}$ is heterocycloalkyl;

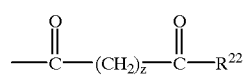
(D)

wherein:

(1) z is 0;

(2) $R^{22}$ is —$NR^{24}R^{25}$; and (3) $R^{24}$ and $R^{25}$ are independently selected from: H, —$NH_2$, alkyl, alkoxy, —OH, —$CH_2CO_2H$, or —$OCH_2C_6H_5$; and

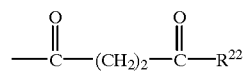
(E)

wherein:

(1) z is 1, 2, 3, 4 or 5;

(2) $R^{22}$ is selected from: —$OR^{23}$, —ONa, —OLi, alkyl, —$NR^{24}R^{25}$ or

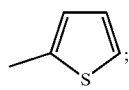
;

(3) $R^{23}$ is alkyl; and (4) $R^{24}$ and $R^{25}$ are independently selected from H, —$CH(OCH_3)CH(CH_3)_2$, or $R^{24}$ and $R^{25}$ together form

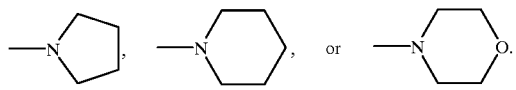

12. The compound of claim 11 wherein X is CH.

13. The compound of claim 12 wherein W is selected from the group consisting of:

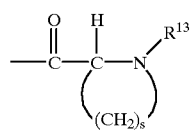

wherein:

(1) s is 3; and (2) $R^{13}$ is selected from the group consisting of: (a) H and —$C(O)OC(CH_3)_3$;

(B)

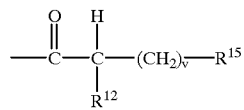

wherein:

(1) v is 0;

(2) $R^{12}$ is H; and (3) $R^{15}$ is selected from the group consisting of:

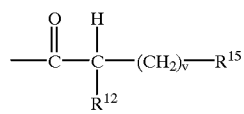
;

(C)

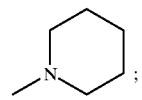

wherein:

(1) v is 1 or 2;

(2) $R^{12}$ is H; and (3) $R^{15}$ is

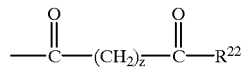
;

(D)

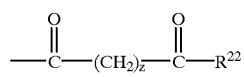

wherein:

(1) z is 0;

(2) $R^{22}$ is —$NR^{24}R^{25}$; and (3) $R^{24}$ and $R^{25}$ are each H; and (E)

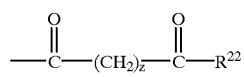

wherein:

(1) z is 1, 2 or 3;

(2) $R^{22}$ is —$OR^{23}$; and (3) $R^{23}$ is methyl or ethyl.

14. The compound of claim 12 wherein said compound is compound of the formula:

(1.5)
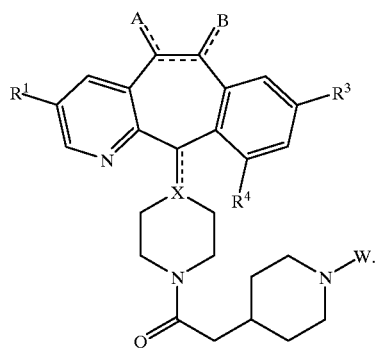
15. The compound of Formula 1.0 of claim 1 wherein W is
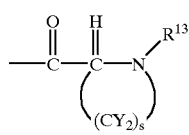
s is 3 and said compound is selected from the group consisting of:
(7.0)
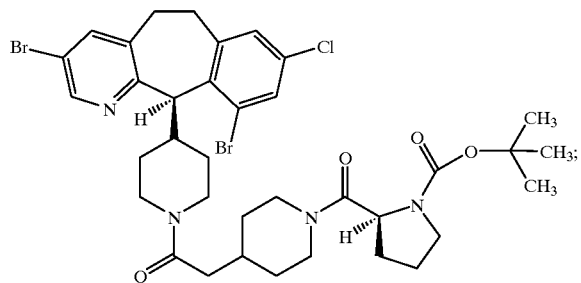
(10.0)
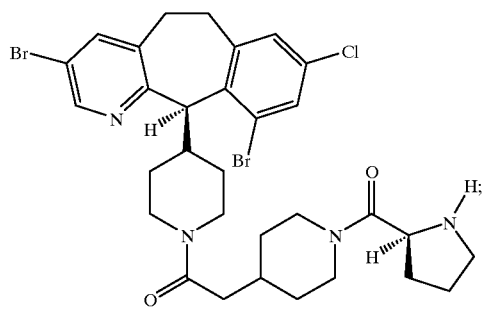
(24.0-B)
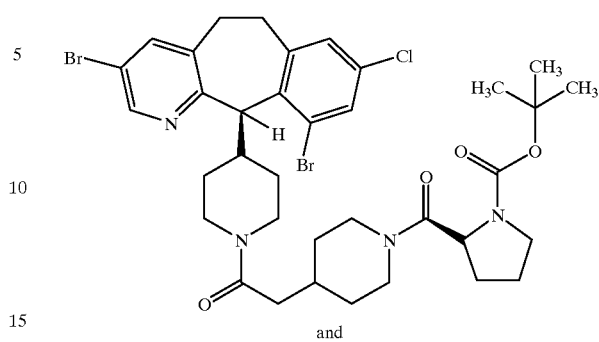
and
(63.0-B)
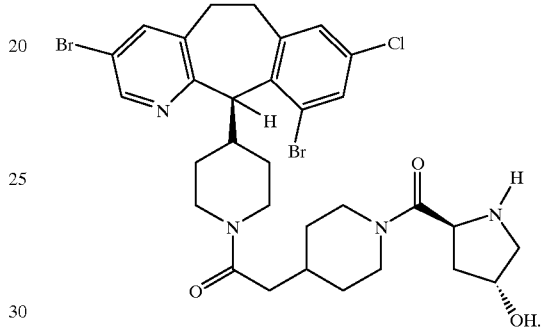
16. A compound selected from the group consisting of:
(13.0)
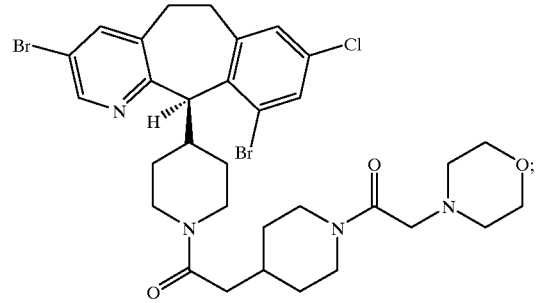
(14.0)
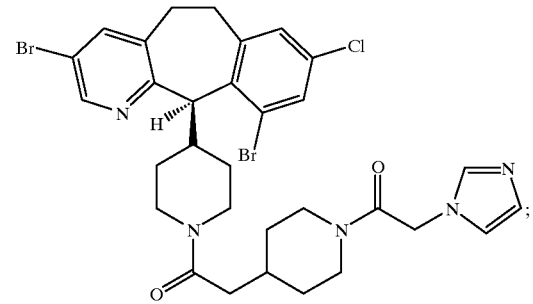

(14.1)
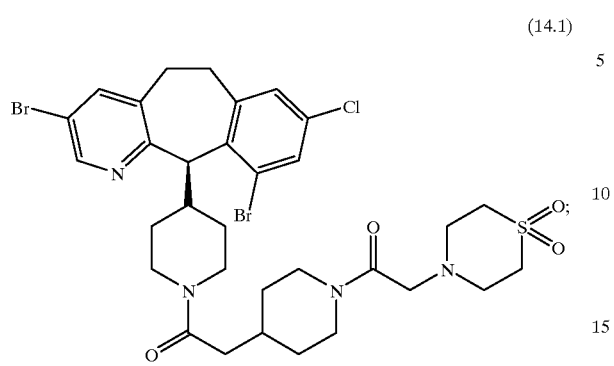
(11.0-B)
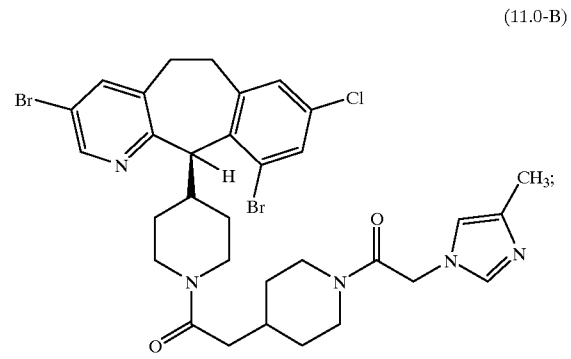
(6.0-B)
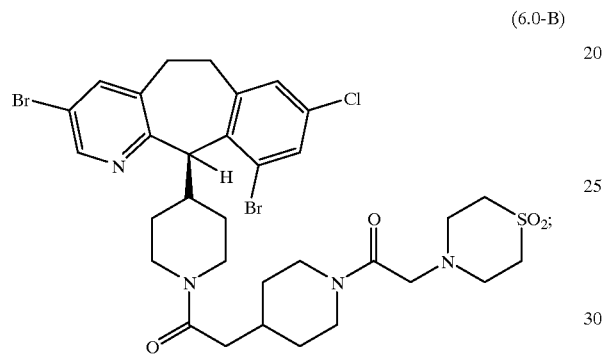
(12.0-B)
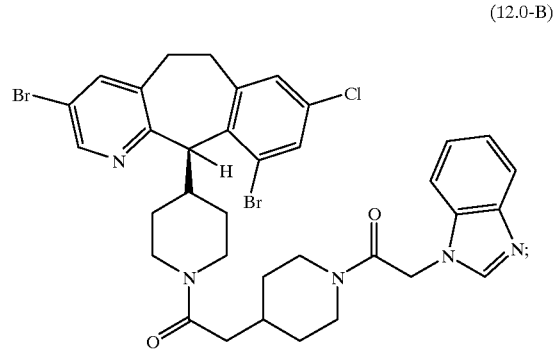
(9.0-B)
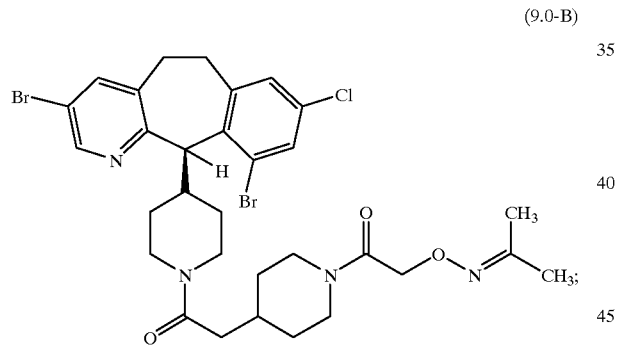
(13.0-B)
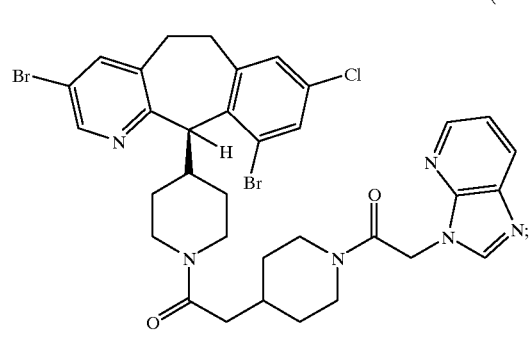
(10.0-B)
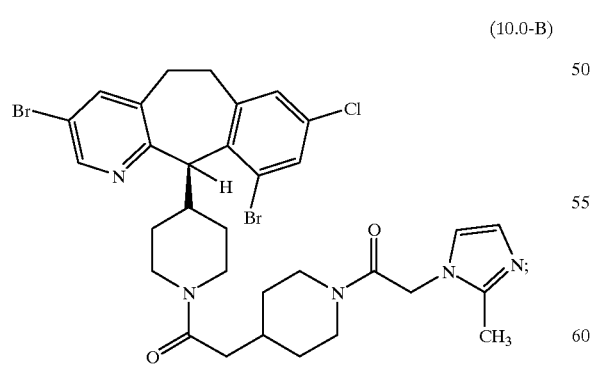
(16.0-B)
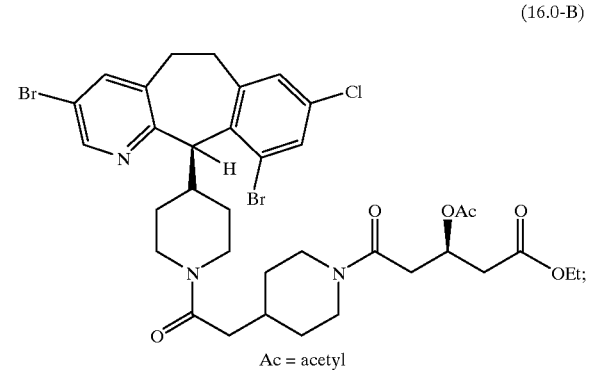
Ac = acetyl (20.0-B)
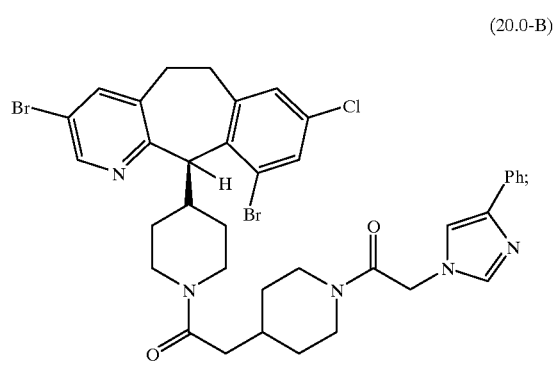
(21.0-B)
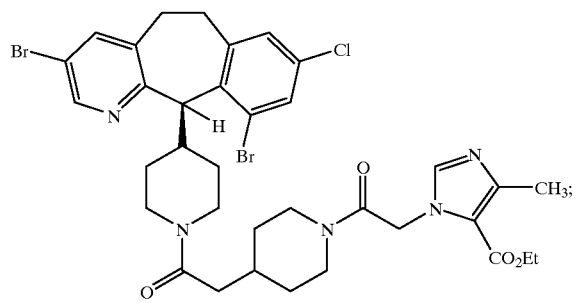
(22.0-B)
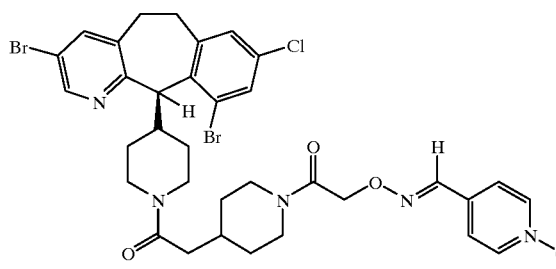
(26.0-B)
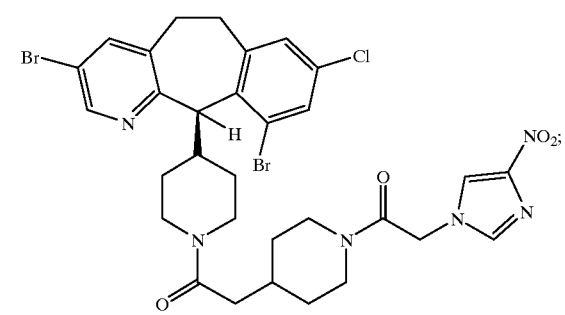
(30.0-B)
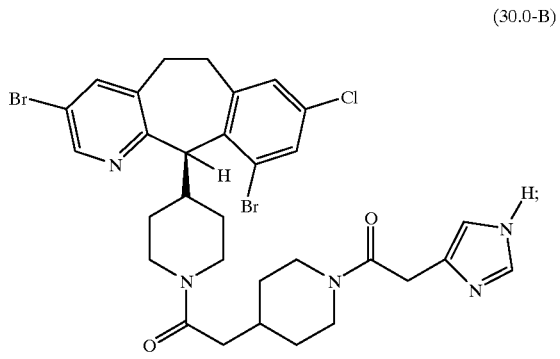
(34.0-B)
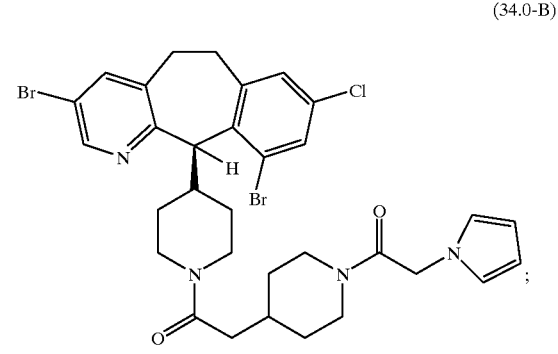
(35.0-B)
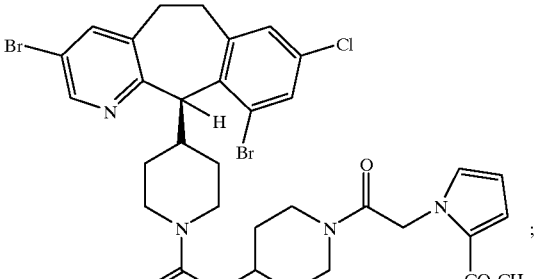
(37.0-B)
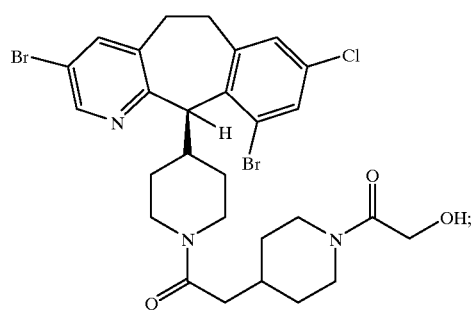

(38.0-B)
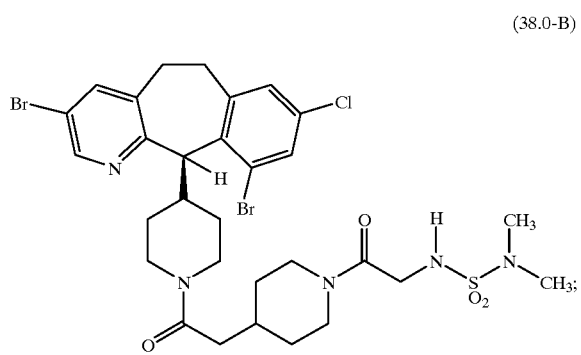
(39.0-B)
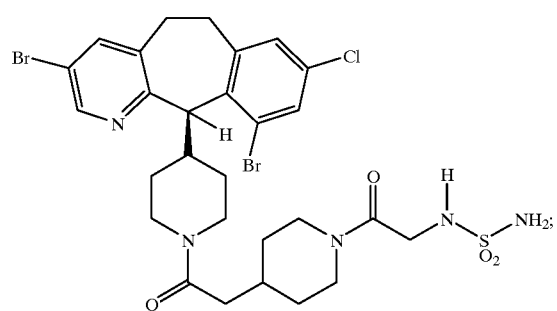
(44.0-B)
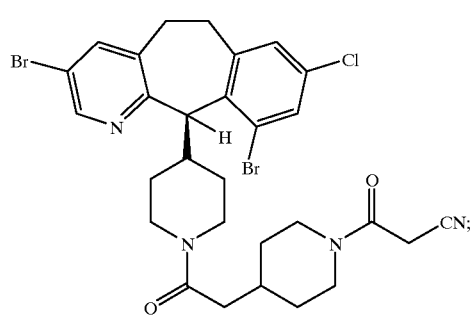
(52.0-B)
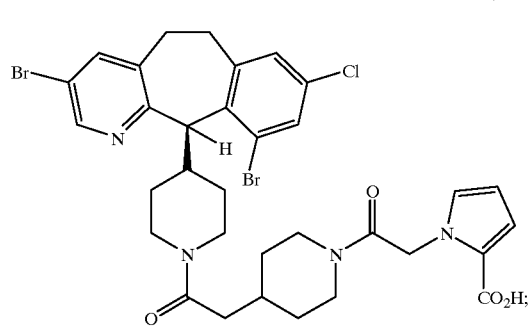
(53.0-B)
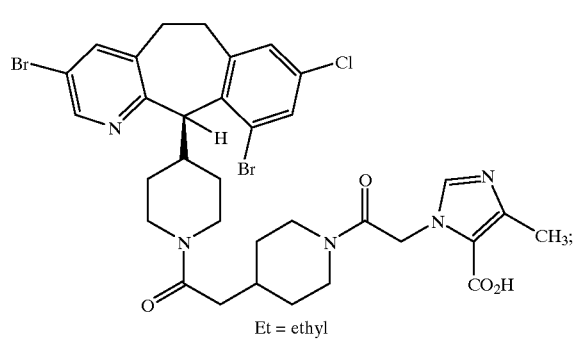
Et = ethyl
(54.0-B)
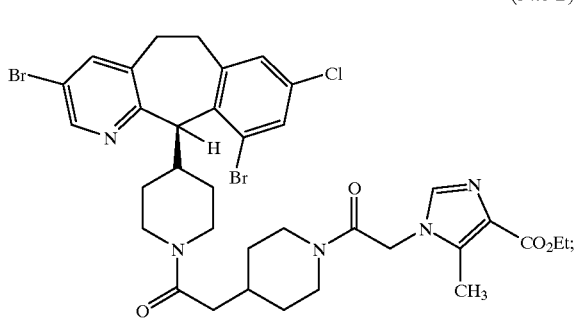
(55.0-B)
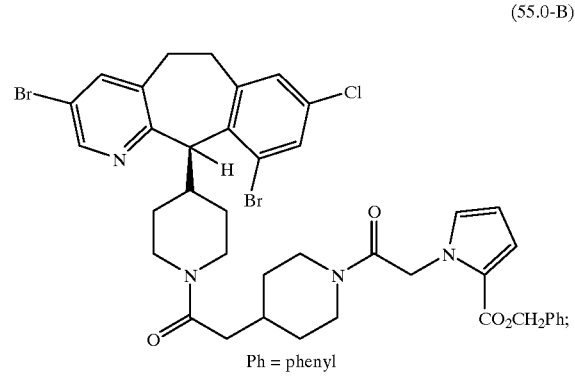
Ph = phenyl
(56.0-B)
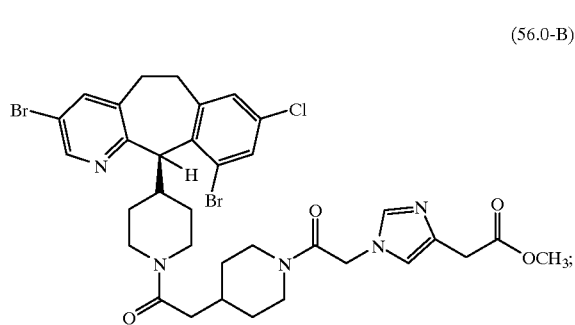

(57.0-B)
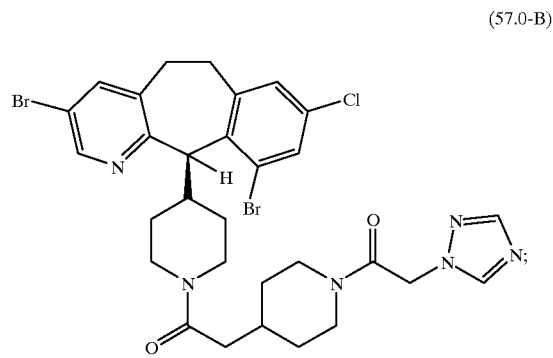
(75.0-B)
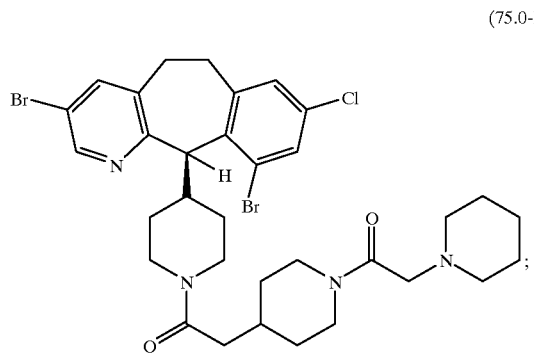
(76.0-B)
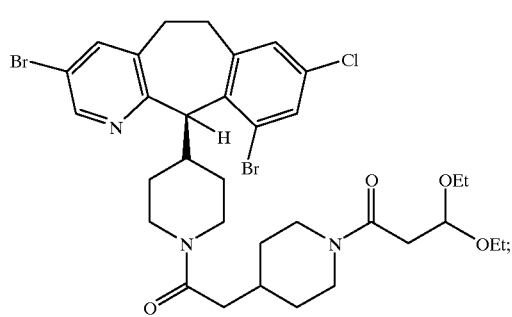
(77.0-B)
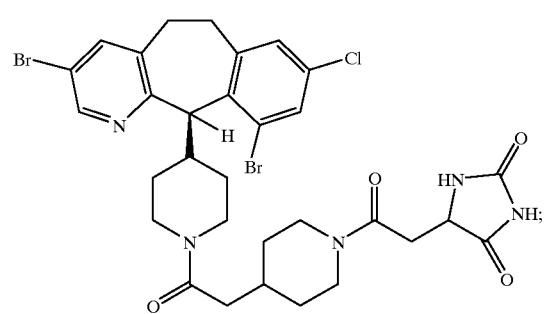
(79.0-B)
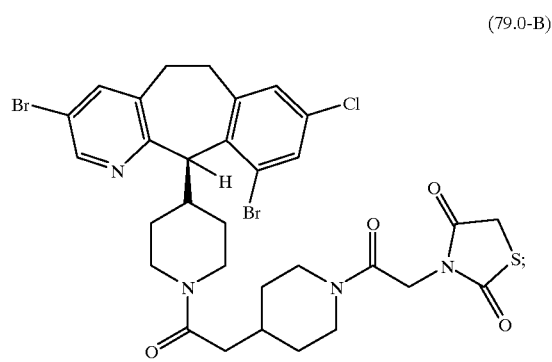
(82.0-B)
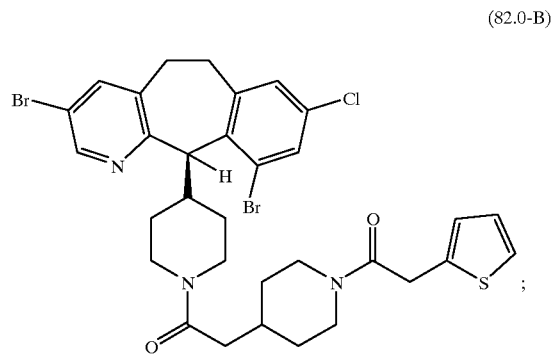
(85.0-B)
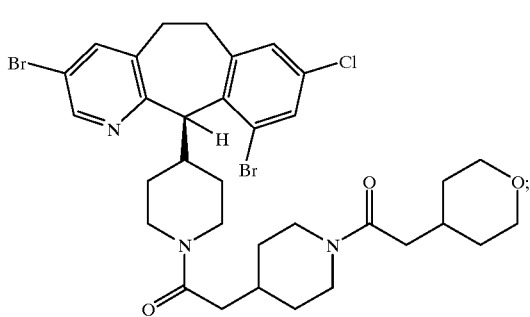
(95.0-B)
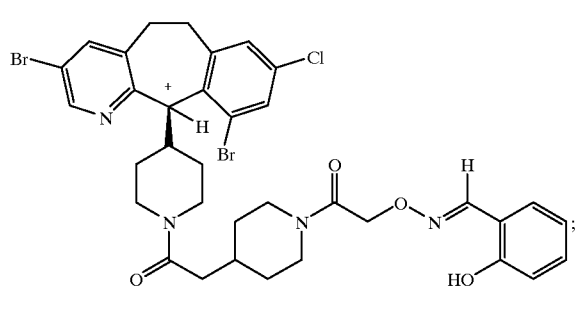

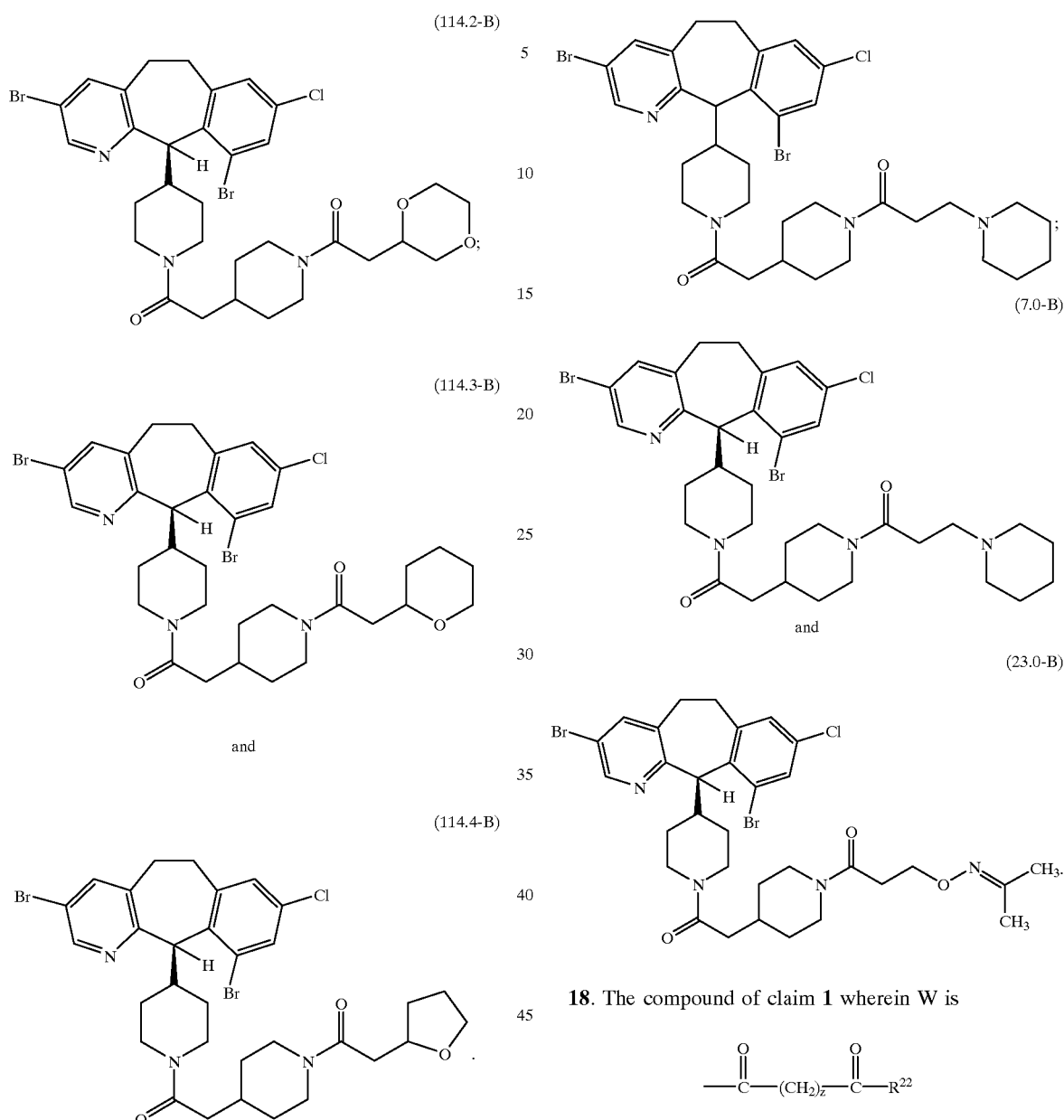
17. The compound of claim 1 wherein W is
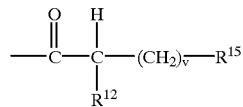
v is 1 and said compound is selected from the group consisting of:
18. The compound of claim 1 wherein W is
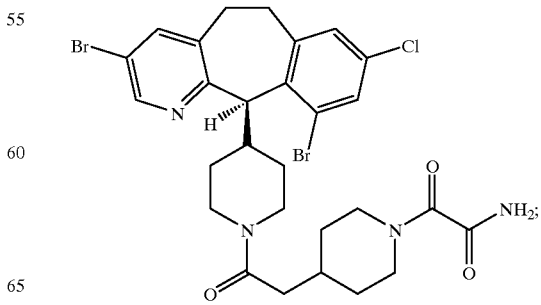
z is 0 and said compound is selected from the group consisting of:

(17.0-B)
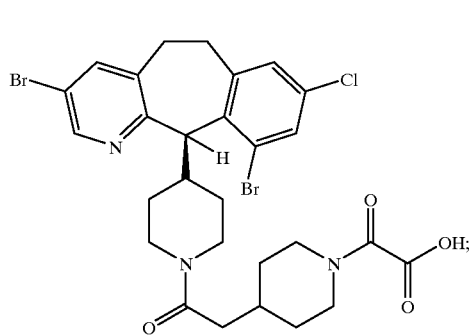
(58.0-B)
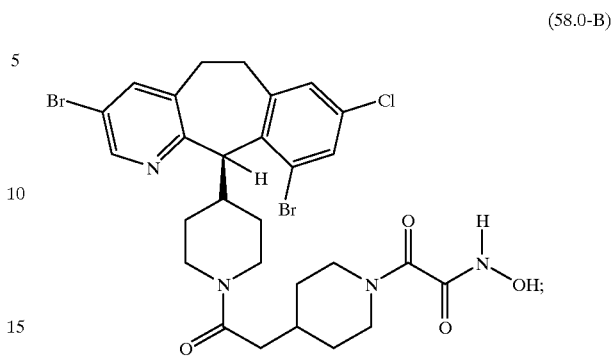
(32.0-B)
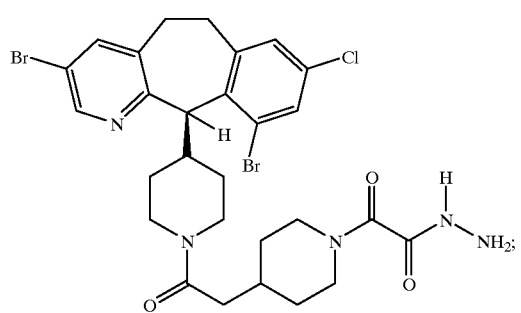
(59.0-B)
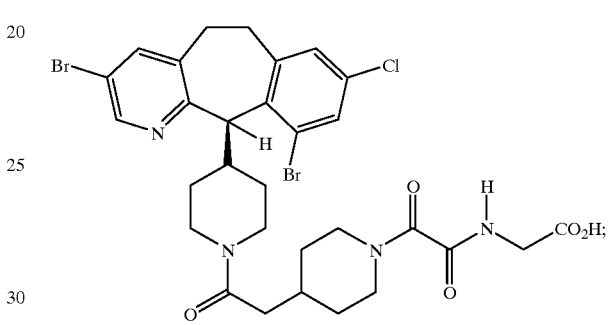
(33.0-B)
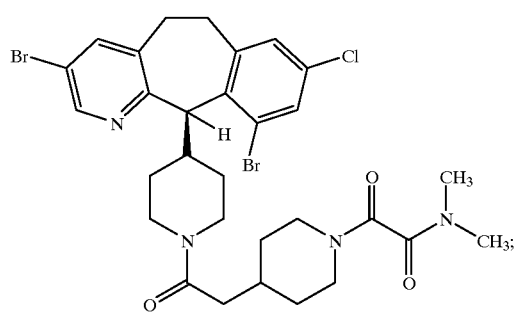
(60.0-B)
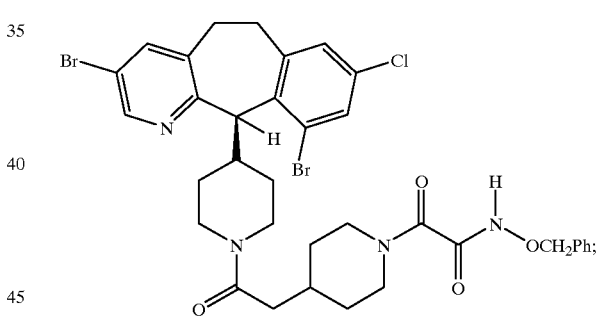
(49.0-B)
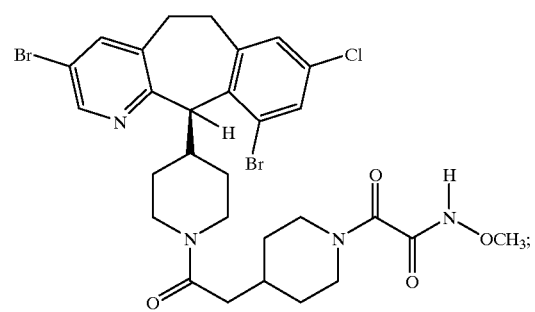
(64.0-B)
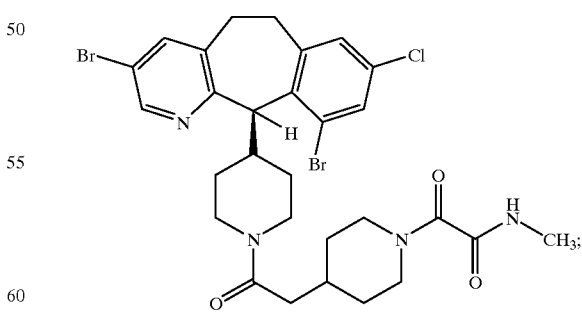

-continued
(72.0-B)
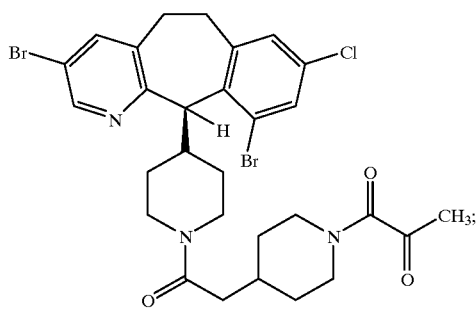
(81.0-B)
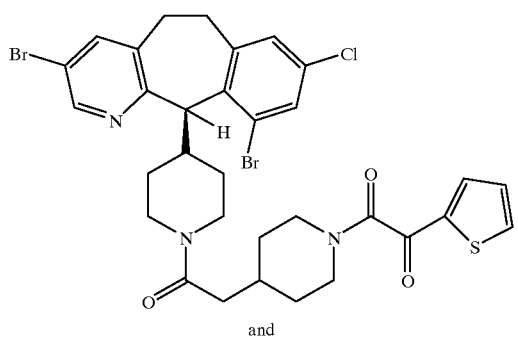
and
(104.0-B)
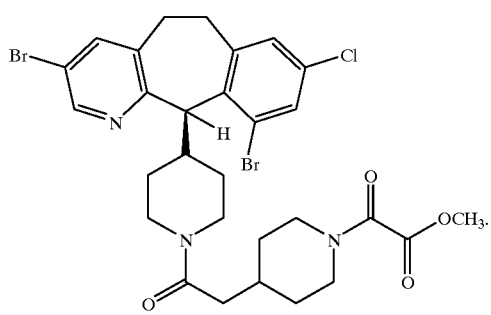
19. The compound of claim 1 wherein W is
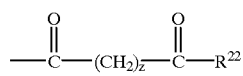
z is 1, 2, 3, 4 or 5 and said compound is selected from the group consisting of:
(15.1)
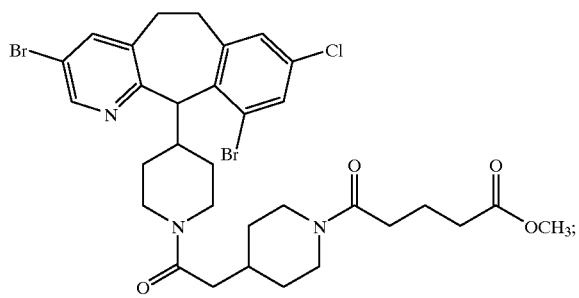
-continued
(15.2)
(15.3)
(14.0-B)
(18.0-B)
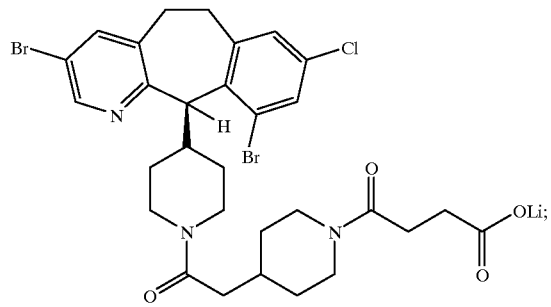

-continued
(19.0-B)
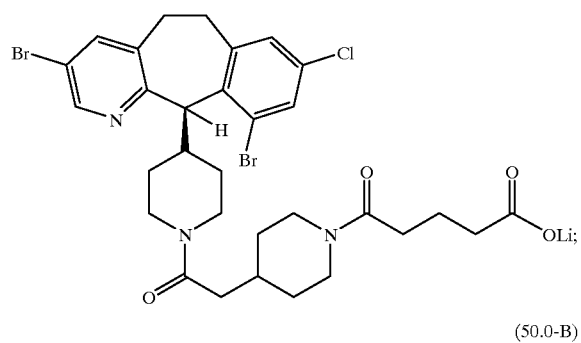
(50.0-B)
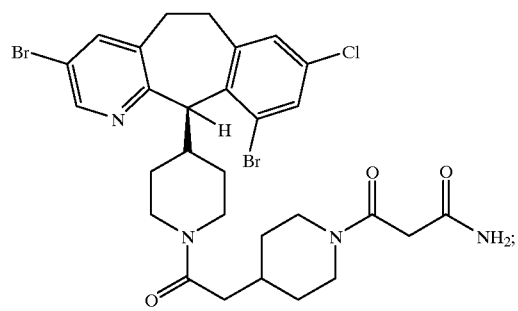
(51.0-B)
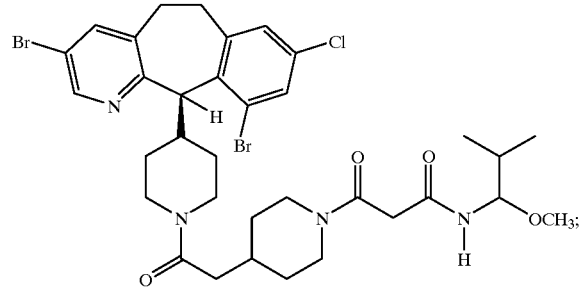
(67.0-B)
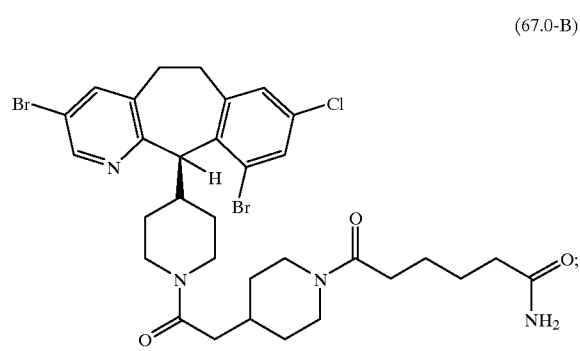
(68.0-B)
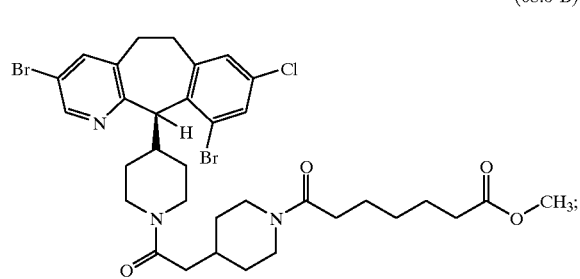
-continued
(69.0-B)
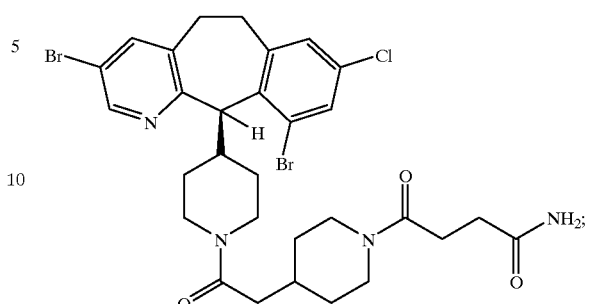
(70.0-B)
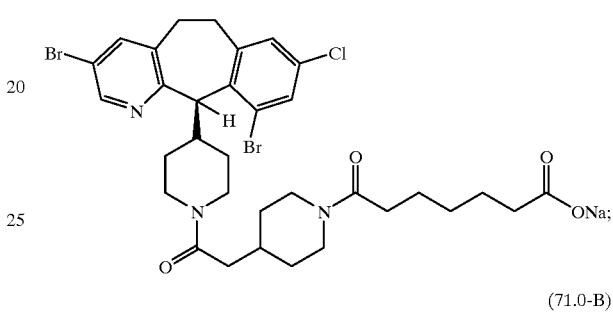
(71.0-B)
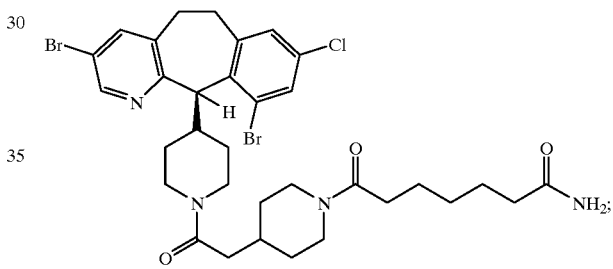
(74.0-B)
(92.0-B)
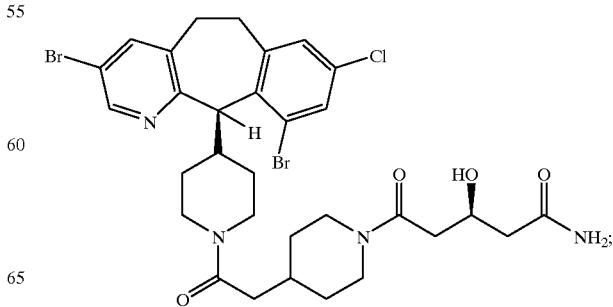

(101.0-B)
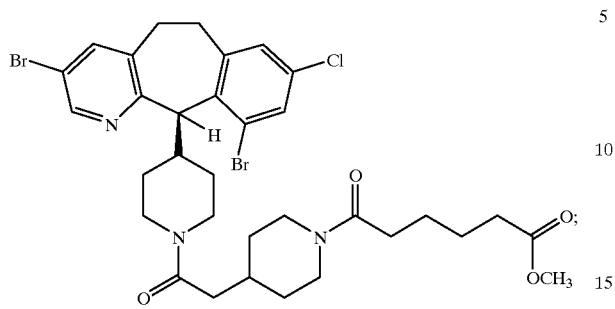
(110.0-B)
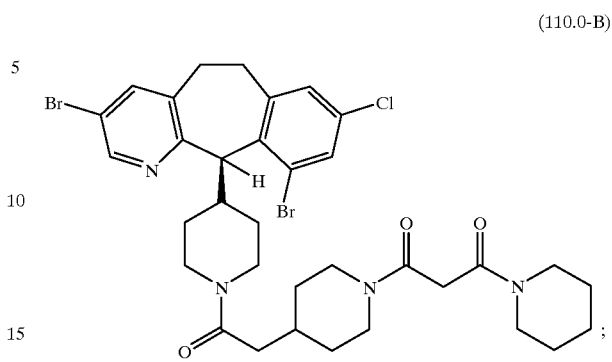
(107.0-B)
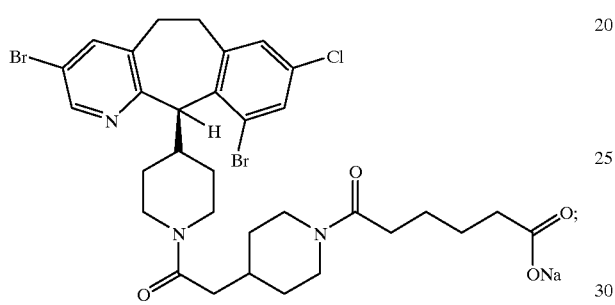
(111.0-B)
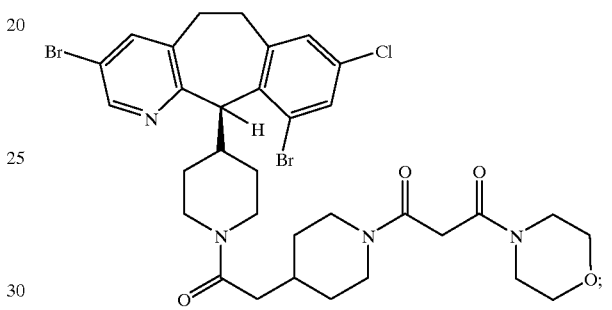
(108.0-B)
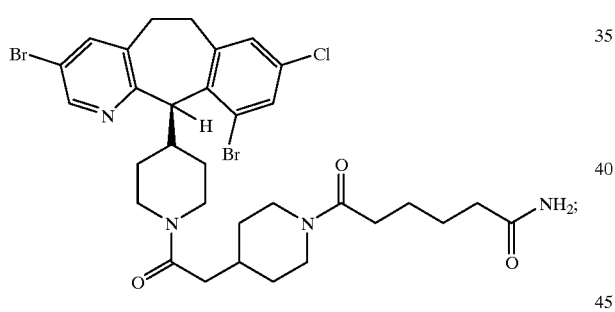
(112.0-B)
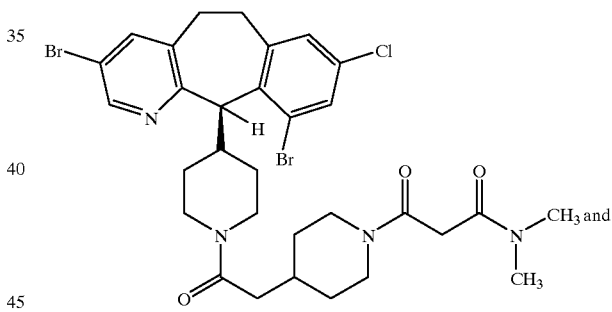
(109.0-B)
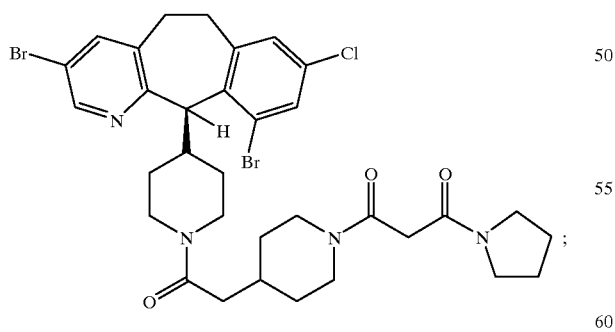
(114.0-B)
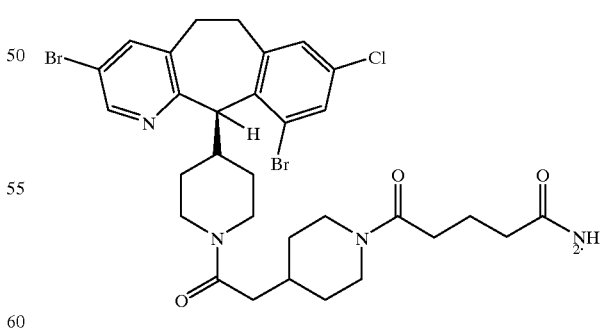

20. A method of treating tumor cells, wherein the cells treated are pancreatic tumor cells, lung cancer cells, myeloid leukemia tumor cells, thyroid follicular tumor cells, myelodysplastic tumor cells, epidermal carcinoma tumor cells, bladder carcinoma tumor cells or colon tumors cells, in a human by inhibition of farnesyl protein transferase comprising administering to a human in need thereof a compound of claim 1 in an amount that inhibits farnesyl protein transferase.

21. A method of inhibiting farnesyl protein transferase in a human comprising the administration of the compound of claim 1 to a human in need thereof in an amount that inhibits farnesyl protein transferase.

22. A pharmaceutical composition comprising an effective amount of compound of claim 1 in combination with a pharmaceutically acceptable carrier.

23. A method of inhibiting farnesyl protein transferase in a human comprising the administration of the compound of claim 19 to a human in need thereof in an amount that inhibits farnesyl protein transferase.

24. A pharmaceutical composition comprising an effective amount of compound of claim 19 in combination with a pharmaceutically acceptable carrier.

* * * * *